(12) United States Patent
Daneshvar

(10) Patent No.: US 7,901,372 B2
(45) Date of Patent: Mar. 8, 2011

(54) DANESHVAR WOUND DRESSING, SUPPORT UNITS AND METHODS, MODEL JASMINE

(76) Inventor: Yousef Daneshvar, West Bloomfield, MI (US)

( * ) Notice: Subject to any disclaimer, the term of this patent is extended or adjusted under 35 U.S.C. 154(b) by 2223 days.

(21) Appl. No.: 10/356,040

(22) Filed: Jan. 31, 2003

(65) Prior Publication Data
US 2003/0149389 A1 Aug. 7, 2003

Related U.S. Application Data

(60) Provisional application No. 60/345,551, filed on Jan. 7, 2002, provisional application No. 60/355,550, filed on Feb. 7, 2002.

(51) Int. Cl.
*A61F 13/06* (2006.01)

(52) U.S. Cl. .................. 602/62; 602/61; 602/78
(58) Field of Classification Search .............. 602/41–59, 602/60–79; 604/304–308, 180; 2/125, 126, 2/311, 338
See application file for complete search history.

(56) References Cited

U.S. PATENT DOCUMENTS

| | | | | |
|---|---|---|---|---|
| 4,085,872 A | * | 4/1978 | Foo | 224/602 |
| 5,328,446 A | * | 7/1994 | Bunnell et al. | 602/16 |
| 5,338,290 A | * | 8/1994 | Aboud | 602/75 |
| 5,514,155 A | * | 5/1996 | Daneshvar | 606/201 |
| 5,779,657 A | * | 7/1998 | Daneshvar | 602/60 |

* cited by examiner

*Primary Examiner* — Patricia M Bianco

(57) ABSTRACT

A joint is created by stretching stretchable material and detachably/re-attachably attaching the stretched material to an attachment means such as a piece of hook-type fastener. The joint can be used in wraps for wounds, with or without supports.

20 Claims, 43 Drawing Sheets

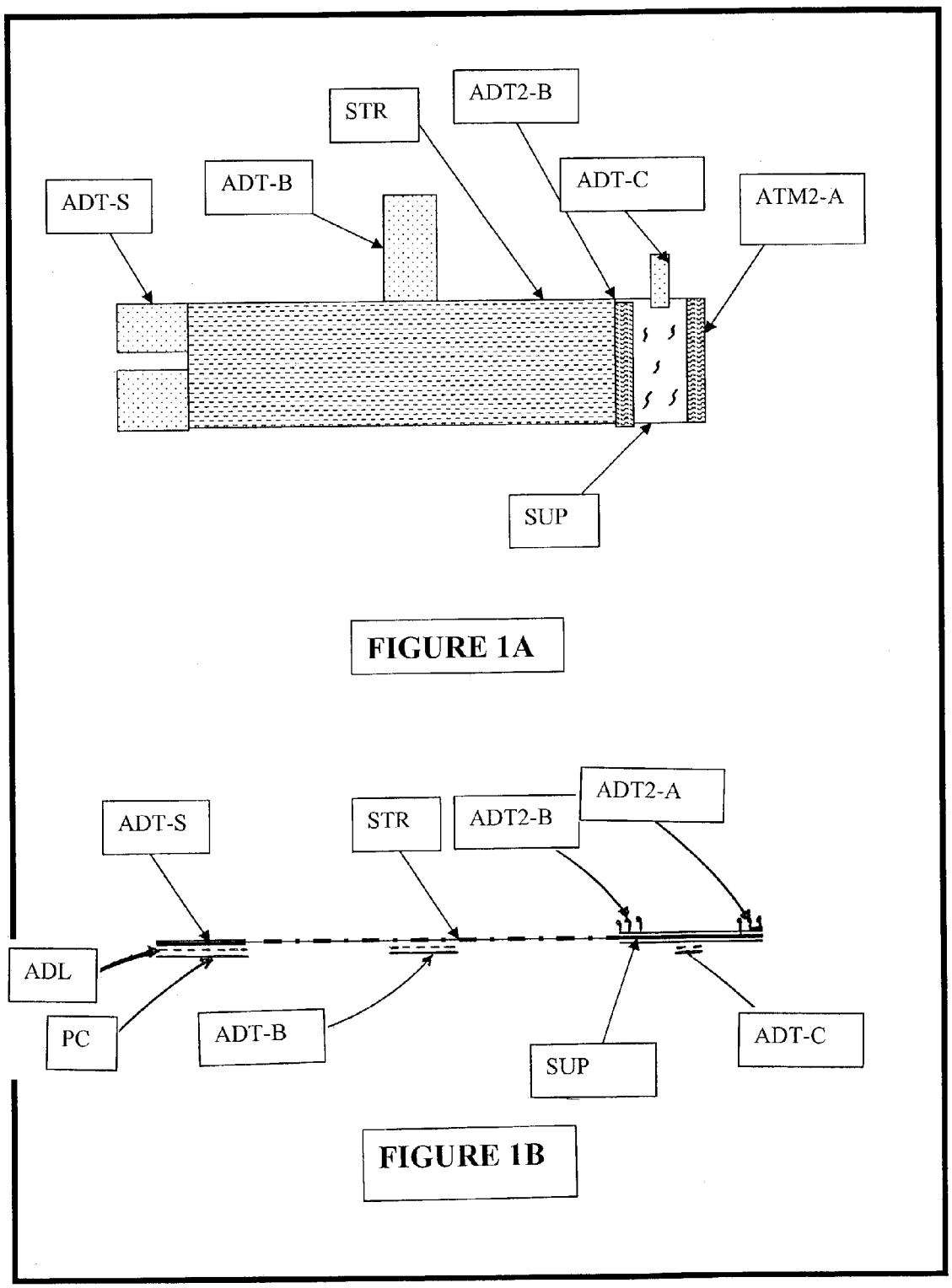

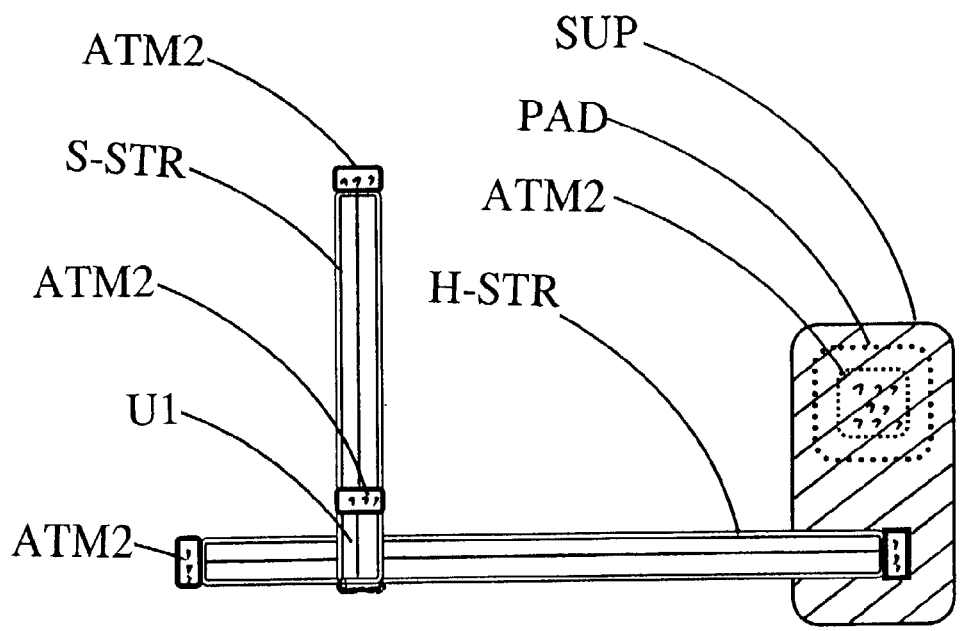
Figure 30
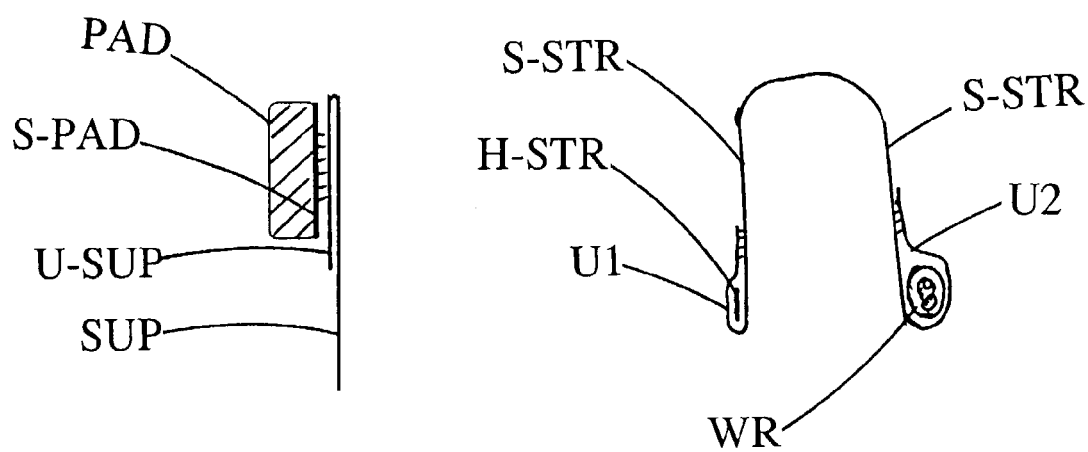
Figure 31
Figure 31A

DANESHVAR WOUND DRESSING, SUPPORT UNITS AND METHODS, MODEL JASMINE

This is a regular application requesting the priority of the following provisional applications: Filing No. 60/345551, filing date Jan. 7, 2002 and Filing No. 60/355550, filing date Feb. 7, 2002.

I claim the benefit of the earlier US Provisional application with filing No. 60/345551, filing date Jan. 7, 2002 with the invention title: DANESHVAR'S WOUND DRESSING UNITS AND METHODS. (This is now presented to USPTO as a regular application).

I also claim the benefit of the earlier U.S. Provisional application with filing No. 60/355550, filing date Feb. 7, 2002 with the title of invention: DANESHVAR'S WOUND CARE DRESSING UNITS AND METHODS.

THE BACKGROUND OF THIS INVENTION

This invention is related to wound dressings and supports in humans and animals. Commonly, adhesives and wraps are used for this purpose. However, the use of adhesives has multiple problems: they are difficult to use with elastic gloves since adhesive tapes adhere to the gloves, they cause skin irritations and discomfort on removal, and do not adhere to hair-covered skin. Many times the hair has to be shaved, which is a separate process of its own. Wound inspections or the exchange of dressing multiplies their problems and prohibits this process. Furthermore, wound wrapping cannot be done through use of adhesive tapes in an effective and convenient method. Then, there is the major issue of dressing a wound with one hand, which is crucial in certain circumstances. It thus becomes very important for a wound dressing system to allow a person to dress a wound with one hand only, since the other one could be wounded or disfunctional. Lastly, at times wound dressing should be done as quickly as possible, and speed makes a big difference in manmade or natural disasters. The methods and means introduced in this application solve many of these problems. Wound protection and prevention of limb damages are also important issues and need new approaches. In some cases the wound site needs to be protected from objects touching the skin or the wound site, to prevent ulceration, avoid discomfort or mere protection of the wounds.

Healing complicated wounds such as swollen areas due to a compromised circulation, which leaves tissues filled with extravasated fluids, is complicated and many times unsuccessful. Therefore, new approaches that allow a better drainage of the tissues are introduced in this application.

THE BRIEF EXPLANATION OF THE INVENTION

This application introduces new methods and means of dressings that make the process of wound dressing faster and easier and applicable with one hand. It practically eliminates the use of adhesives tapes on skin and/or decreases their use substantially. In the prototype model, a combination of a strap and a support unit is used combined with bands to facilitate the placement of the unit. The support unit is made from a non-stretchable material, commonly in rectangular-or trapezoid-shape, and it is used to cover the wound and hold the gauze pad or wound dressing in place. This unit also uses at least one strap made of a particular stretchable material that allows the strap to attach to the support on a detachable, re-attachable basis. Very importantly, the attachment of the strap to a hook-fastener can be done in any part of the surface of this strap. Importantly also, this support system uses one or two narrow bands made from the same material as the strap, which facilitate the placement of the unit and provide many benefit such as placement of the supports with one hand. In one model these bands wrap around the limb from the opposite side of the strap to attach to the support on a detachable, re-attachable basis. Then the main strap will attach to the support on detachable, re-attachable basis. In some models the support unit will function as the stabilizer of the system or to make the functions simpler and easier. This main idea, then, is used to make multiple models for use in different areas. These include a unit to control bleeding by strangulation of the limbs, as well as introducing units that guard the wound site and prevent objects from touching the skin or the wound site to avoid discomfort or mere protection of the wounds. Also, means are introduced that help in preventing ulcerations in areas such as the heels. In patients with vascular problems the models shown here allow the wound in the heels to be squeezed to prevent and reduce tissue swelling. In other cases, the applicant shows means that allow a limb to be elevated for a better drainage. All in all, the applicant tries to introduce units for helping the human's and animal's life be better.

Please note that in this application the hook- and loop-fastener attachment means are utilized very frequently, and in general:
a. The loop-fastener attachment means is referred to as ATM1
b. The hook-fastener attachment means is referred to as ATM2

Please note that any other types of attachment means may be also used in these units if possible.

Also please note that each wound support unit in this application uses a support piece or means and that these support means are basically of two types:
a. Type I support means are made from a non-stretchable layer such as vinyl whose body has zones of attachment means on it.
b. Type II support means is made from a non-stretchable layer with a laminated body; an outer layer made from a layer of loop-fastener attachment means, ATM1, an inner layer which is a soft, fabric lining upon skin contact and a layer of foam in between.

Please note that the Type II support means may also have zones of hook-fastener attachment means, ATM2, on them. This makes a very particular unit that allows the attachment of a strap made from a loop-fastener attachment means, ATM1, with end pieces or zones of hook-fastener attachment means, ATM2, to occur on a double-function as follows:

1. The zones of the hook-fastener attachment means, ATM2, from the ends of the strap will attach to the outer surface of the Type II support on a detachable, re-attachable basis.
2. The body of the strap, made from a loop-fastener attachment means, ATM1, will also attach to the zones of the hook-fastener attachment means, ATM2, on the support on a detachable, re-attachable basis as well. This is the reason why a double-attachment occurs that is very useful in many models of these units.

The figures: Please notice that different parts of this invention are shown in different figures. This is to prevent a crowded picture. Importantly, all of the options are designed to be used in one model if applicable.

adhesive pieces on its right side to allow this unit to be used with one hand only.

Figure 2:
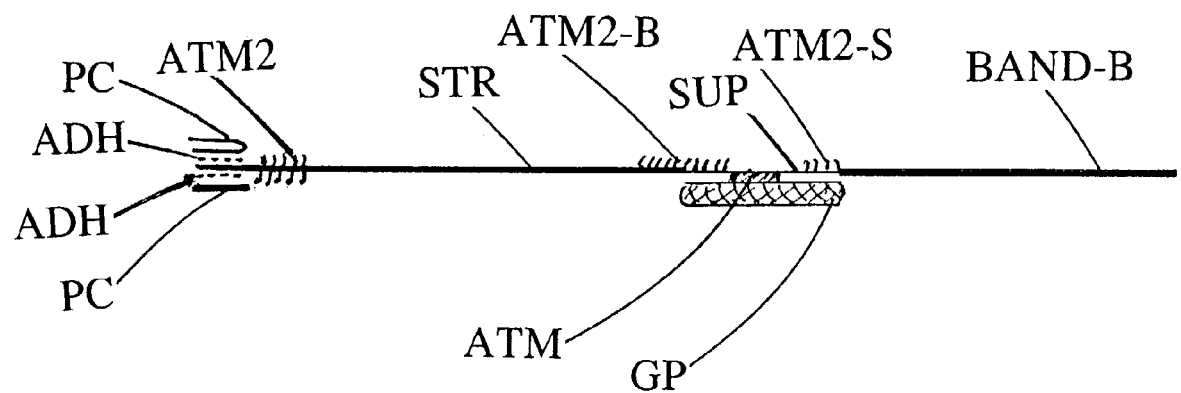

FIG. 2 shows the vertical, cross-cut view of the unit shown in the previous figure.

FIG. 1A shows a wound support with adhesive tapes, ADT-B and ADT-C, for adherence to skin, also the adhesive tape in the left side, ADT-S consists of two pieces.

FIG. 1B shows the side view of the unit shown in FIG. 1A.

Figure 1:
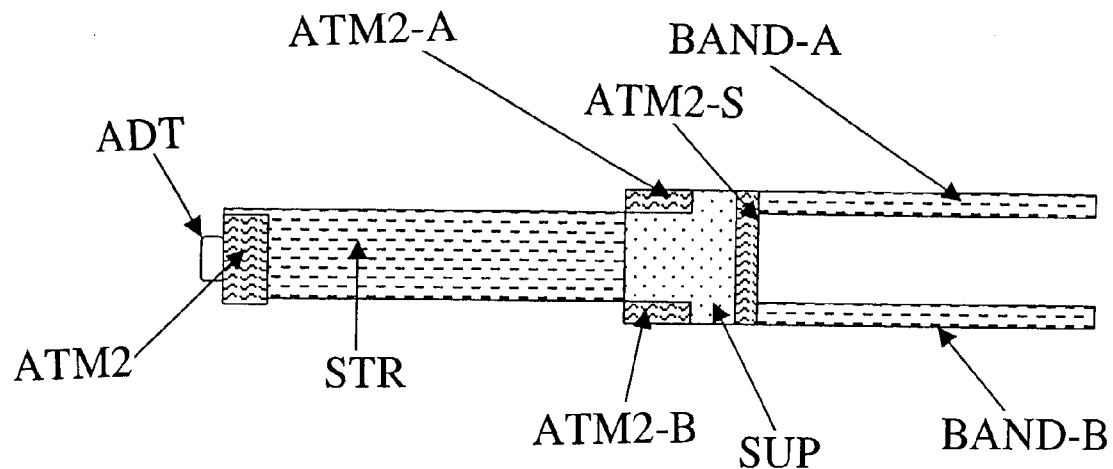
FIG. 1 shows wound support with two bands shown on the right that allows it to be used with one hand.
Figure 1C:
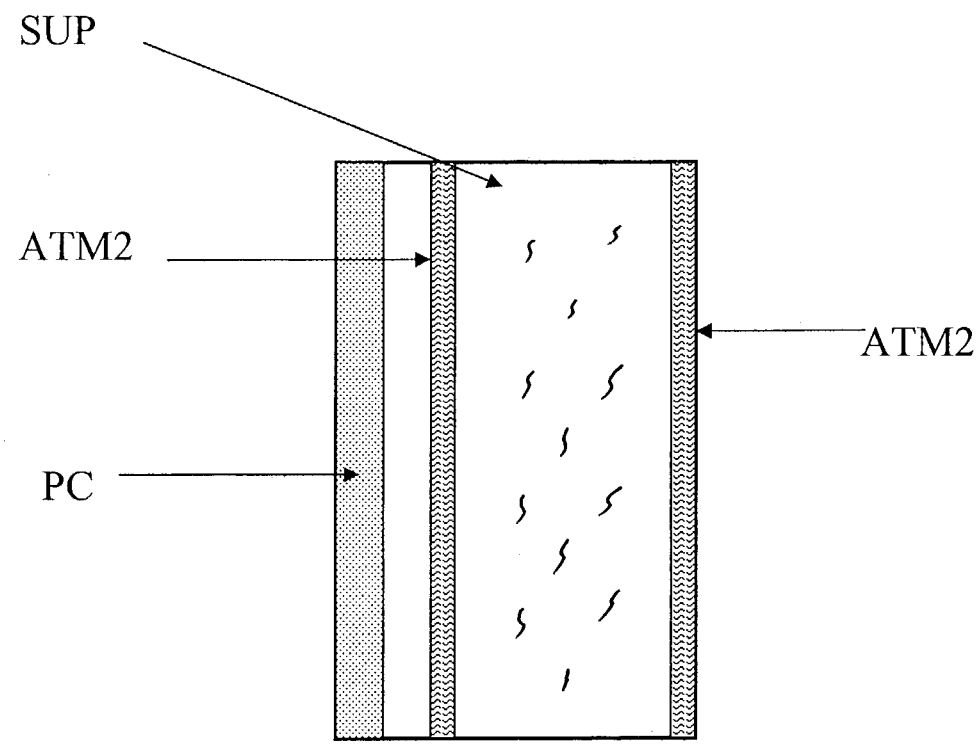

FIG. 1C shows a support with a zone of adhesive under the protective layer, PC, that allows a strap to be attached to it. The rear surface of the support has zones of adhesive.

Figure 1D:
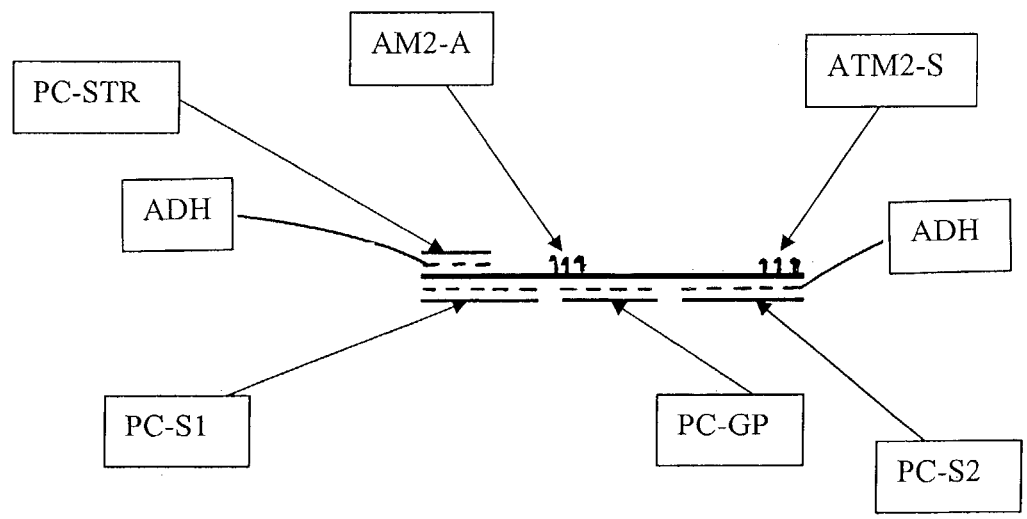
Figure 1C:
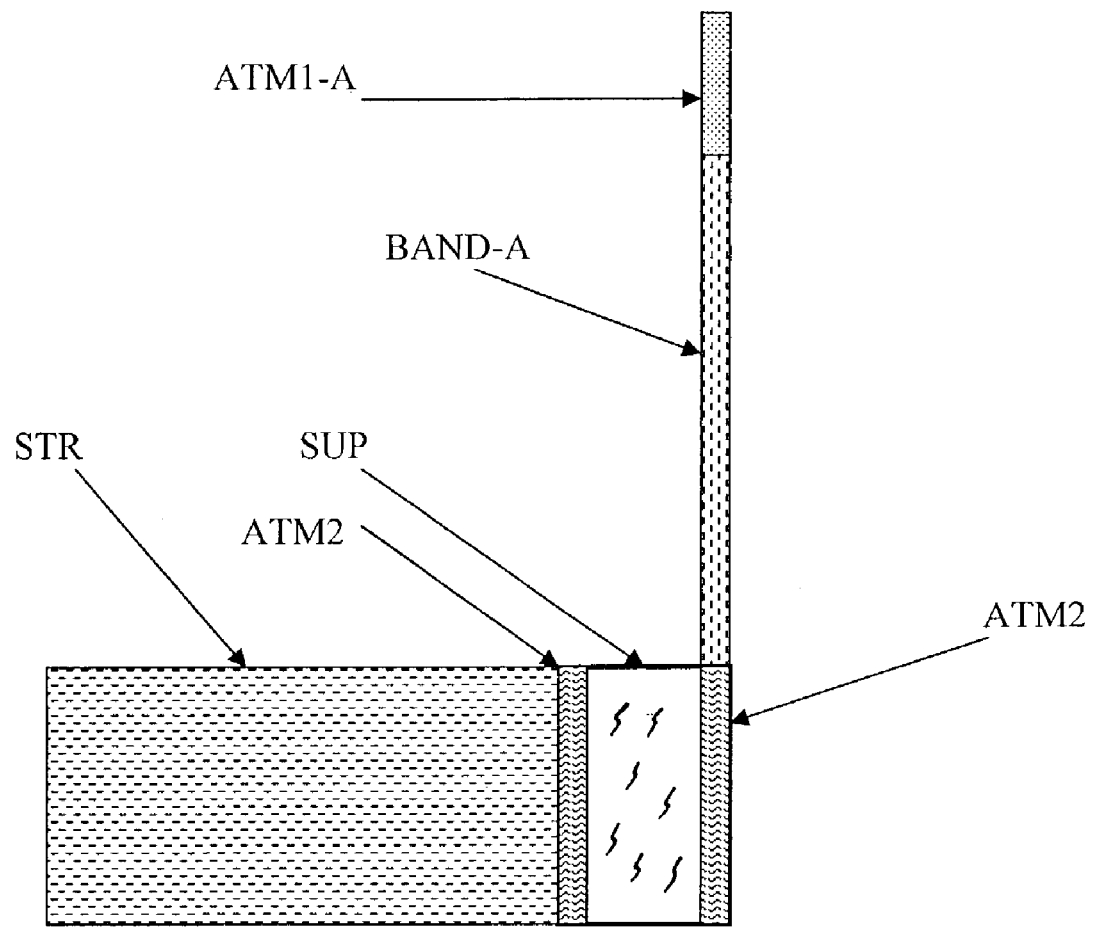

FIG. 1D shows the side view of the unit shown in FIG. 1C and shows the attachment means and adhesives.

FIG. 1CX shows a unit similar to FIG. 1, except that it only has one band, BAND-A attached to the support in different direction.

Figure 1E:
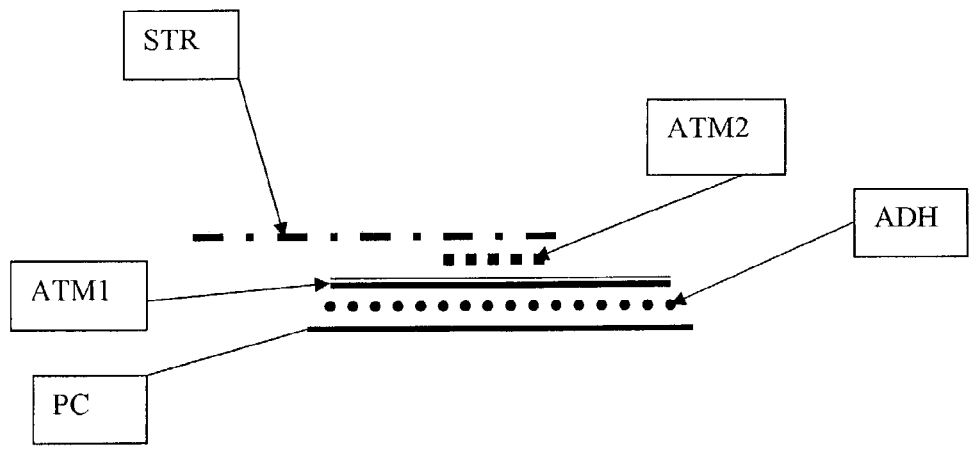

FIG. 1E shows the side view of a strap, STR, with a piece of hook and loop-fastener attachment means, ATM2, ATM1. The lower surface of, ATM1, has a adhesive, ADH that allows it to attach to the surface of the strap in another area.

Figure 1F:
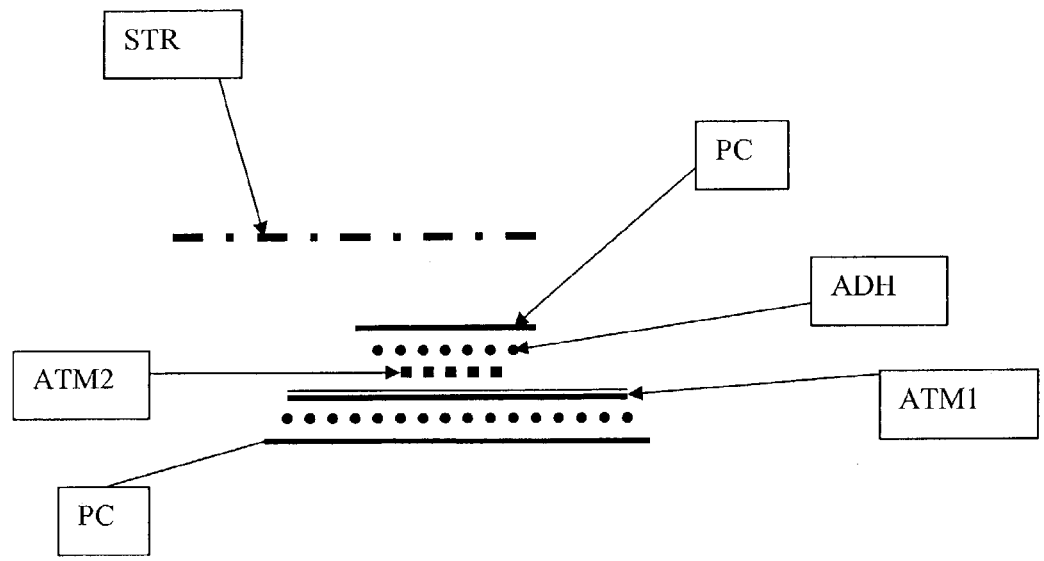

FIG. 1F shows the side view of a unit similar to FIG. 1E, except that this model allows the end of the strap to be attached in any desired area of the support or the strap.

Figure 3:
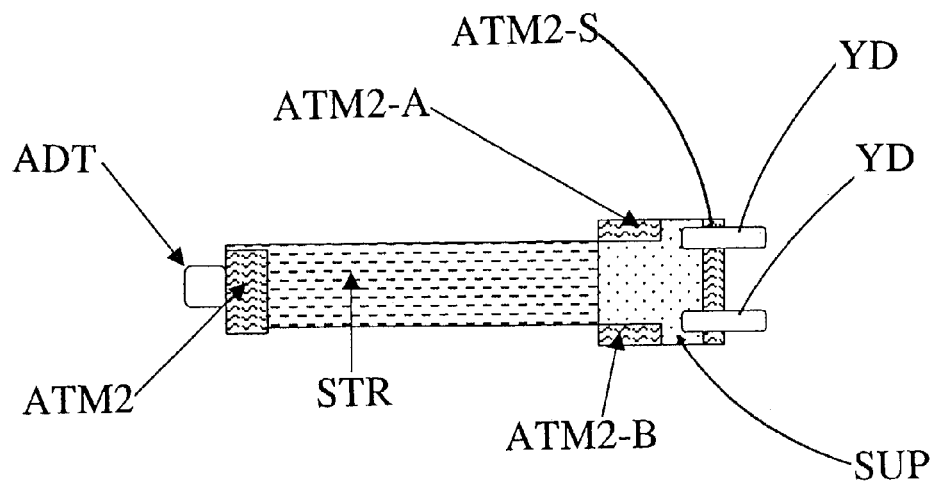

FIG. 3 shows a similar unit as shown at FIG. 1, except this unit uses adhesive pieces, YD, on its right that allow this unit to be used with one hand only.

Figure 4:
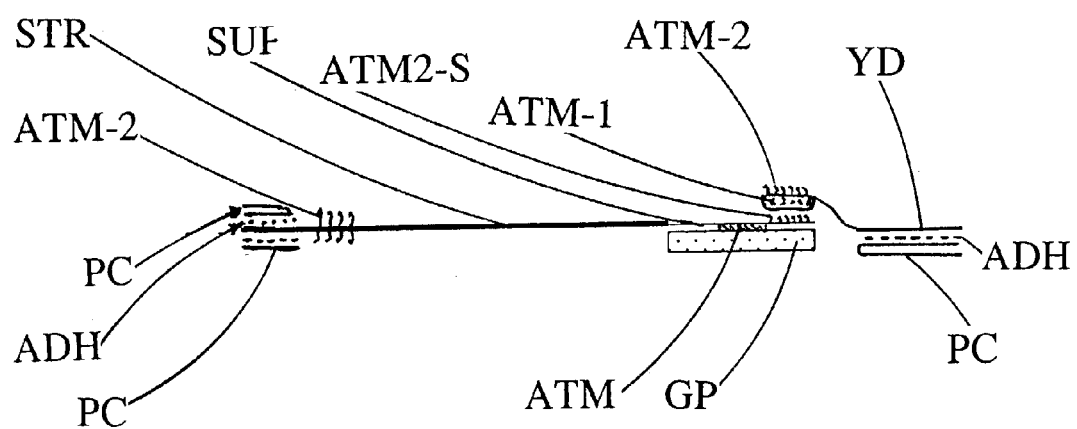

FIG. 4 shows the side view of the unit shown at FIG. 3.

Figure 5:
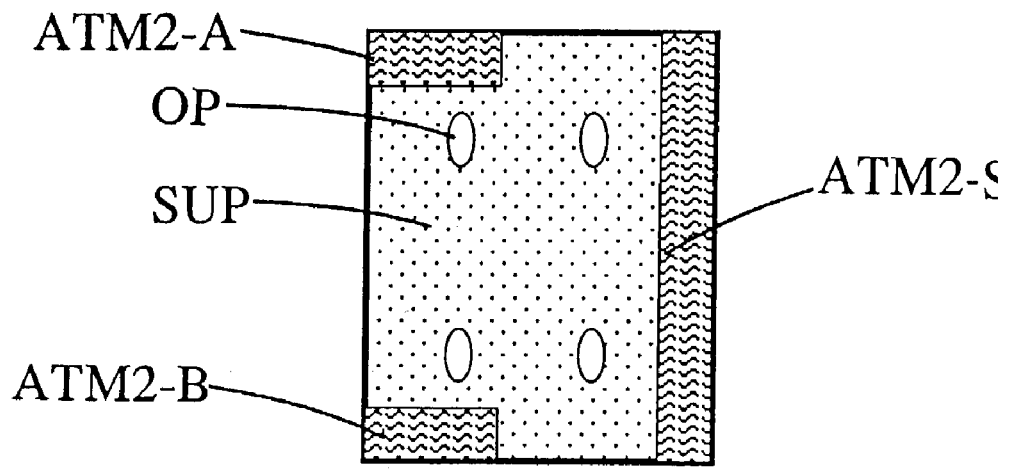

FIG. 5 shows the piece of support from the FIG. 1 in more detail.

Figure 5A:
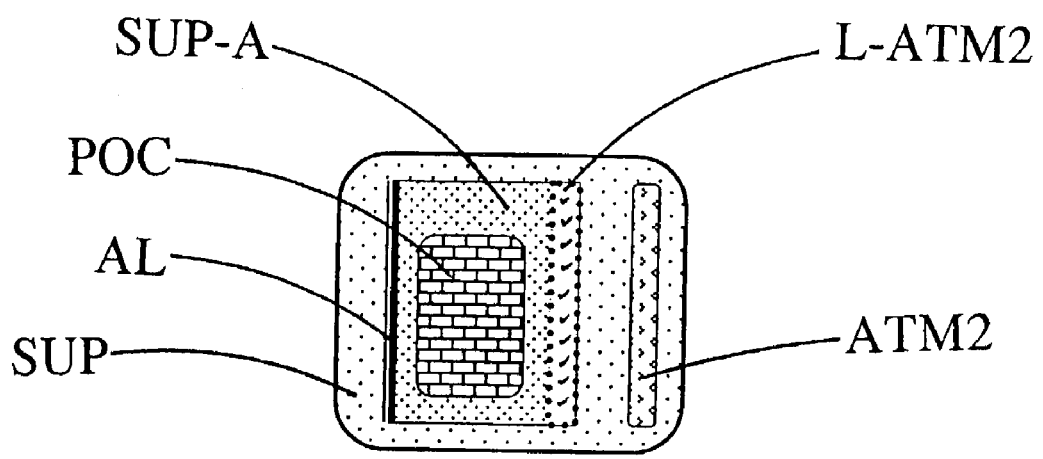

FIG. 5A shows a support piece that has a detachable cover that attaches to it for keeping tubings and wires in between.

Figure 6:
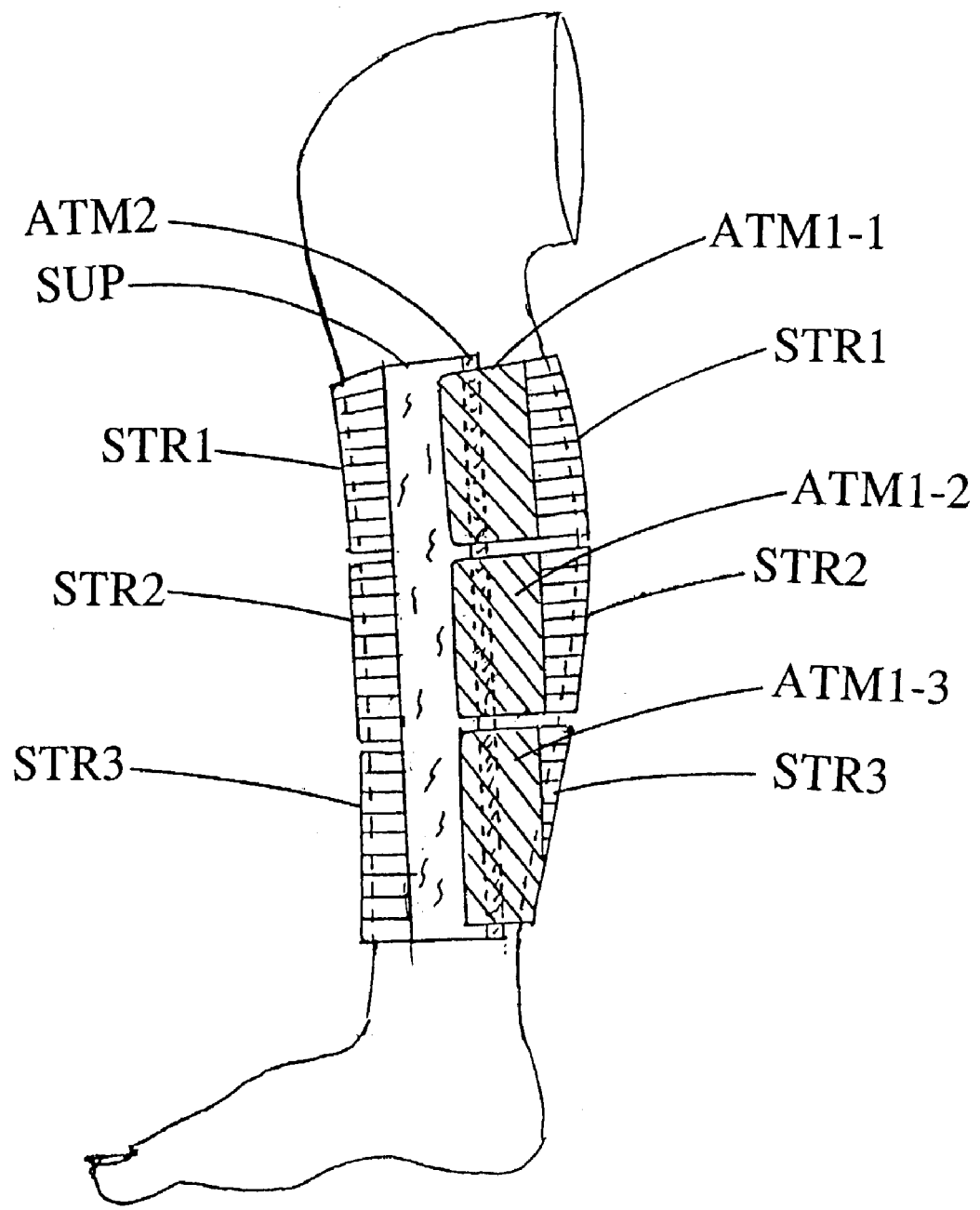

FIG. 6 shows a support unit for the leg, in which one end of the straps is fixed on the border of the support.

Figure 6A:
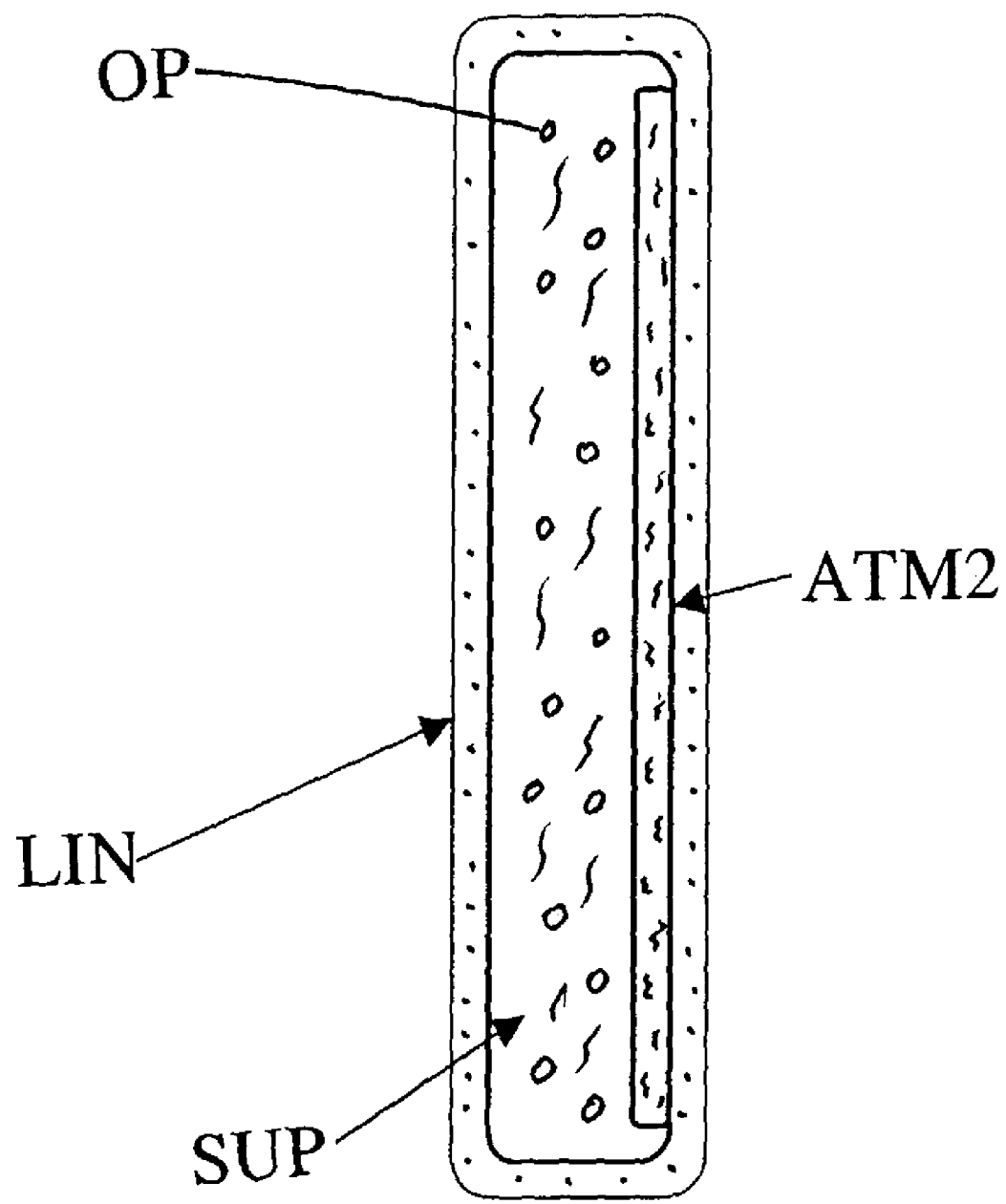

FIG. 6A shows the support piece from FIG. 6 in more detail, with a lining.

Figure 6B:
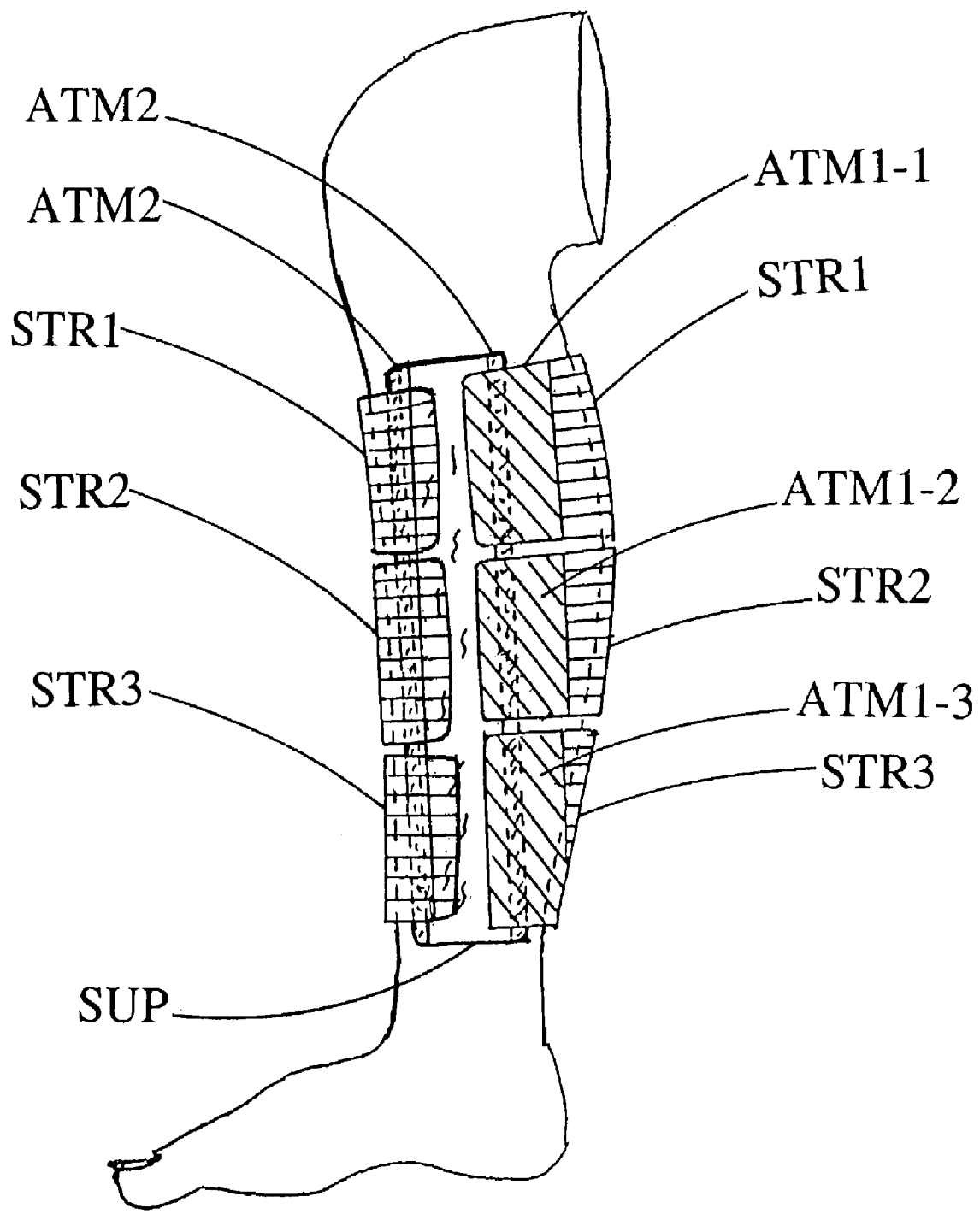

FIG. 6B shows a leg support unit, in which both ends of the straps are attached to the border of the support on a separable basis.

Figure 6C:
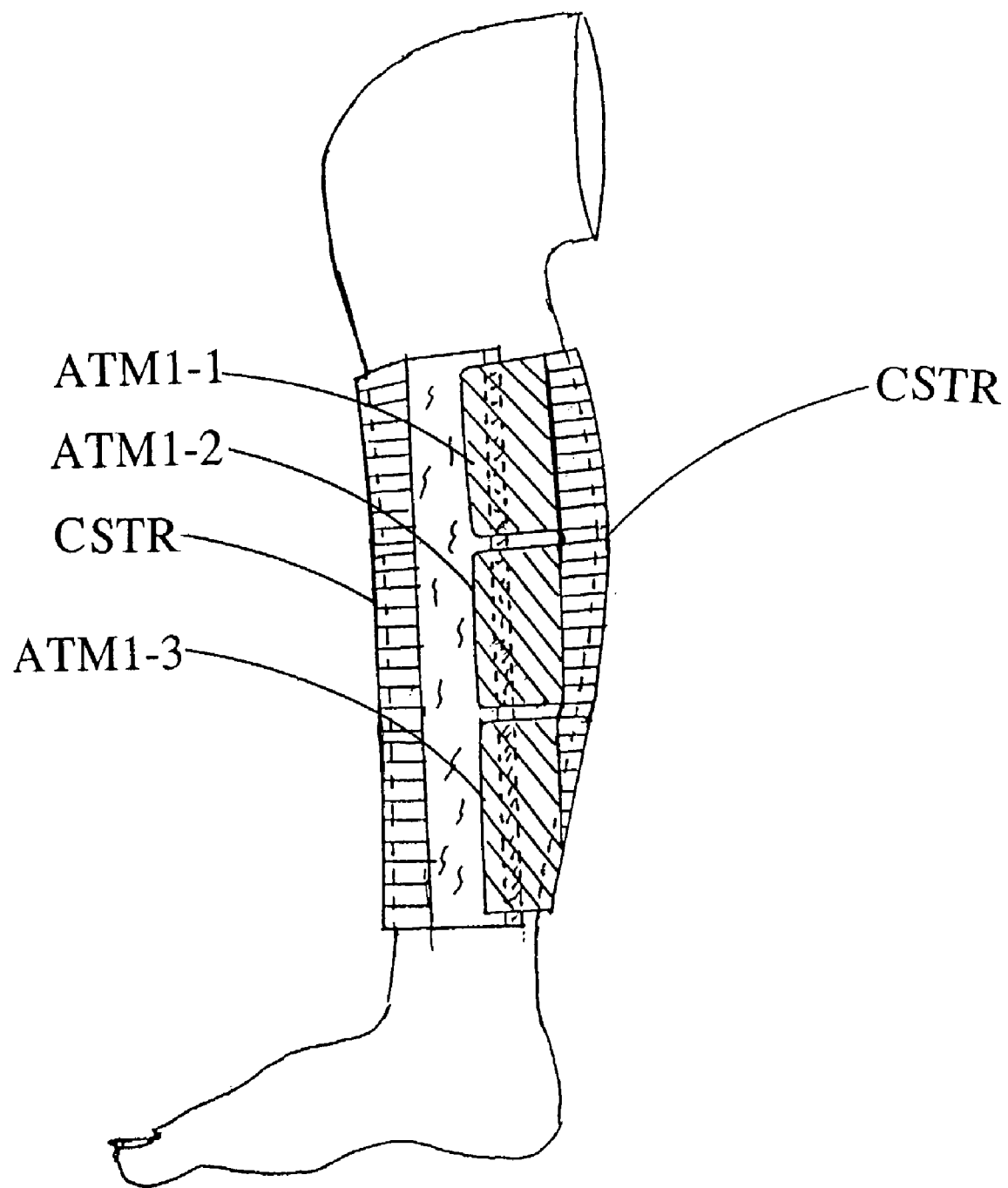

FIG. 6C shows a support unit for the leg, which consists of a single wide strap, CSTR, that has an end with multiple separate attachment means, ATM1, ATM2 AND ATM3.

Figure 7:
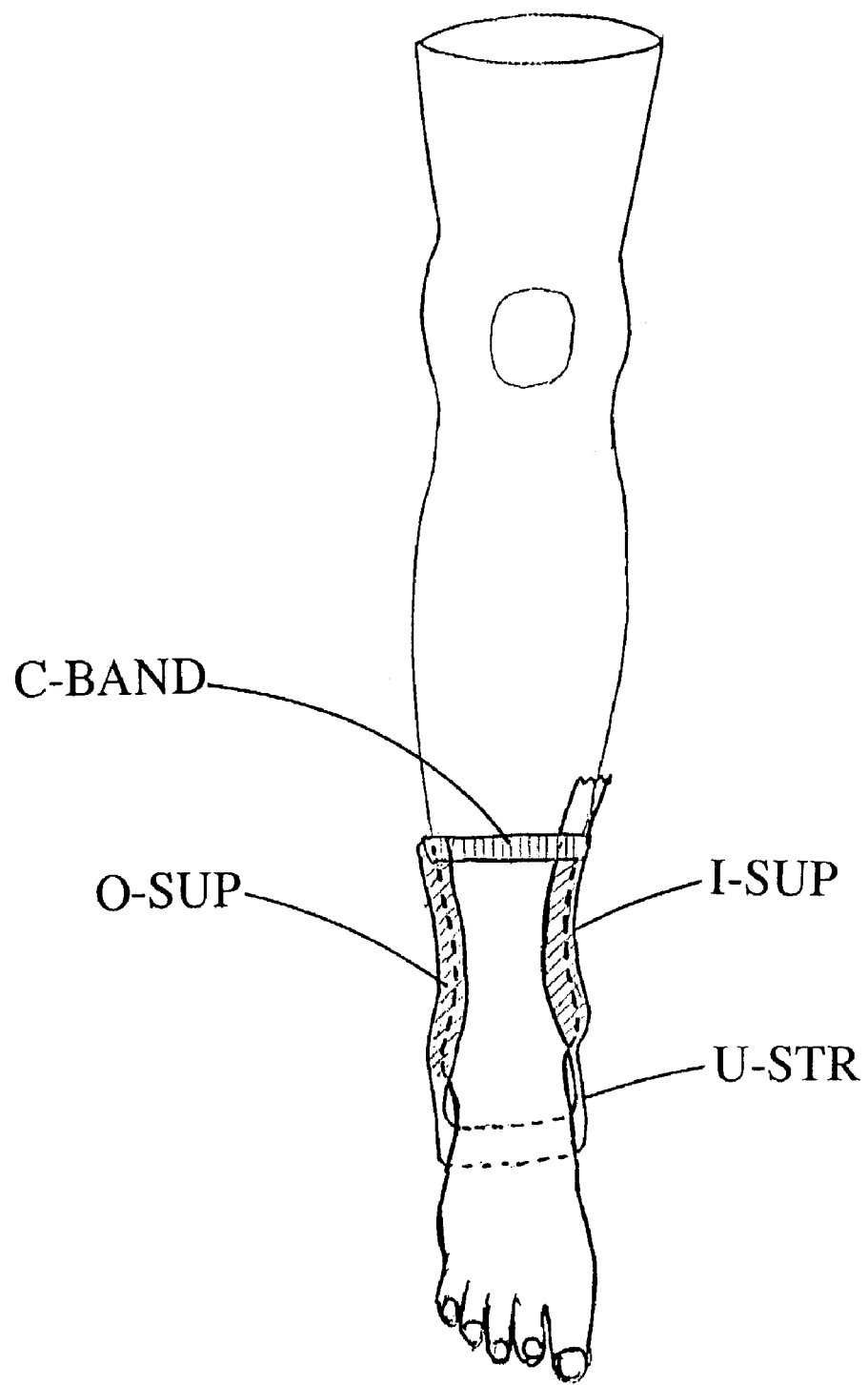

FIG. 7 shows a support unit for the lower leg/ankle area.

Figure 7A:
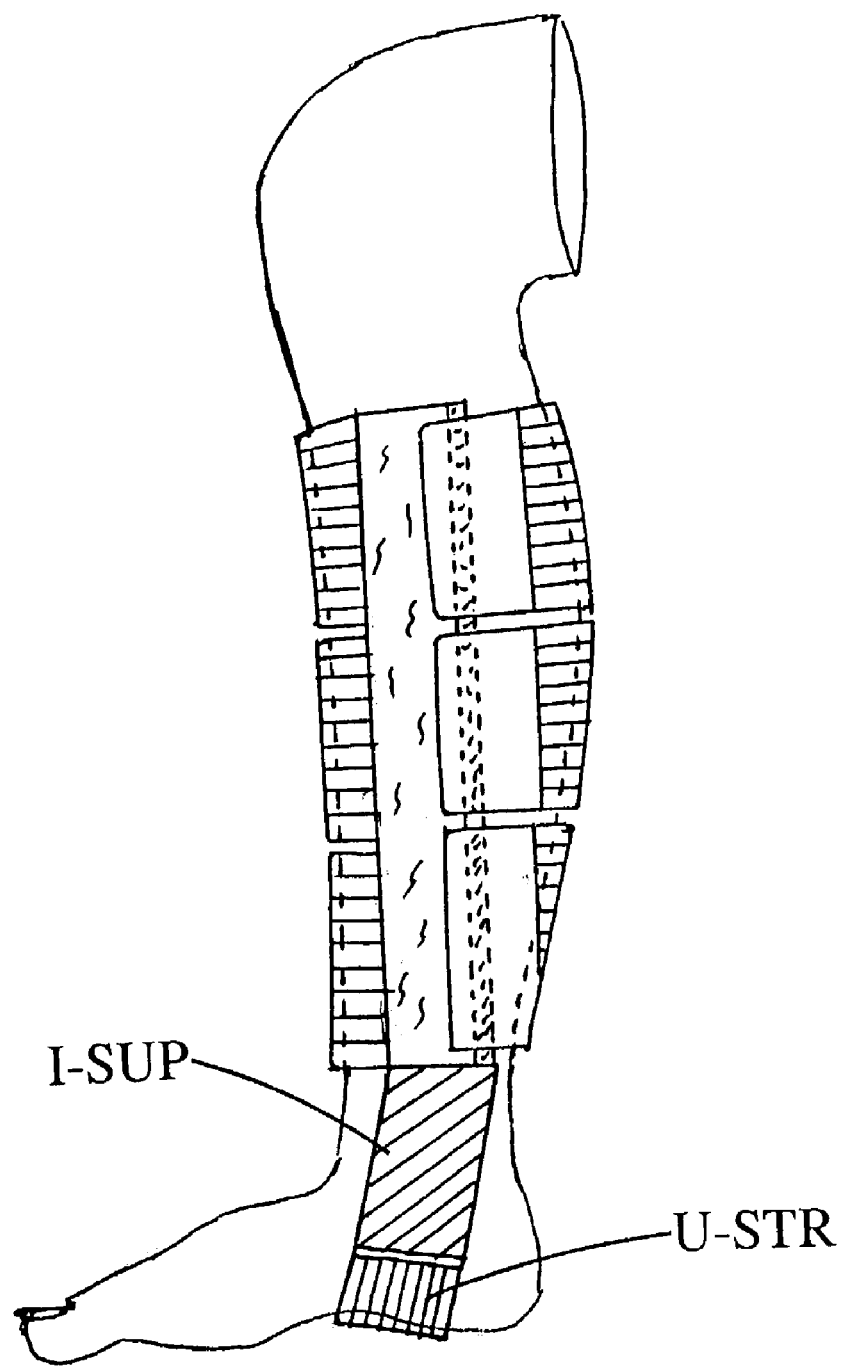

FIG. 7A shows a combination of the units from FIG. 6 with the unit shown at FIG. 7.

Figure 7B:
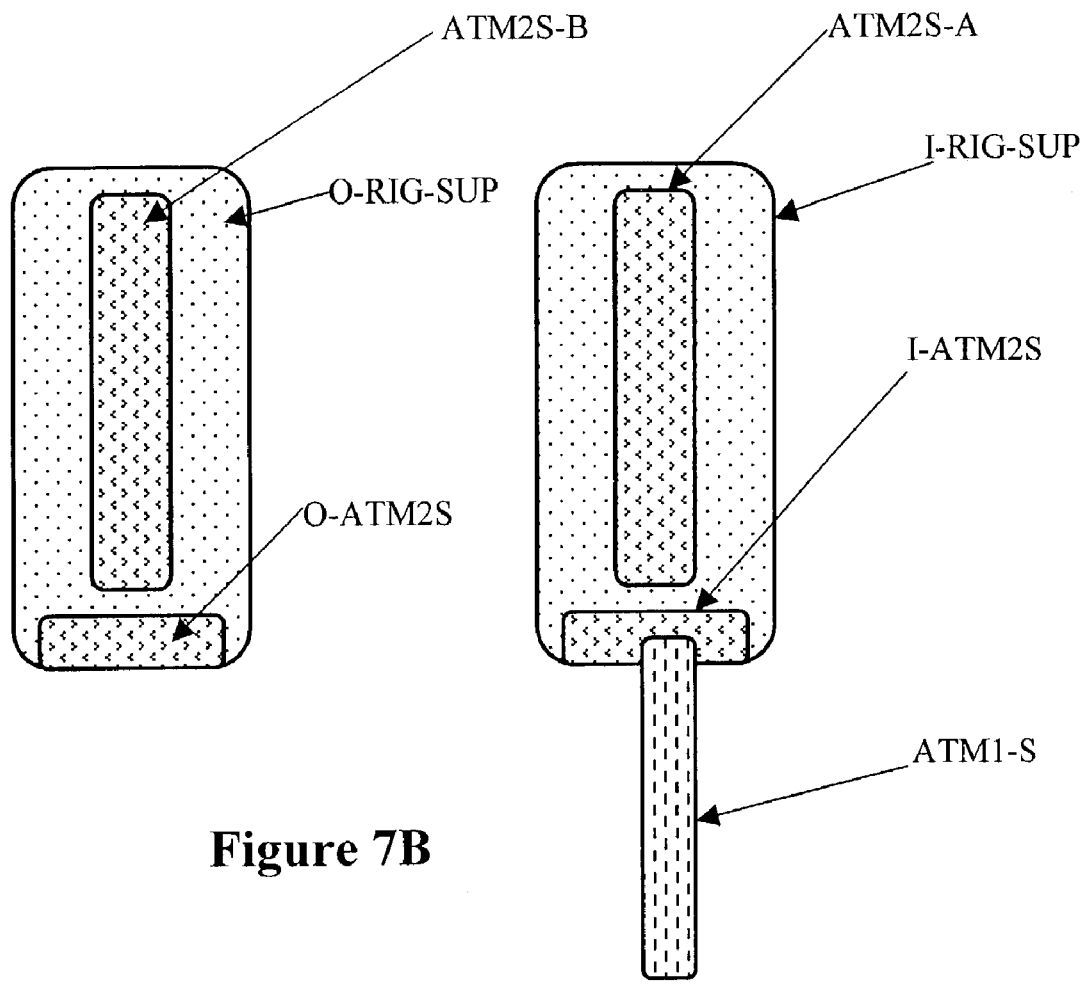

FIG. 7B shows the side views of rather rigid pieces for use with the U-shaped extension for the leg support, designed to allows the compression of ankle.

Figure 7C:
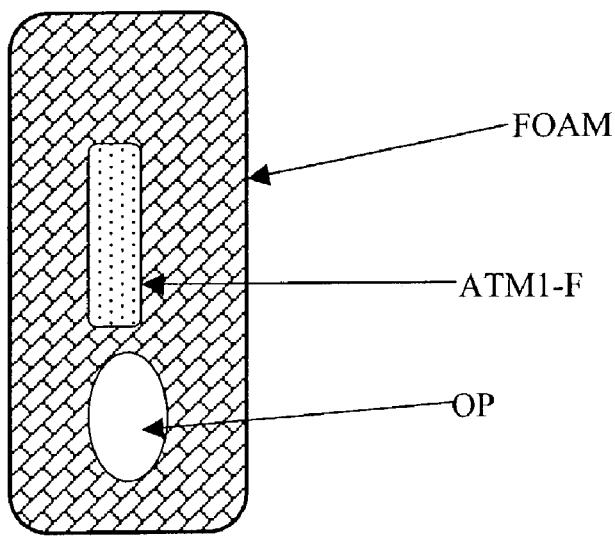

FIG. 7C shows a foam, FOAM, designed for use with the unit shown at previous FIG. 7B.

Figure 7D:
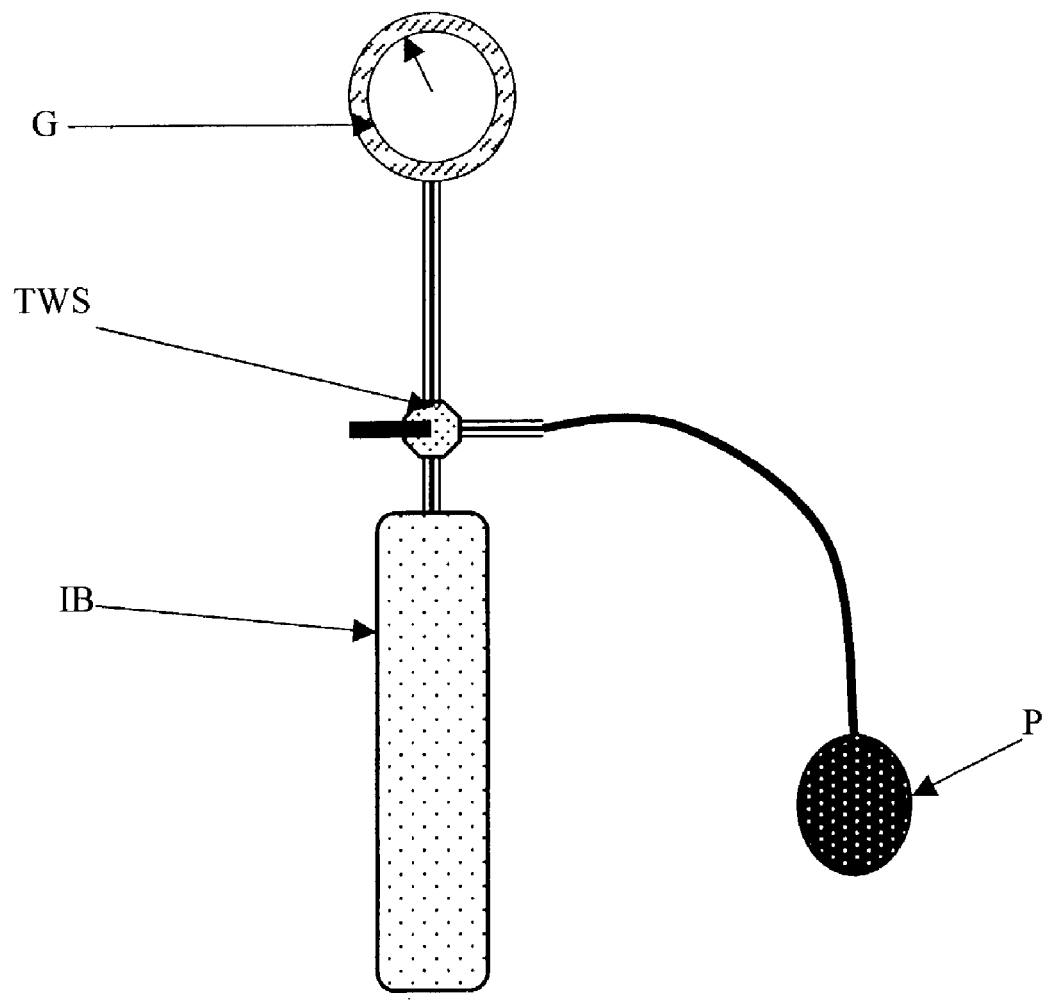

FIG. 7D shows an inflation balloon, IB, with a gauge, G for use with the unit shown at FIG. 7B.

Figure 7E:
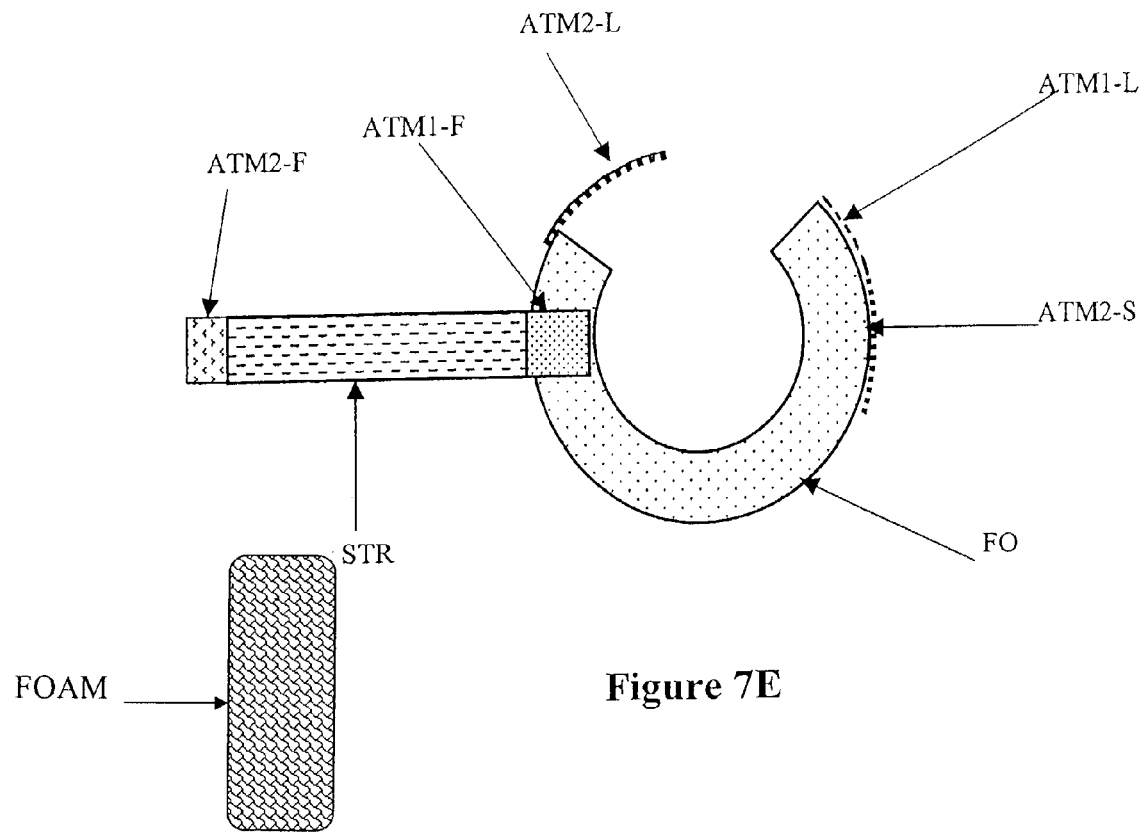

FIG. 7E shows foam pad, FO, with a strap means, STR, that stands on the ankle area and prevents the sides of the ankle and the heel from touching the bed.

Figure 7F:
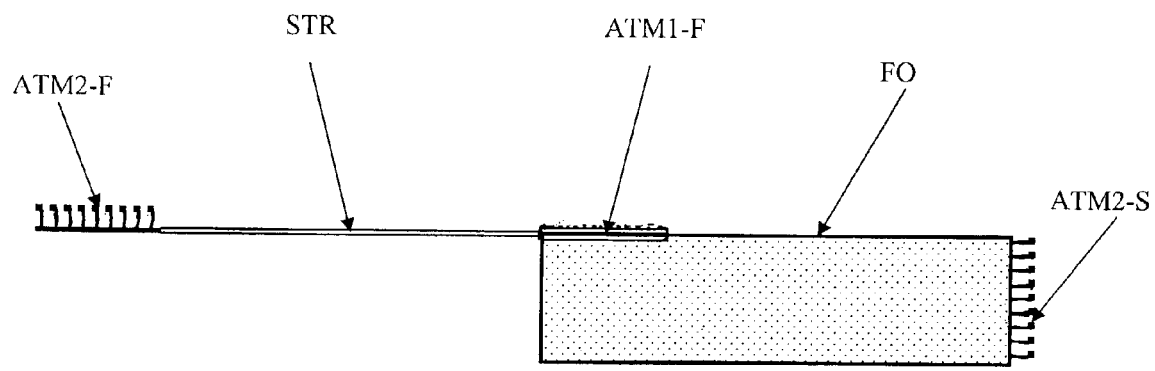

FIG. 7F shows the side view of the foam unit, FO shown at FIG. 7E with the related strap means, STR, attached to its upper left.

Figure 7G:
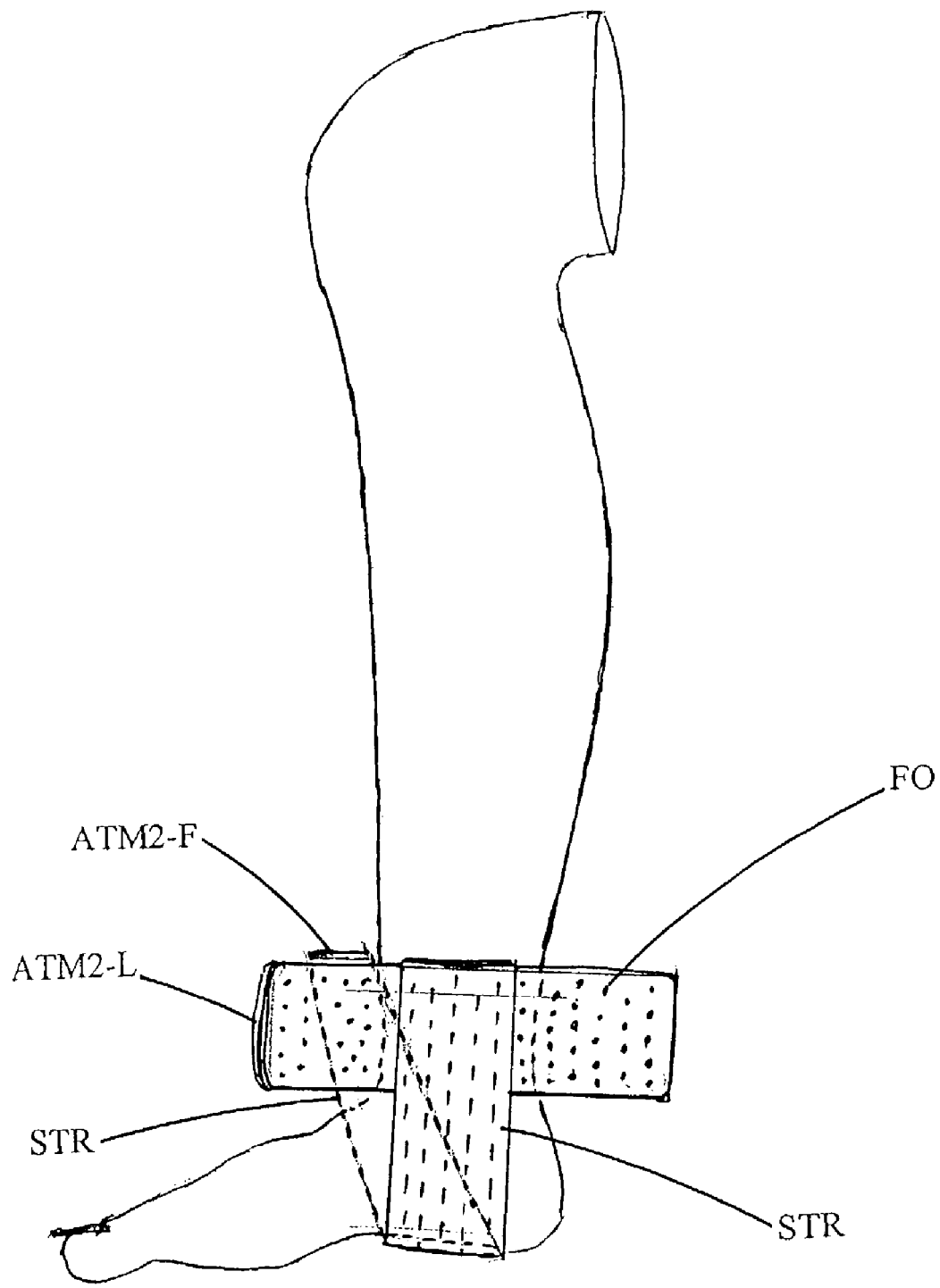

FIG. 7G shows the side view of the foam unit, FO shown at FIG. 7E when placed on a leg.

Figure 8:
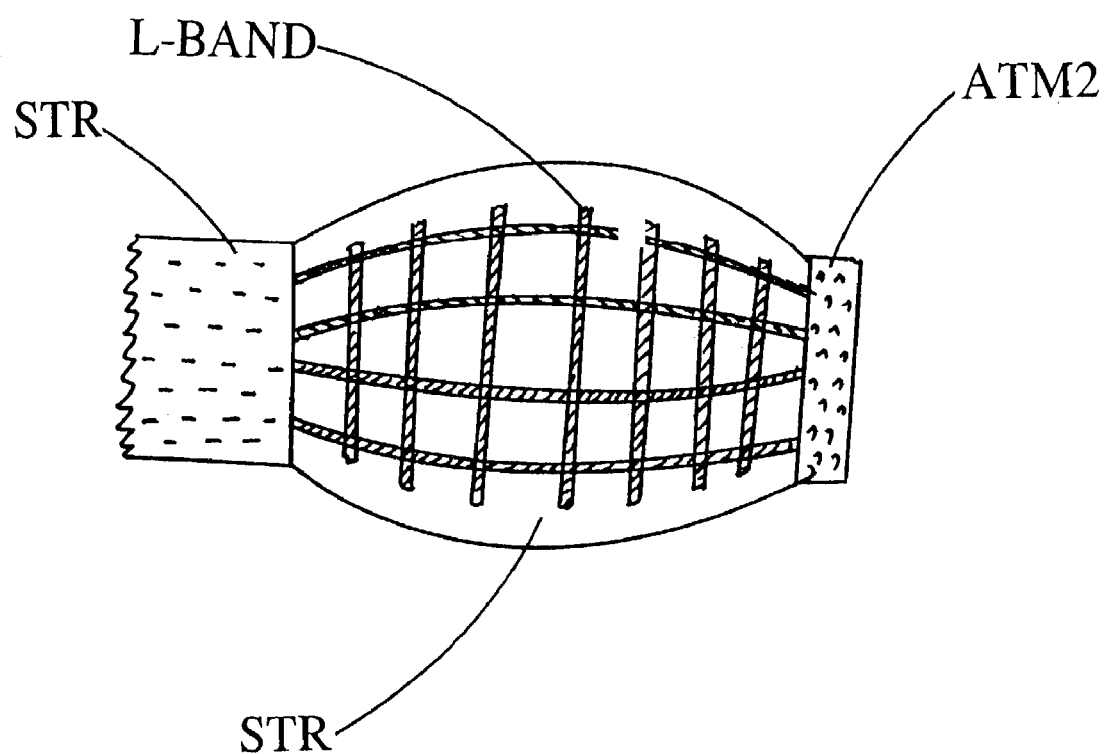

FIG. 8 shows a conformed strap for use in special places such as the knee.

Figure 9:
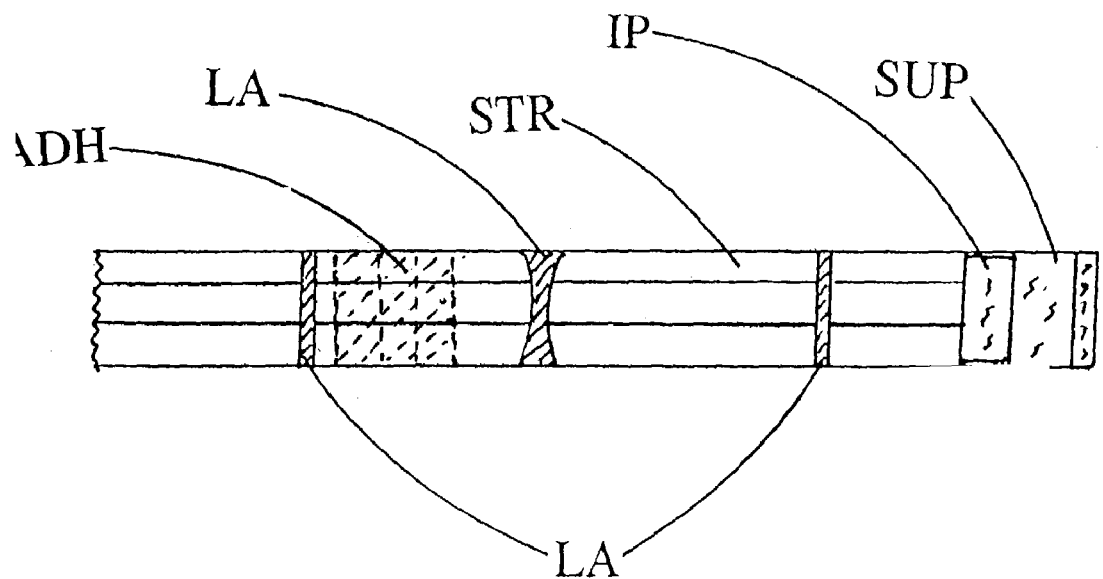

FIG. 9 shows a support unit and a strap where the body of the strap has materials such as latex or shaped means on it, and a zone of adhesive, ADH on its rear surface.

Figure 10:
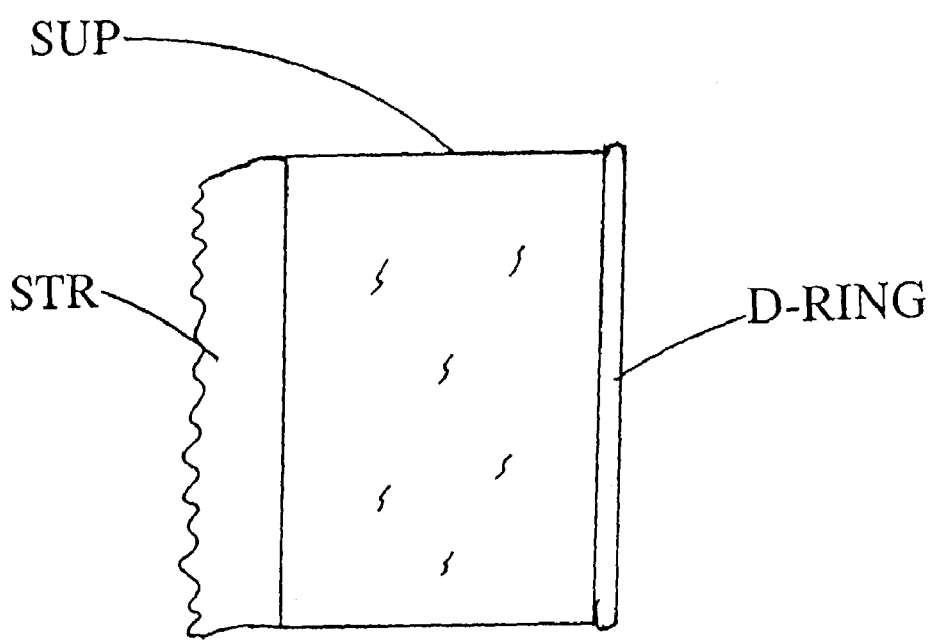

FIG. 10 shows a D-Ring on the side of the support that allow the strap to make a U-turn.

Figure 11:
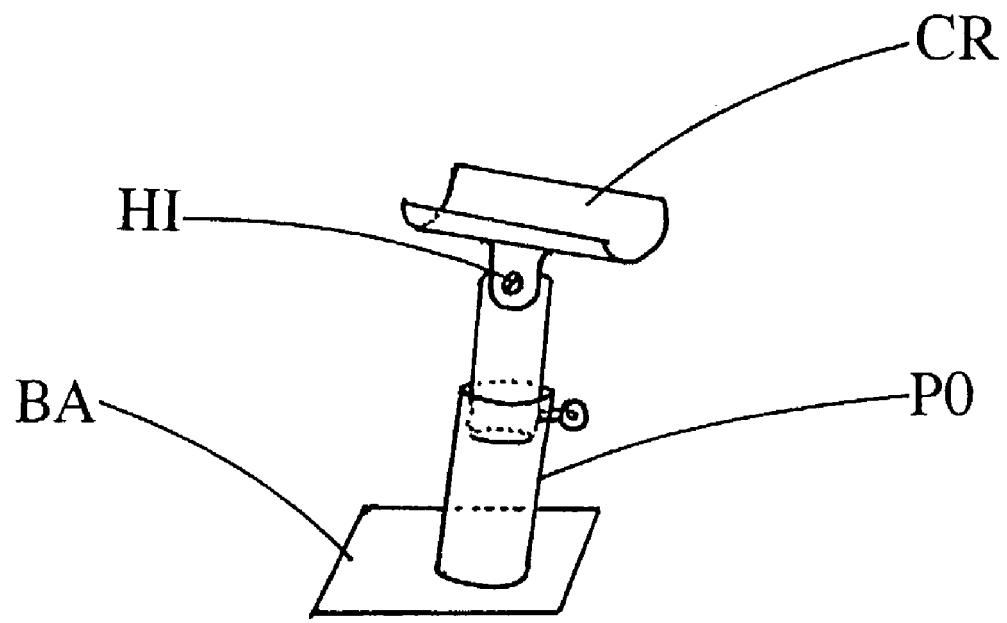

FIG. 11 shows a stand to allow the supports to be placed and used by one hand only.

Figure 12:
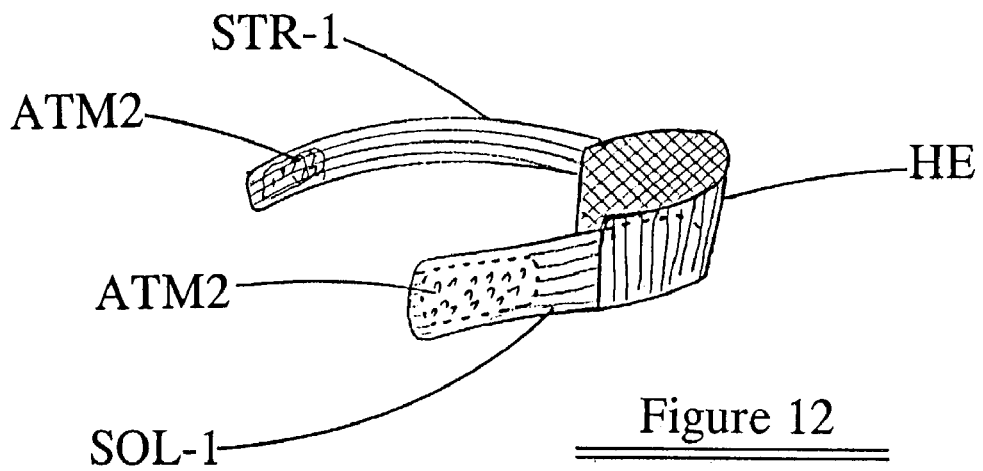

FIG. 12 shows a support for the heel.

Figure 13:
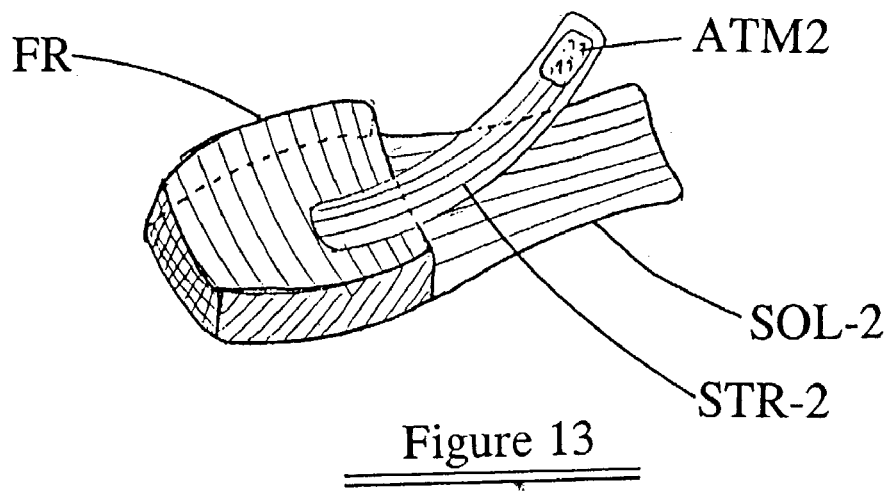

FIG. 13 shows a support piece for the front of the foot.

Figure 14:
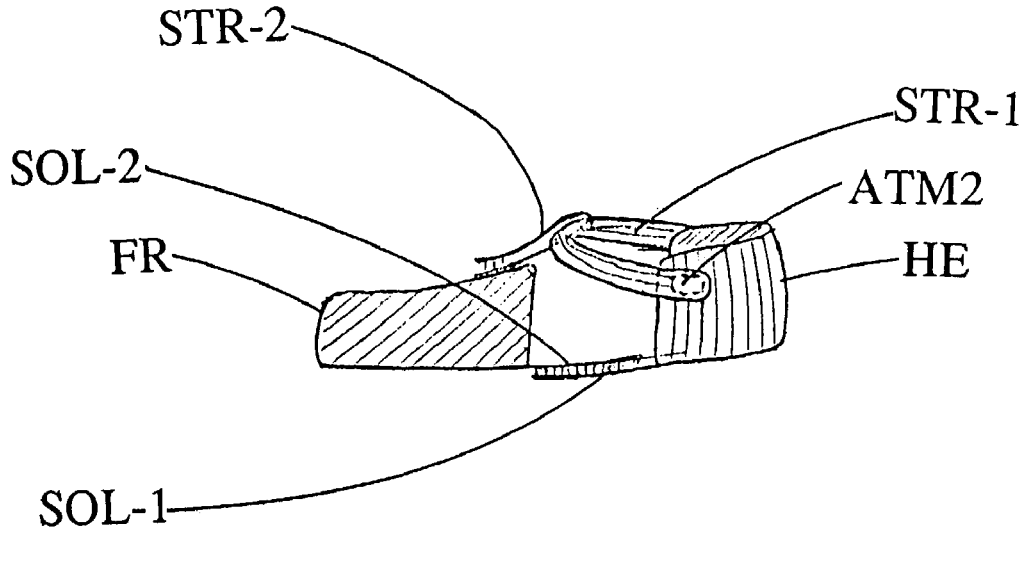

FIG. 14 shows a combination of the units shown at FIGS. 12 and 13.

Figure 15:
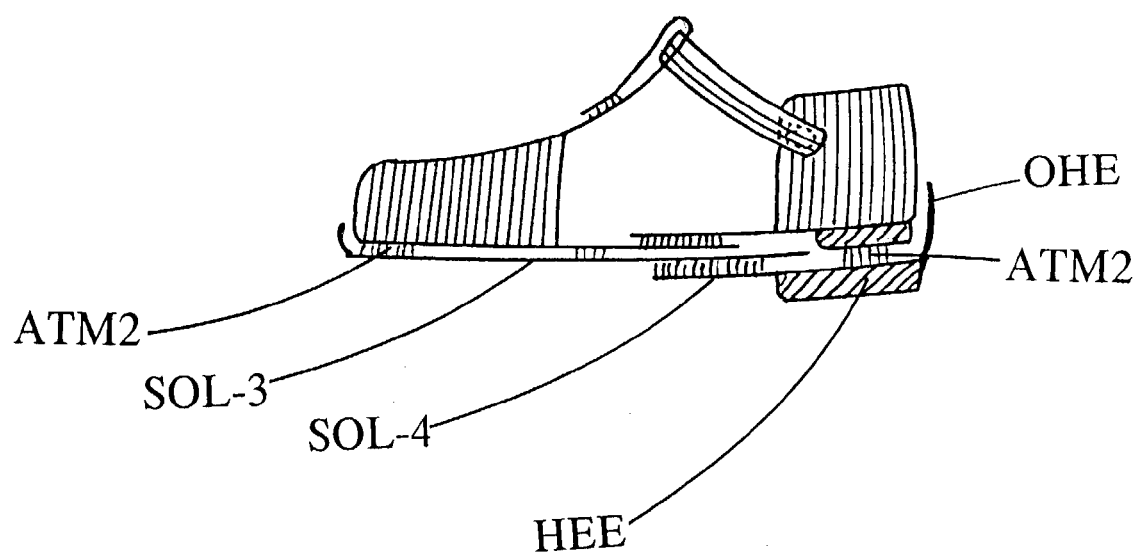

FIG. 15 shows a unit to be used as an adjustable outer cover for the unit shown at FIG. 14.

Figure 15A:
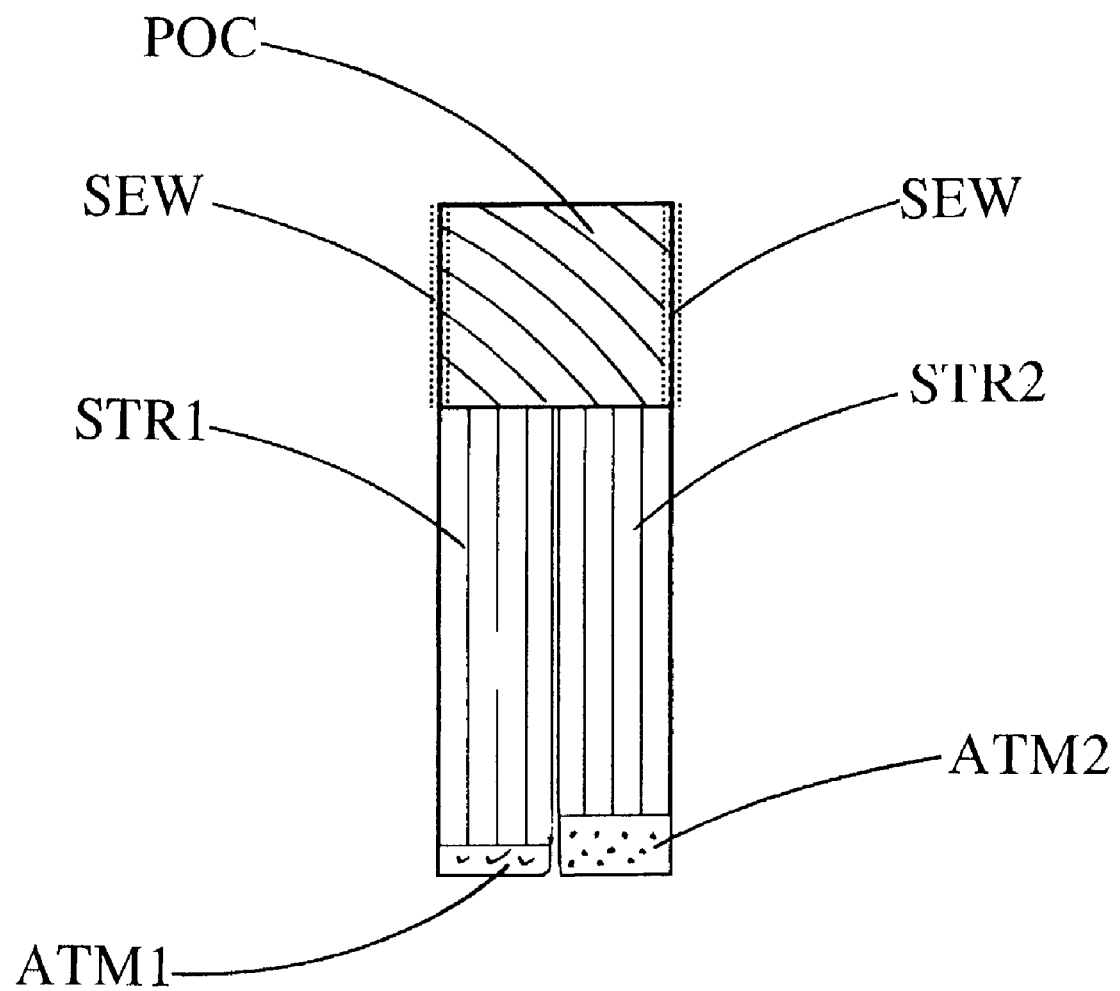
Figure 15:
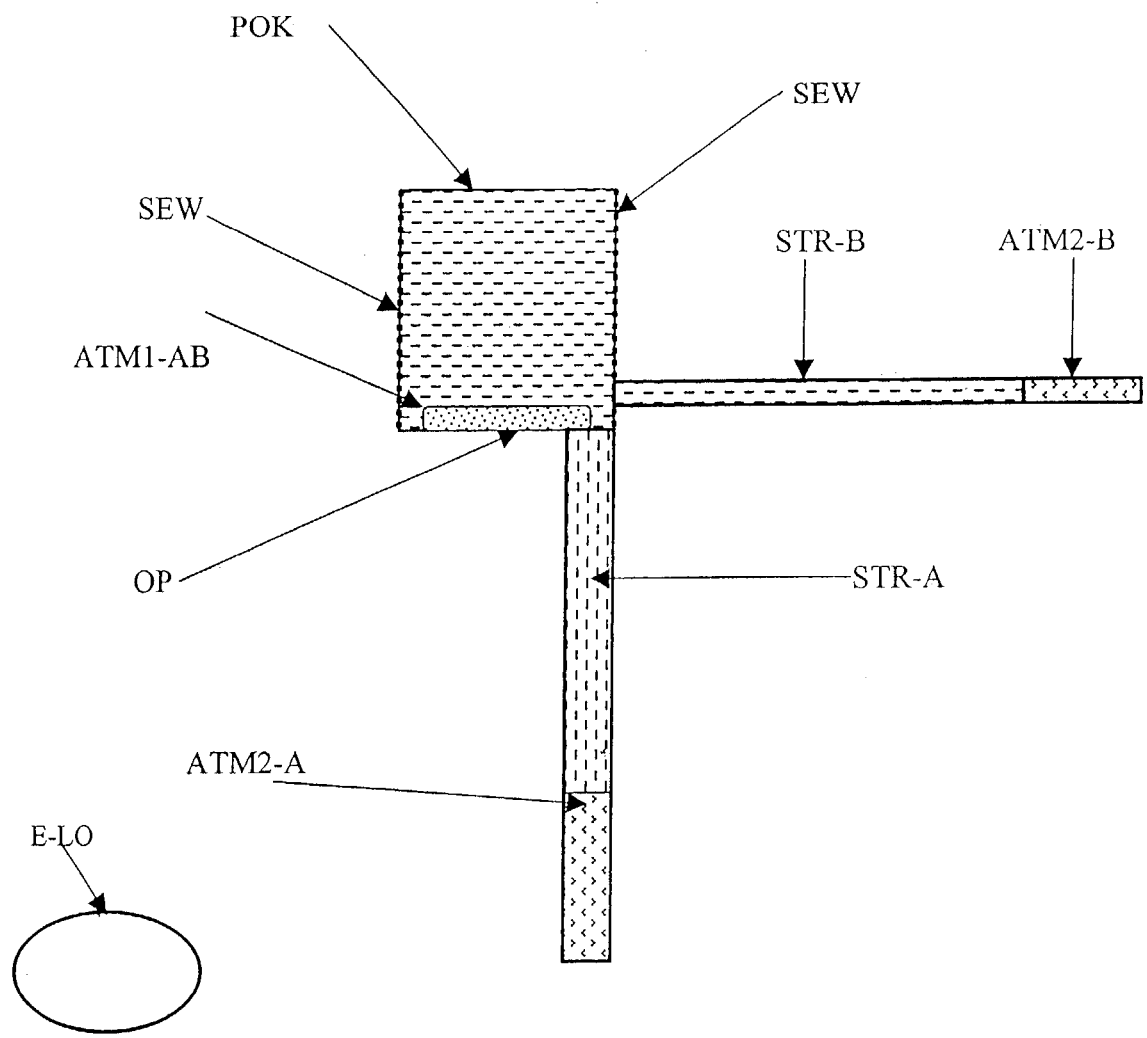

FIG. 15A shows a support unit for the front of the foot.

FIG. 15B shows a modified model of the unit shown previously in FIG. 15A, which has two straps attached in a different arrangement.

Figure 16:
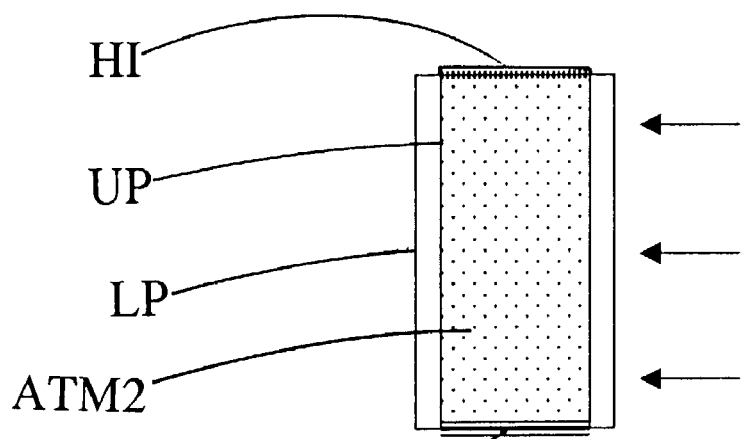

FIG. 16 shows the top view of a buckle system that allow the length of the strap to be adjusted.

Figure 17:
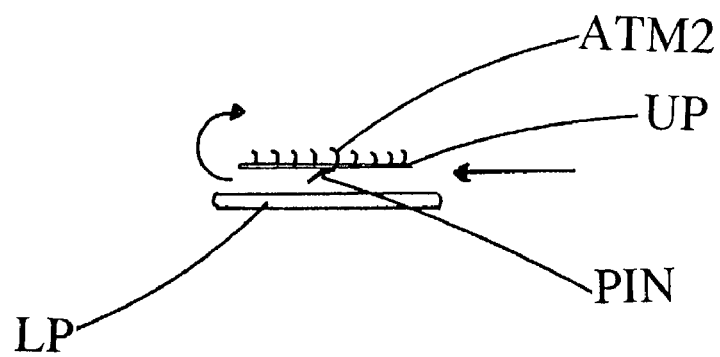

FIG. 17 shows a vertical, horizontal, cross-cut view of the unit shown at FIG. 16, that shows a lower wall, an upper wall and a space in between through which the strap goes.

Figure 17A:
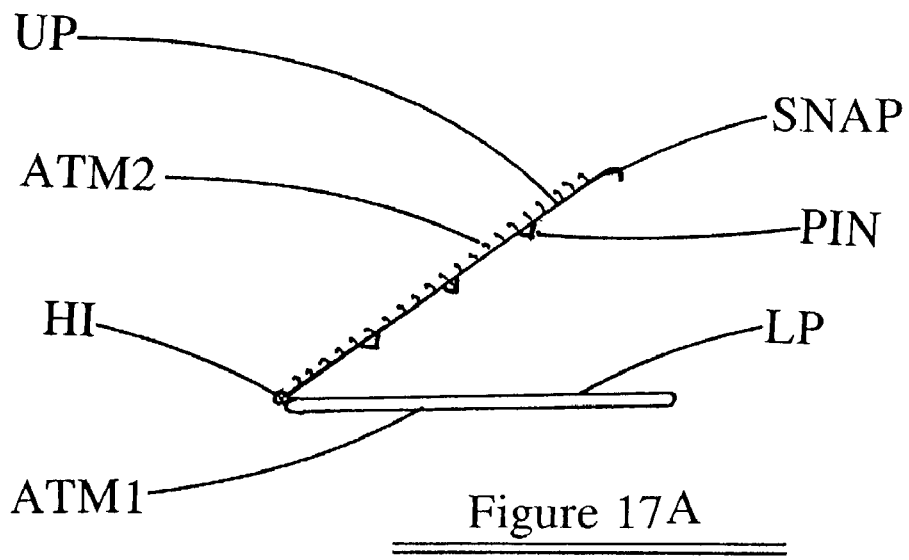

FIG. 17A shows a vertical, longitudinal, cross-cut view of the unit shown at FIG. 16. It shows a lower wall and an upper wall hinged together at HI.

Figure 18:
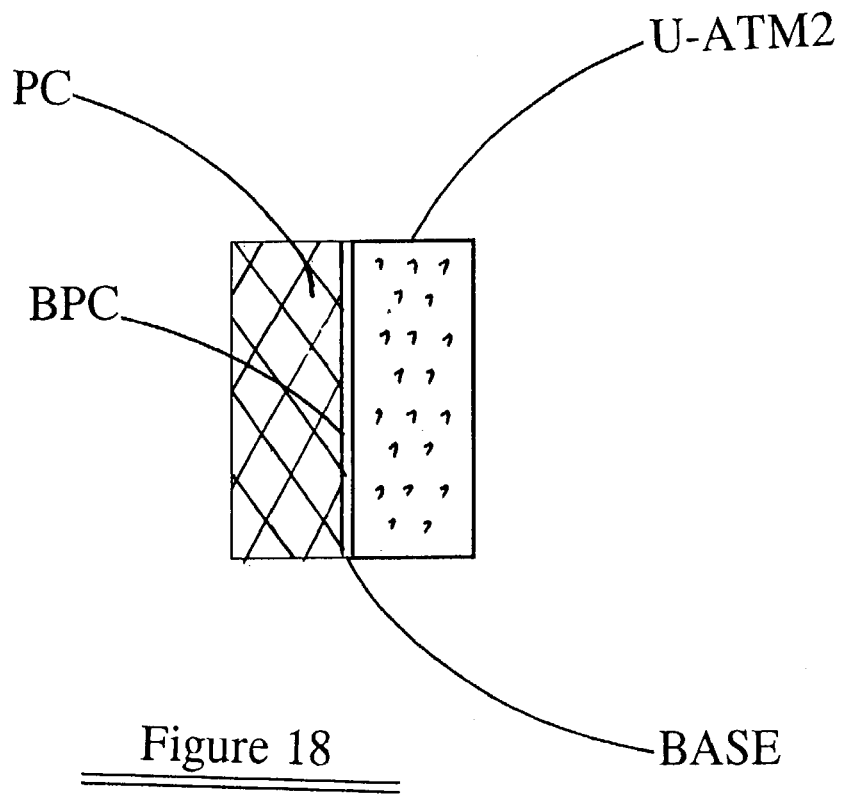

FIG. 18 shows an end piece which has an adhesive zone, under, PC and double-sided attachment means, U-ATM2, that allows the end of strap to be cut and attached to the upper surface of this piece.

Figure 18A:
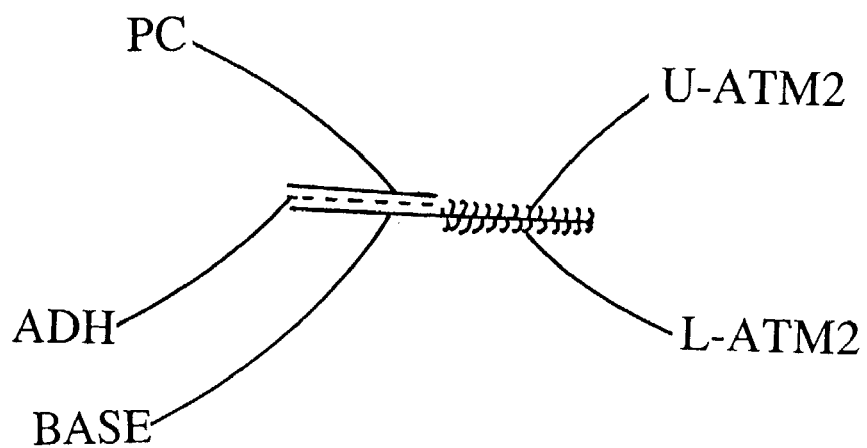

FIG. 18A shows the cross-cut view of the unit at FIG. 18, with the, ATM2 On its upper and lower surfaces and the adhesive, layer, ADH, under a protective cover, PC.

Figure 18B:
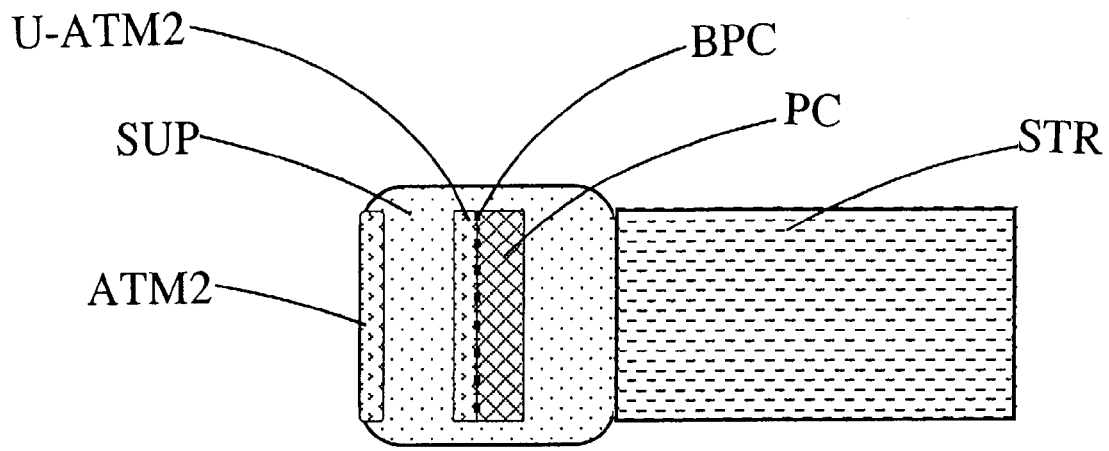

FIG. 18B shows an end piece unit shown at FIG. 18 attached to the front surface of a support, SUP.

Figure 18C:
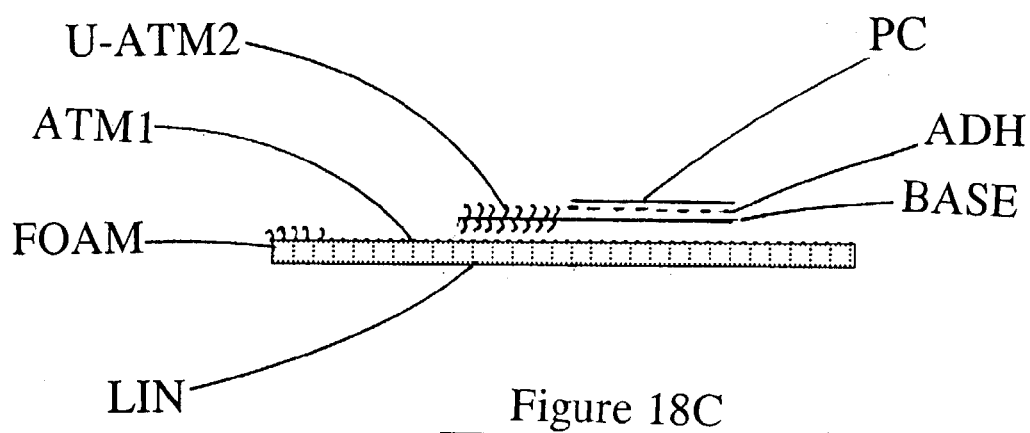

FIG. 18C shows a magnified vertical, cross-cut view of the end piece unit attached to the upper surface of the support, SUP as shown at FIG. 18B.

Figure 18D:
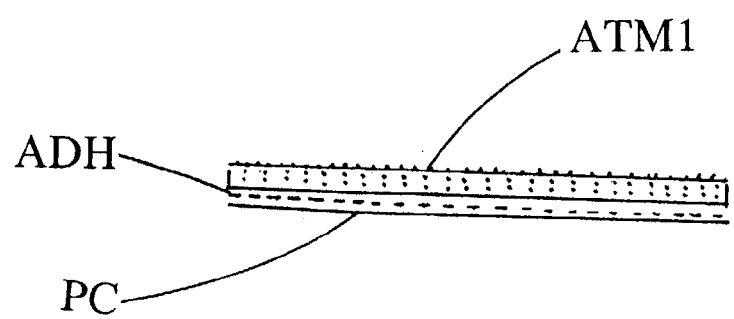

FIG. 18D shows a complementary unit that allow to change the surface of a vinyl support for use with an end piece shown at FIG. 18.

Figure 19:
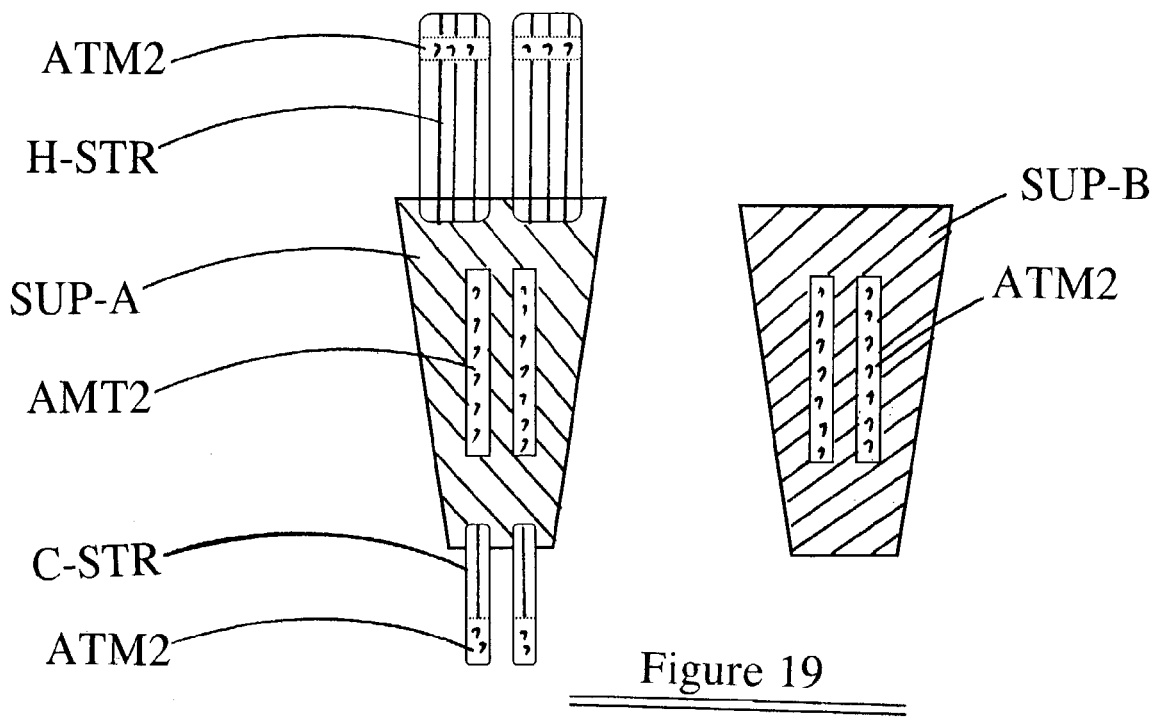

FIG. 19 shows a support units, SUP-A and SUP-B, for the sides of head, in which each one will cover one side of the face and be held together by straps.

Figure 20:
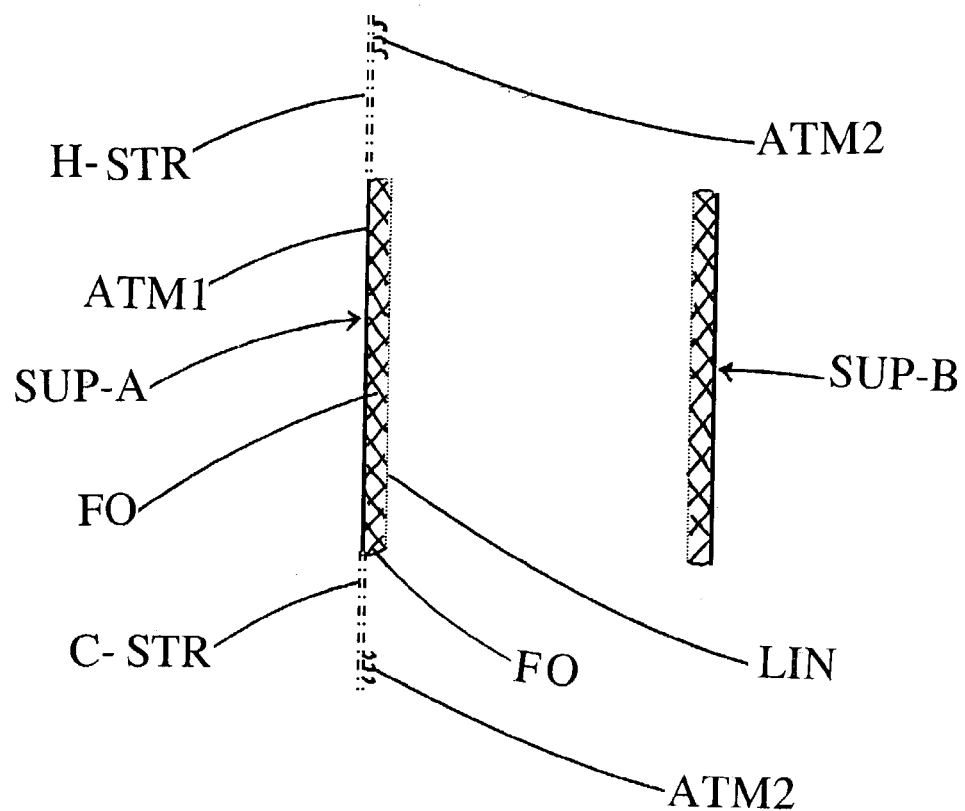

FIG. 20 shows the side view of the units shown at FIG. 19.

Figure 21:
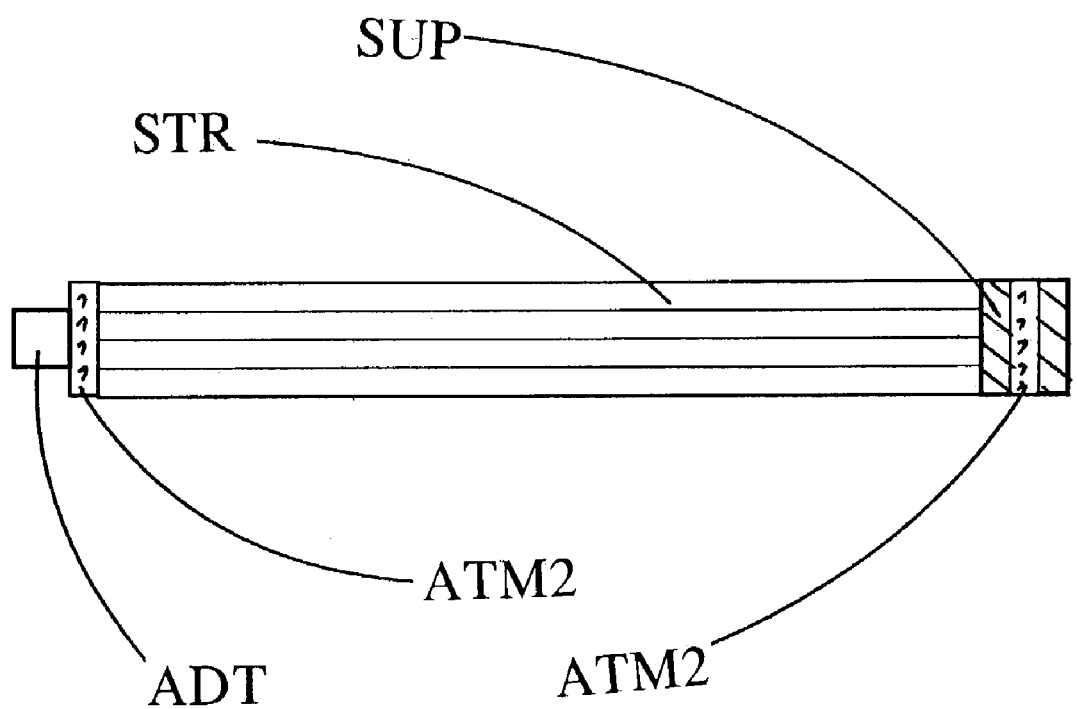

FIG. 21 shows a strap means for use with the unit shown at FIG. 20. This strap goes around the head horizontally.

Figure 22:
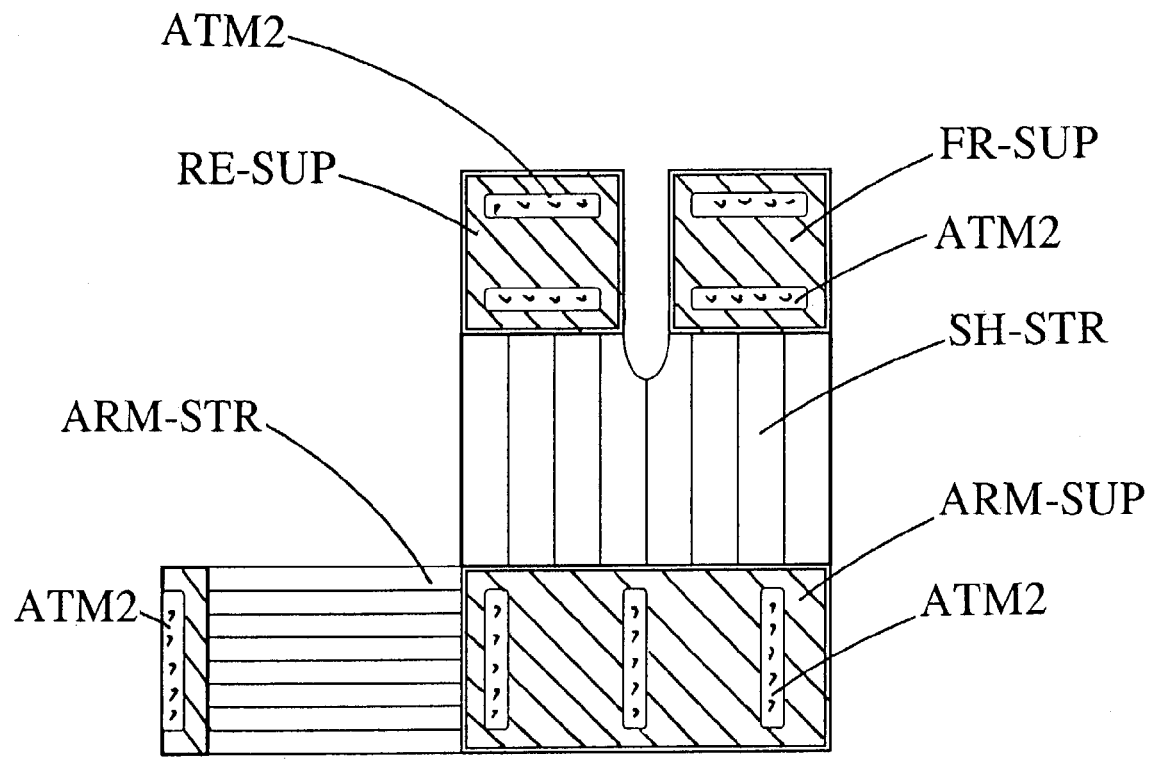

FIG. 22 shows a support means for shoulder.

Figure 23:
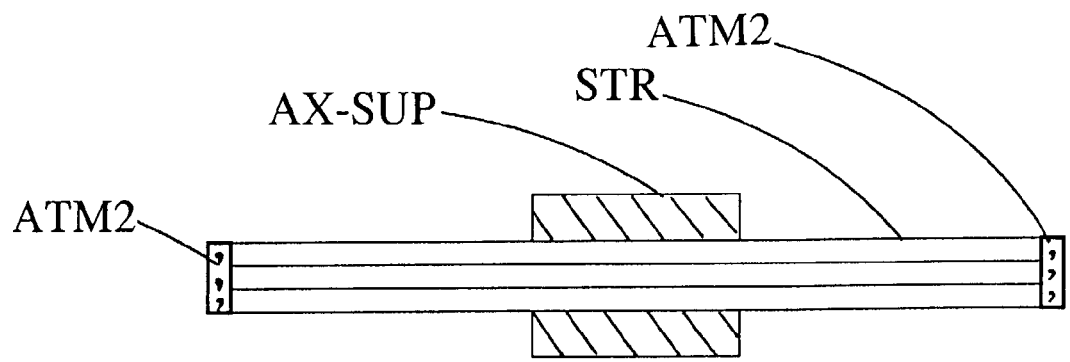

FIG. 23 shows a strap means for use with the unit shown at FIG. 22.

Figure 24:
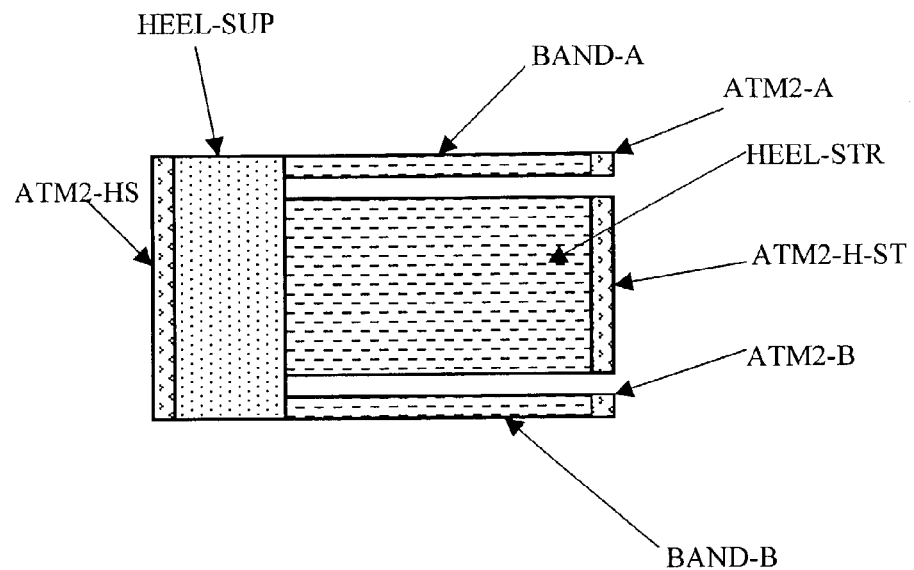

FIG. 24 is a support unit means for the ankle.

Figure 25:
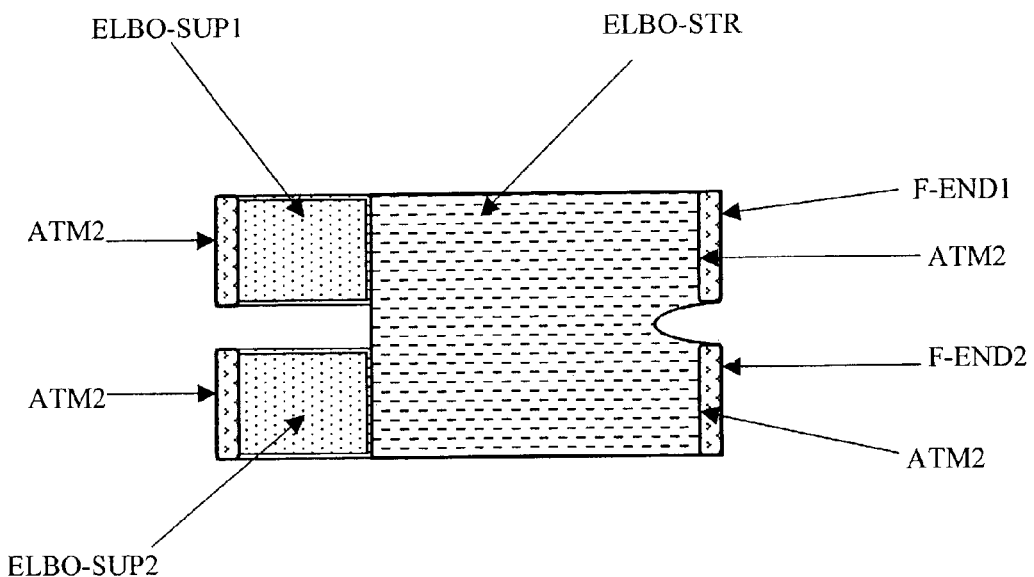

FIG. 25 shows a support unit means for the elbow.

Figure 26:
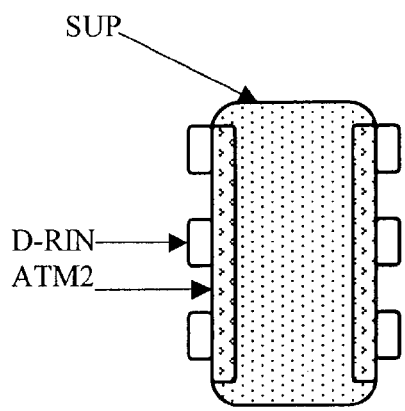

FIG. 26 shows a support unit means for the hip that also uses D-Rings. The straps are not shown in this figure.

Figure 26B:
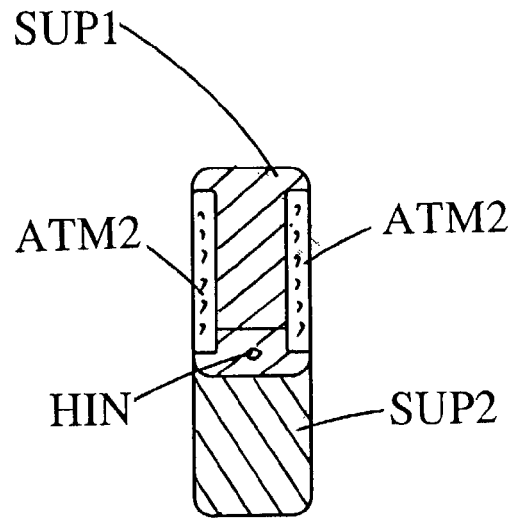

FIG. 26B shows a hinged-support unit means for the hip that allows the support to angulate.

Figure 26C:
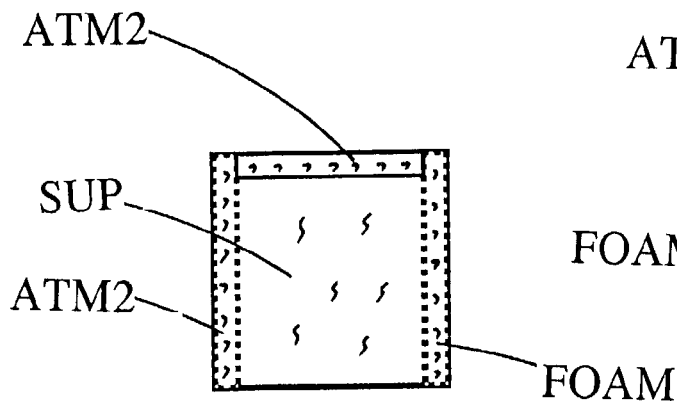

FIG. 26C shows a protective support unit for the chest that prevents clothing from touching the wound site.

Figure 26D:
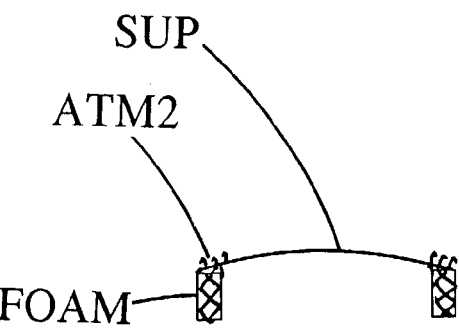

FIG. 26D shows the vertical, cross-cut view of the unit shown at FIG. 26D, the foam walls, FOAM, on the sides would keep the support away from wound.

Figures 27, 28:
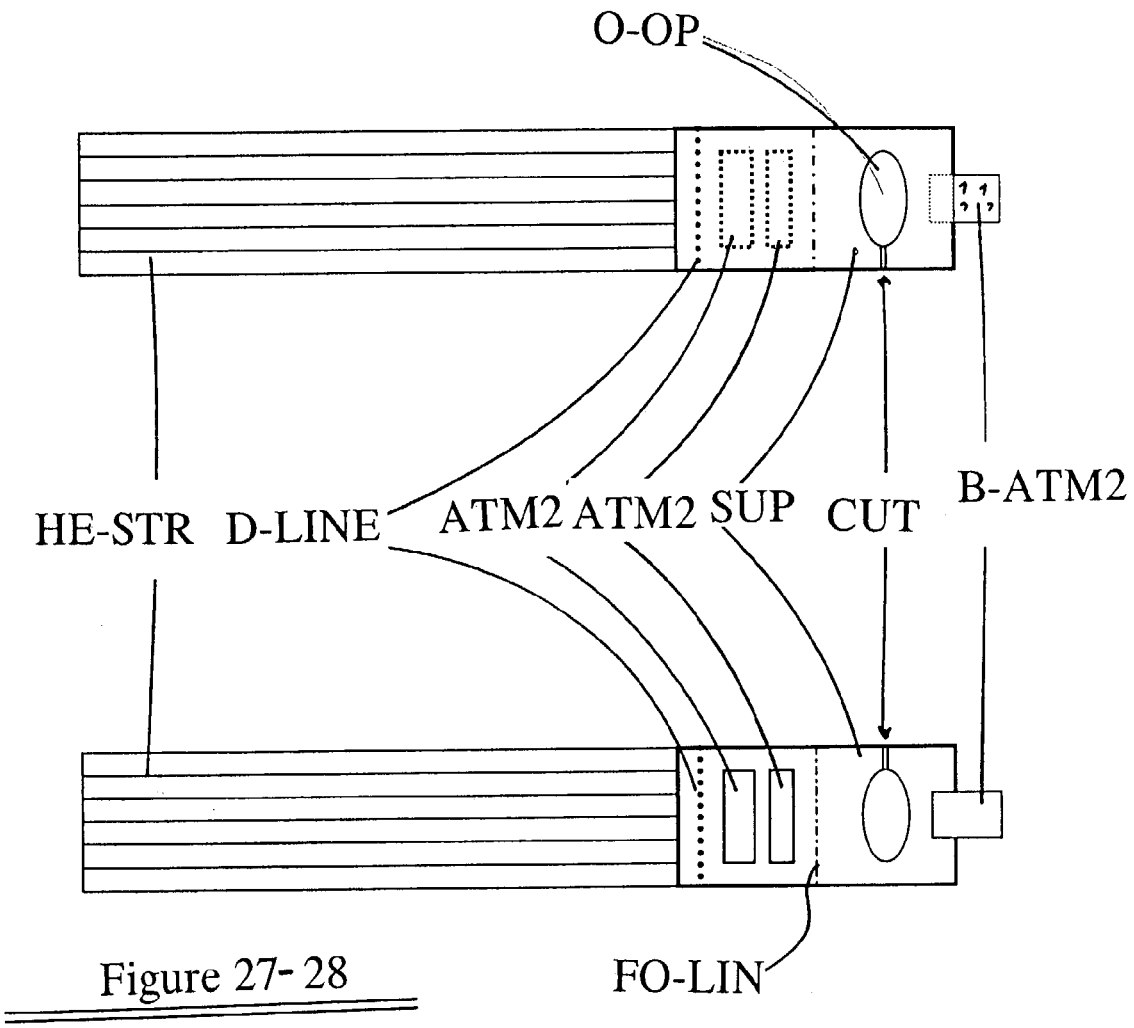

FIGS. 27-28 show the front and the rear view of a support means for the ear.

Figure 29:
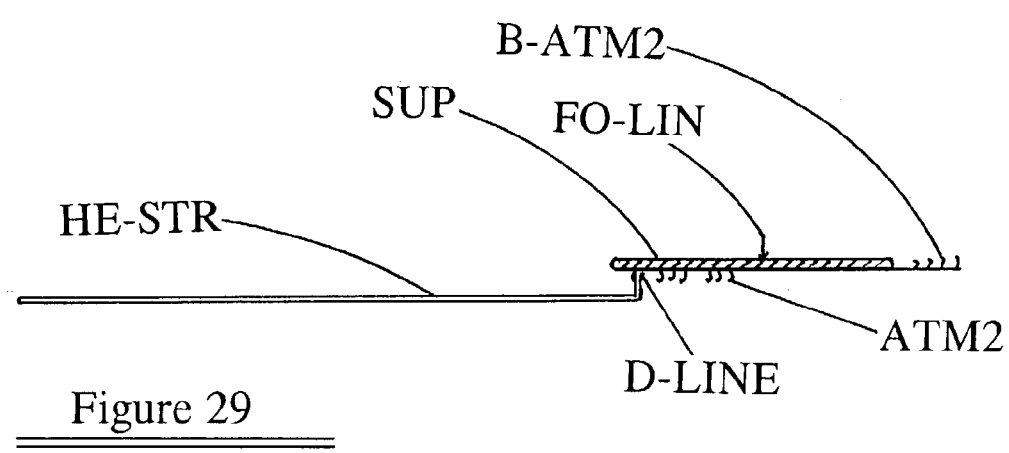

FIG. 29 shows the side view of the support means for the ear.

FIG. 30 shows a support means for the Pacemaker-Defibrilator Wound.

FIG. 31 shows the side view of a support means shown in previous FIG. 30.

FIG. 31A shows the side view of the arrangement of the straps for the unit shown at FIG. 31.

Figure 32:
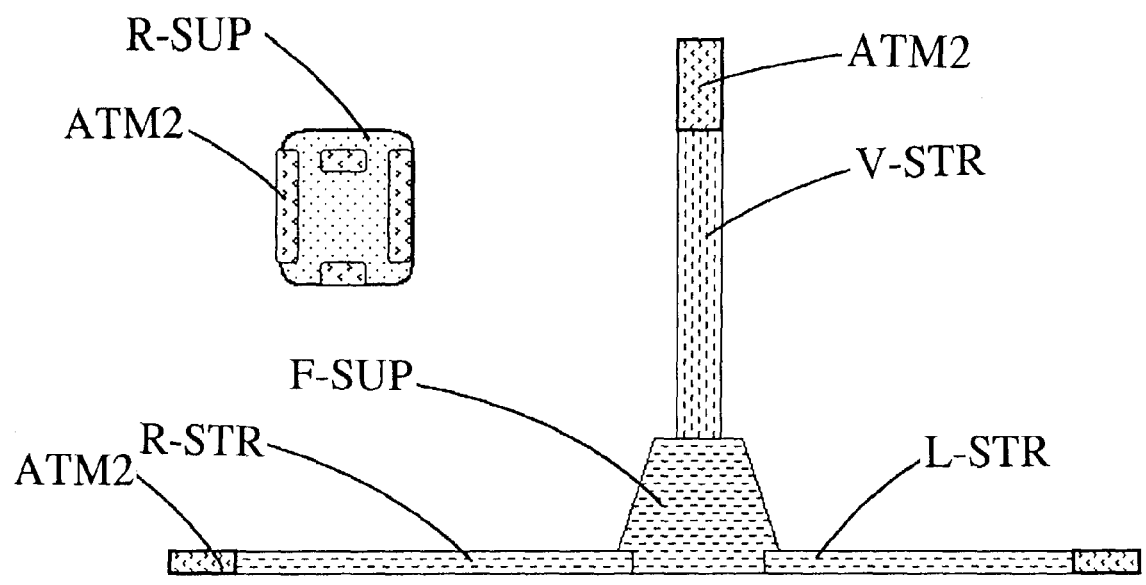

FIG. 32 shows a modified model of the unit shown in previous FIG. 30.

Figure 33:
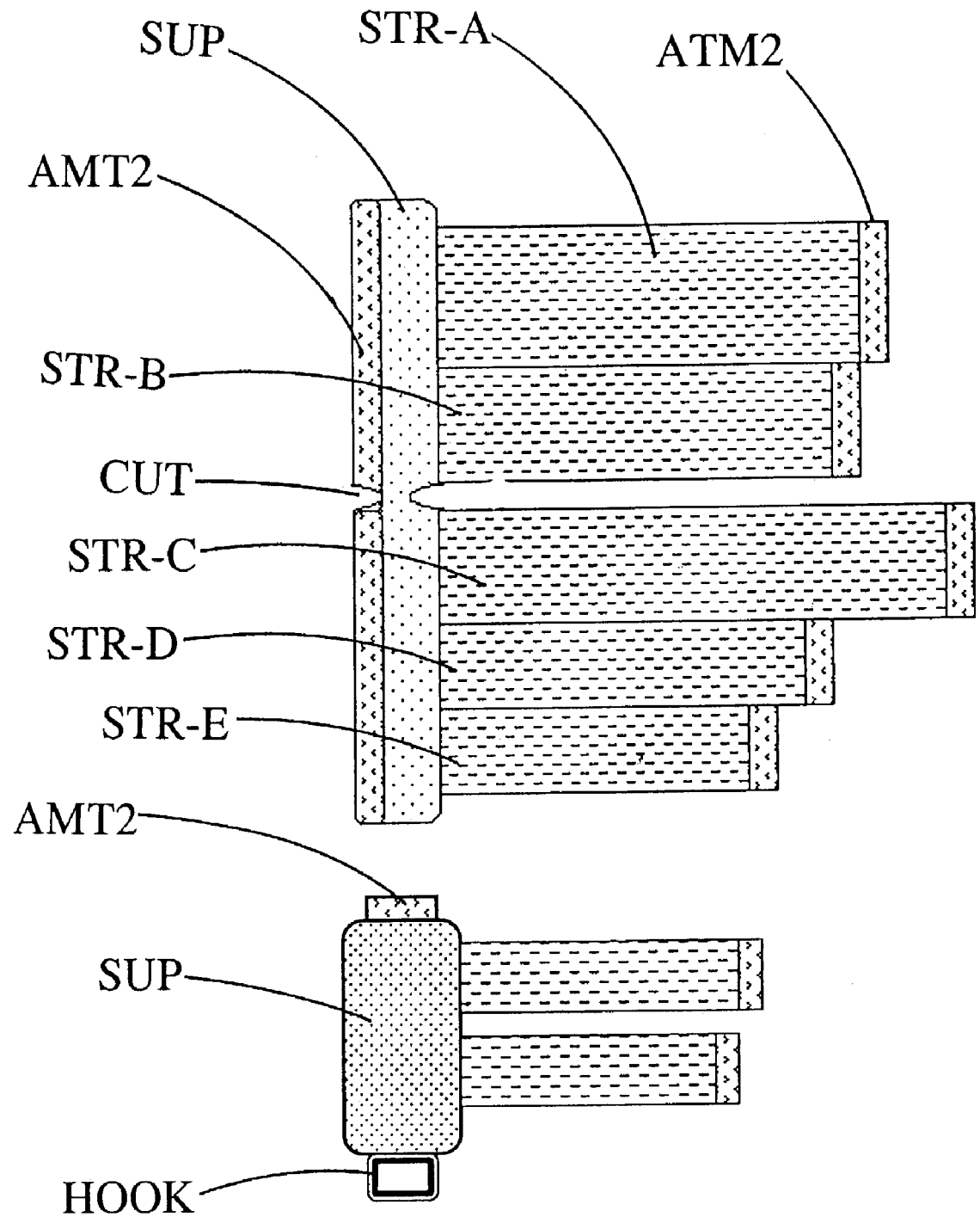

FIG. 33 shows a support means for use in the arm, forearms and hand.

Figure 34:
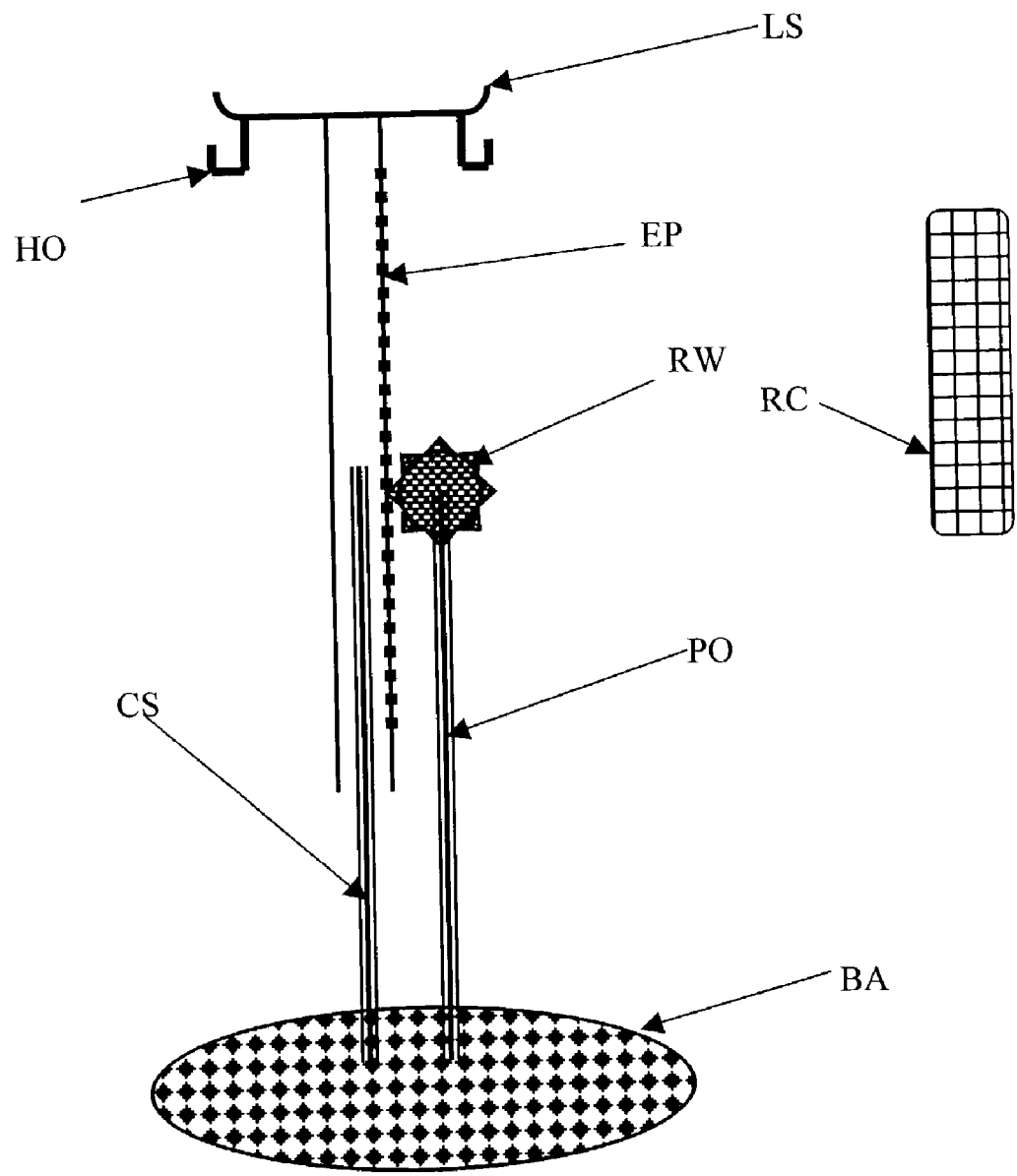

FIG. 34 shows a remote-controlled elevator means that allow an extremity to be moved up and down.

Figure 34A:
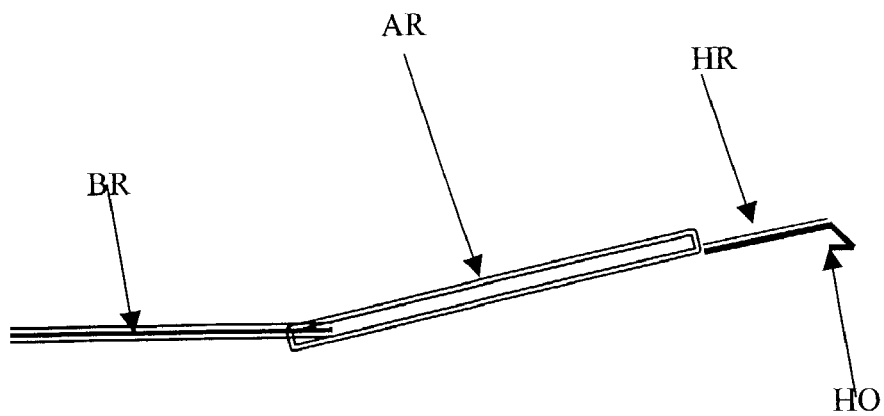

FIG. 34A shows a cradle means for use with the elevator means shown at FIG. 34.

Figure 35:
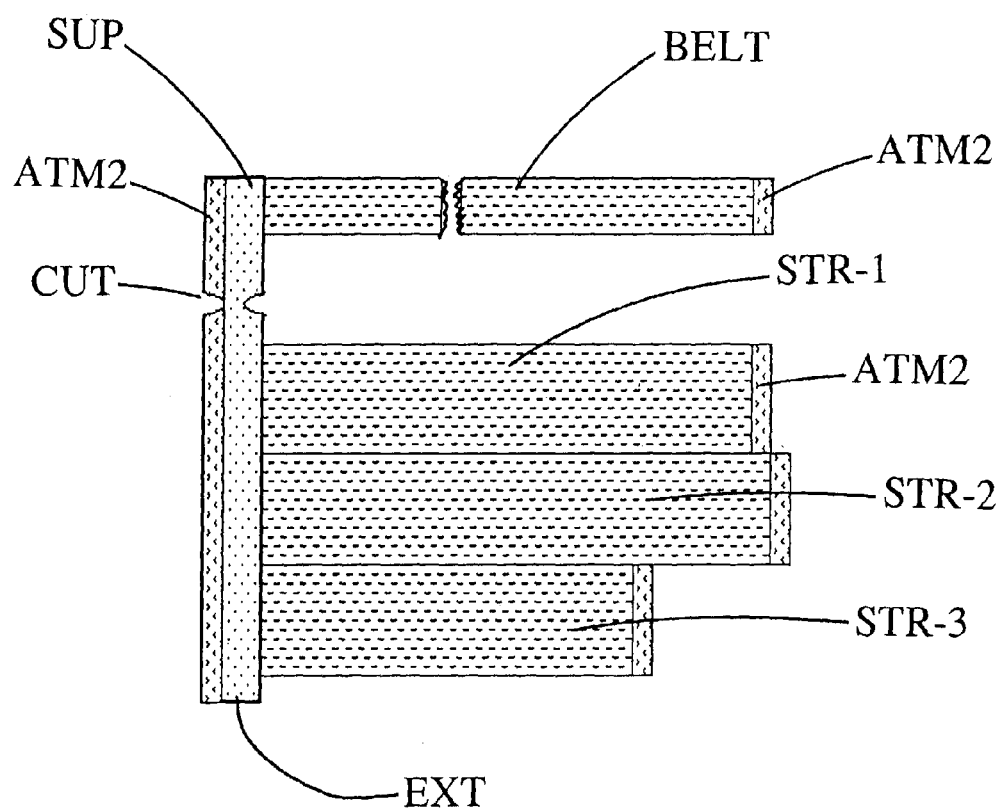

FIG. 35 shows a support means for use in the thigh area.

Figure 35A:
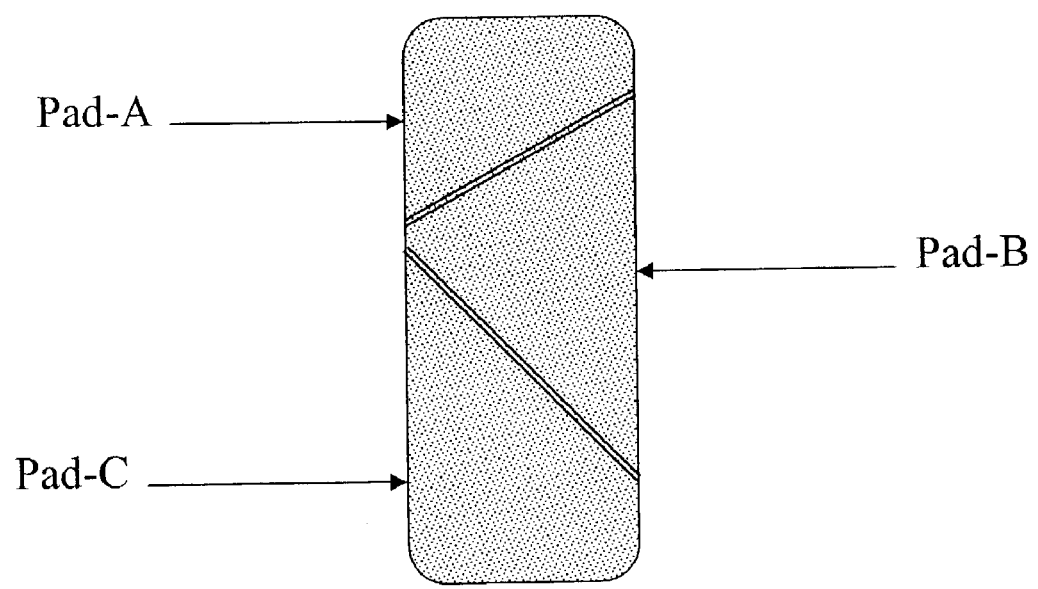

FIG. 35A shows a pad means for the hip support which consists of three loosely attached pieces.

Figure 36:
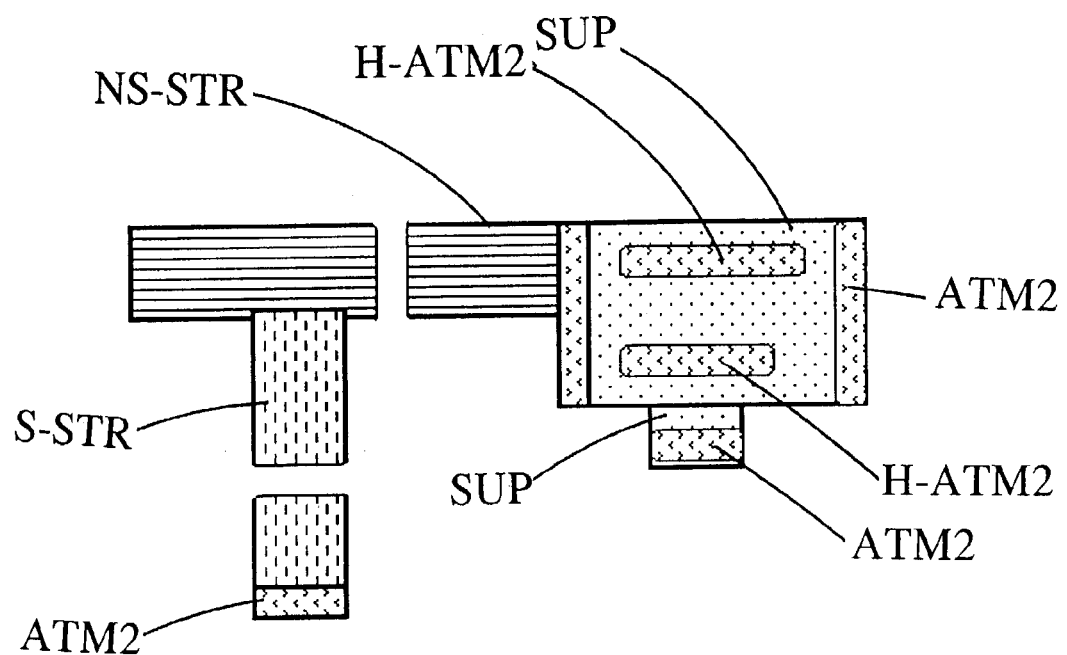
Figure 36:
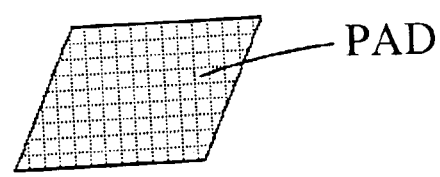

FIG. 36 shows a support means for use in the groin area.

Figure 37:
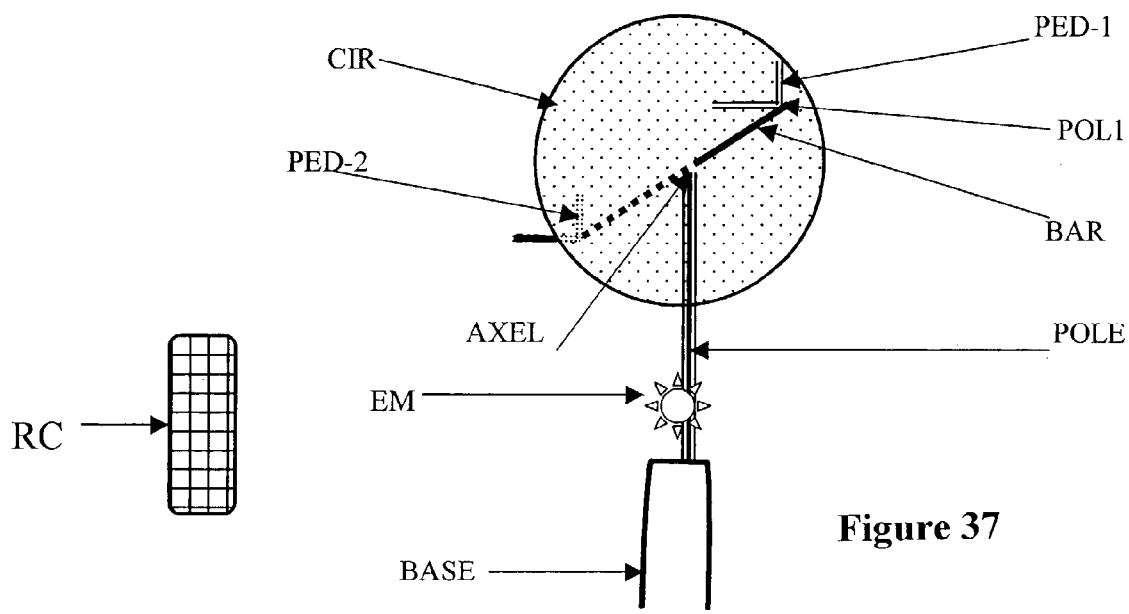

FIG. 37 shows a remote-controlled cycling means for making a patient to exercise his/her legs.

Figure 38:
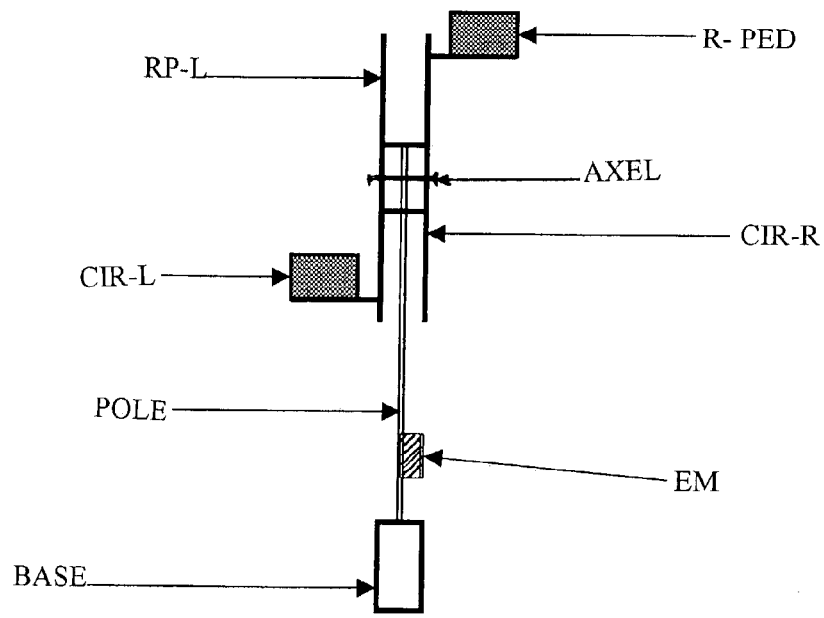

FIG. 38 shows the side view of the unit shown at FIG. 37.

Figure 39:
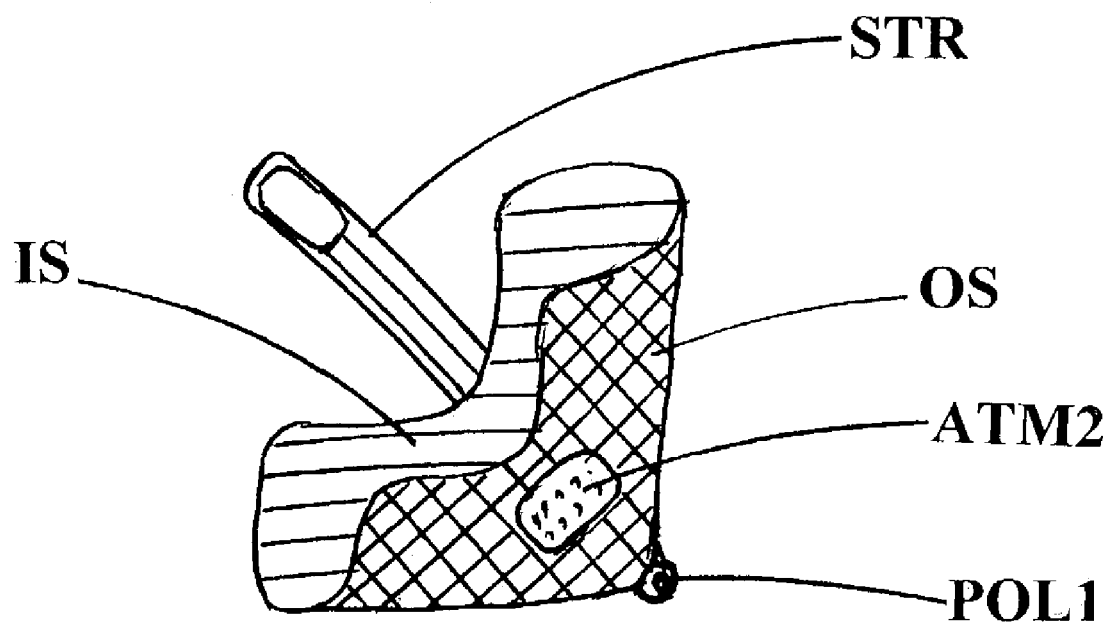

FIG. 39 shows an enlarged side view of a pedal for the unit shown at FIG. 37.

DETAILED EXPLANATION OF THE FIGURES

FIG. 1 shows the front/top view of a wound dressing unit which consists of a clear front support, SUP, which has a strap, STR, attached to it on the left side of the support (when we view the Figure). In this model the support, SUP, is made from a layer of vinyl and has zones of attachment means shown at ATM2, made from hook type of hook-loop-fastener (VELCRO™). These zones are further specified by ATM2-A, ATM2-B and ATM2-S. These hook-fastener patches allow complementary pieces such as the body of the strap, STR, which function as a loop-fastener, attachment means. This property allows the strap, STR, to attach to the zones of the hook-fastener attachment means shown at ATM2-A, ATM2-B and ATM2-S, or any similar zones, on a detachable, re-attachable basis. Specifically the applicant has found during his experiments that when the strap is made from special material such as (LYCRA-™), it allows the strap to attach to the hook type attachment means, categorically shown at ATM2, on a detachable, re-attachable basis. The free end of the strap, STR, also has a band made of hook-fastener attachment means ATM2 (this may be double-sided) that allows it to be attached to the rear surface of the body of the strap, STR, on a detachable, re-attachable basis. The zones of the attachment means, ATM2-A and ATM2-B, allow complementary bands here shown at BAND-A and BAND-B, which have a body made from the same material as the strap, STR, or similar units to be attached to them on a detachable, re-attachable basis. These bands are designed to attach to the attachment patches, ATM2-A and ATM2-B of the support, SUP, on a detachable, re-attachable basis.

Importantly, instead of the zones of the attachment means (ATM2-A) and (ATM2-B) the unit may have a second, long zone of the hook-fastener attachment means such as the zone ATM2-S on the left border of the support, SUP, as shown at FIGS. 1A and 1B. This method allow the attachment of the strap, STR, or the bands BAND-A, BAND-B to support. The free end of the strap, STR, shown in the left side of this figure has a piece of adhesive tape, ADT, (the actual size is bigger) which allows it to be attached to the rear surface of the strap, STR, after making a U-turn, and keep the end piece stable. The adhesive tape has folded protective cover (PC). This part is shown in detail in FIG. 2. Instead of the adhesive tape, ADT, this part may be made from any other materials or means that will allow the end of the strap, STR, to be attached to the surface of the strap, STR, or the support, SUP, on a detachable, re-attachable basis. The protective cover of the adhesive tape allows it to be removed without touching the gloves.

Importantly, the line of attachment of the strap, STR, to the support, SUP, may be made to be optional, by having a matching layer of adhesive attached to the border of the support, SUP, and protected by a protective layer, PC. (as shown at FIGS. 1C and 1D) This allows the end of the strap, STR, to be attached to the zone of the adhesive layer on an optional bases. The user will choose the length of the strap and cut the extra piece and attach the end of the strap to the outer surface of the support, SUP. This method allows the length of the strap to be chosen for a given person.

FIG. 2 shows the side view of a wound dressing unit shown at FIG. 1. This figure shows the cross-cut side view of the support, SUP, and the strap, STR, attached to it on left side. The support, SUP, has zones of the attachment means: ATM2, on its upper surface which is made from hook type of hook-loop-fastener (VELCRO™). In this view the ATM2-B and ATM2-S are shown. These zones allow complementary pieces such as the body of the strap and Band-B to be attached to them on a detachable, re-attachable basis. In this view, BAND-B is attached to the right side of the support and has a body made from the same material as the strap, STR.

The piece of gauze pad, GP, is attached to the lower surface of the support, SUP, by a detachable, attachment means, ATM, which can be a layer of adhesive. This allows the pad to be removed and replaced by a similar or another piece. This allows a soiled gauze pad to be exchanged with a fresh one.

Importantly, the zone of the attachment means, ATM, shown in the lower surface of the support, SUP, may be made from a zone of adhesive layer with multiple individually, removeable protective covers as shown at FIG. 1D. This method allows some of these zones, such as a zone in the lateral side of the support adjacent to the base of the BAND-B, to be used for the attachment of the support, SUP, to the skin, after the removal of its protective cover. The center zone may be used for the attachment of the gauze pad, GP to the support. The free end of the strap, STR, shown on the left side has a patch attachment means: ATM2 made from hook type of hook-loop-fastener (VELCRO™). This patch allows the free end of the strap, STR, to be attached to the outer surface of the body of the strap, STR, on a detachable, re-attachable basis. The cross-cut of the adhesive tape, is shown both at the upper and lower surfaces of the strap, STR, the layer of adhesive, ADH, is shown with a short, dotted-line. It has a protective cover, PC, which is shown on the upper surface by a folded shape and in the lower surface by a straight line. The folded model is easier to be removed without being touched by the gloves. Thus, please note that the adhesive layer can be on both the upper and lower surfaces of the strap, STR.

The unique importance of this unit is that it allows the subject to dress a wound with use of one hand, which the applicant believes is very important.

Method of use:
1. The user places the support piece, SUP, on the wound and places the strap, STR, under the limb so that by pressing on the strap, STR, it will loosely prevent the support, SUP, from moving.
2. He/she wraps one of the bands, the proximal band, BAND-A (it is optional to choose BAND-A or BAND-B) around the limb in the opposite direction of the strap, STR, and bring its free end to attach to the ATM2-A from the support, SUP, on detachable, re-attachable basis.
3. The user wraps the distal band, Band-B, around the limb on the opposite direction of the strap, STR, to bring its free end and attach it to the ATM2-B on the support on a detachable, re-attachable basis.
4. The user wraps the strap, STR, around the limb for attachment to the ATM2-S on the side of the support, SUP, on a detachable, re-attachable basis. Then he/she can wrap the end of the strap around the outer surface of the strap to make a U-turn and adhere the adhesive tape ADT from the end of the strap to the rear surface of the strap, or by use of a connection means ATM2.

Importantly, in models which the layer of adhesive, ADH, is placed on the lower surface of the strap, STR, (instead of being on the upper surface of the strap as shown), the user will wrap the strap on the support. Then the attachment means, ATM2, or the adhesive layer, ADH, from the free end of the strap, STR, will be attached or adhered to the outer surface of the body of the strap, STR.

Based on the experiments of this applicant, this process takes only about 15-20 seconds of time or less and makes a very stable and easy method of wrapping a wound with the use of one hand only.

Importantly, the unit may consist of only one strap, STR, with the bands, BAND-A and BAND-B omitted. This unit is functional except that it does not allow the placement by one hand as easy as can be done with the presence of the bands.

Importantly, in some cases the user may need to have the gauze pad, GP, or the support, SUP, adhered to the skin. To satisfy this need, the front of the gauze pad or its border may have a layer of adhesive to allow such an adherence. The adhesive layer will have a protective cover such as PC, which will be removed before use. Similar to this condition, the support may be needed to adhere to the skin on its border or some portion of its body. In such cases, again the lower surface of the support or its border will also have a layer of adhesive to allow the support to be adhered to the skin. The adhesive layer will have a protective cover such as PC, which will be removed before use. This model is shown in more details at FIG. 1D.

FIG. 1A shows the front view of a wound dressing unit that is similar to the unit shown previously in FIG. 1 except that this unit shows some more beneficial features such as:

1. The support, SUP, has two parallel zones of hook-fastener, attachment means, shown at ATM2-A and ATM2-B. The importance of these attachment means is that it allows easier control of the strap, STR. So that the strap will first attach to the attachment means ATM2A and then to ATM2-B.
2. The adhesive tape at the end of the strap, STR, shown at ADT-S, consists of two separate pieces or a piece with a cut on it. The importance of this method is that it allows an easy placement of the adhesive tapes since it will be the handling of two smaller adhesive tapes rather then one big one.

Second, the two pieces allow one piece to be in a different area of a wound side. This will make a different curve that will help in some places such as the leg area, with the upper adhesive tape above the large muscle of the leg and the lower adhesive tape on the lower part of the calf. This will prevent the strap from moving.

3. The support, SUP, has an adhesive tape of its own, shown at ADT-C, which will be adhered to the skin of an area such as the thigh. This will prevent movement and falling of the support in areas such as the thigh and groin at which the particular shape of the area and the function of the muscles move the support and strap down toward the knee. However, when this adhesive tape or an adhesive layer under the support, as shown in FIG. 1D, is adhered to the skin it will prevent the support from moving down.

Importantly, instead of the adhesive tape, shown at ADT-C, the lower surface of the support, SUP, may have a zone of adhesive with multiple individually, removeable protective covers, as shown at FIG. 1D. This will allow some of these zones such as a zone in the lateral side of the support on the lower surface of ATM2-A to be used for the attachment of the support, SUP, to the skin, after the removal of its protective cover, and other zones to be used for attachment of the gauze pad.

4. The strap, STR, has another adhesive tape, shown at ADT-B, which will be adhered to the skin on an area such as the thigh to prevent the strap from moving and falling.

Please note that each one of these adhesive tapes will have their own protective layer, which will be removed before use.

FIG. 1B shows the side view of a wound dressing unit shown at FIG. 1A. This figure shows the vertical, cross-cut view of the support, SUP, with two zones of hook-fastener attachment means, shown at ATM2-A and ATM2-B on its upper surface. The adhesive tape of the support, SUP, is shown on its lower surface at, ADT-C. (the arrow is aimed to the cover of the this tape)

The strap, STR, is attached to the support on the left border. Two adhesive tapes of the strap, STR, are shown in this figure. The cross-cut of the adhesive tape, ADT-S, is shown at the left side and the figure shows an adhesive layer, ADL, covered with a piece of protective layer, PC. The cross-cut of the adhesive tape, ADT-B, is shown at the lower, middle part of the strap. (the arrow is aimed to the cover of the this tape)

FIG. 1C shows the front view of a support, SUP, that has a body made from a layer of clear PVC shown at SUP, which has a zone of adhesive in its left border covered with a protective layer, PC. The support, SUP, has two zones of hook-fastener, attachment means, shown at, ATM2, that allow a strap to be attached to them on a detachable, re-attachable basis. Also Importantly, the lower surface of this support, SUP, has a zone of adhesive layer, not shown at this figure but at FIG. 1D, with multiple individually, removeable protective covers which is explained in details at FIG. 1D.

FIG. 1D shows the vertical cut view/side of the support, SUP, which has two zones of hook-fastener, attachment means, ATM2, on its upper surface. The adhesive layer, ADH, is shown at the upper surface on the left side with a dotted line. The adhesive, ADH, has a protective layer, PC. Also importantly, the lower surface of the support, SUP, has zones of adhesive, ADH, shown in a dotted line with multiple individually, removeable protective covers, PC-S1, PC-GP AND PC-S2 which allow the following options.

a. The adhesive, ADH, under the protective covers, PC-S1 AND PC-S2 allows the support, SUP, to be adhered to the skin to prevent the movement and falling of the support on the wound site.
b. The adhesive layer, ADH, under the protective covers, PC-GP allows the gauze pad, GP, to be adhered to the body of the support.

Method of use.

1. The user measures the circumference of the limb to decide about the length of the strap, STR, and will cut the strap in a proper length.
2. The user removes the protective layer from the layer of adhesive, ADH, on the upper surface of the support, SUP.
3. The user attaches the free end of the strap to the layer of adhesive, ADH. This will make a unit that has a strap with a proper length and can be used to dress the wound site.
4. The user removes the protective cover, PC-GP to adhere a gauze to the body of the support.
5. The user removes the protective covers, PC-S1 AND PC-S2, from the lower surface of the support, SUP, and adheres the support, SUP, to the wound side. This will prevent the support from moving.
6. Then he/she will be able to attach the strap and use the unit as explained earlier.

FIG. 1E shows the side view of a method that allows the end of the strap to be attached to the outer surface of the support or the strap STR, itself and allows the strap to be detached and re-attached afterward. In this method the lower surface of the strap, STR, has a zone of hook-fastener, attachment means, ATM2, which is adjacent/attached to a longer zone of loop-fastener, attachment means, shown at ATM1. The lower surface of the loop-fastener, attachment means, ATM1, has a layer of adhesive, ADH, that has a cover of its own, PC. The attachment of the hook-fastener, attachment means, to the loop-fastener, attachment means, is on a detachable, re-attachable basis. This method allows the user to attach the loop-fastener, attachment means, ATM1, located at the lower surface of this combination to the outer surface of the support or the strap on a desired place by removing the protective cover, PC. This will adhere the loop-fastener, attachment means, ATM1, on the outer surface of the support or the strap on a permanent basis. The user can then detach the zone of hook-fastener, attachment means, ATM2, from the loop-fastener, attachment means, ATM1, and re-attach it on a detachable, re-attachable basis. Thus, the end of the strap will be attached to the support or its own surface on any desired area.

FIG. 1F shows the side view of a unit similar to the unit shown in the previous FIG. 1E except that this model allows the end of the strap to be placed in any desired area of the support or the strap. In this model, the rear surface of the hook-fastener, attachment means, ATM2, has its own layer of adhesive layer, ADL, that is protected by a cover, PC. The rest of the body of this unit is similar to the unit shown in the previous FIG. 1E. This allows the user to remove the protective cover, PC, from the lower surface of the loop-fastener, attachment means, ATM1, and adhere the combination to the outer surface of the support or the strap. The user will then wrap the strap, STR, over the support, SUP, shown at FIGS. 3-4 and adhere the end of the strap, STR, to the outer surface of the hook-fastener, attachment means, by removing the protective cover, PC. This will fix the hook-fastener, attachment means, ATM2, the lower surface of the strap, STR, and loop-fastener, attachment means, ATM1, on the outer surface of the strap, STR, on a permanent basis. The user can then detach the zone of hook-fastener, attachment means, ATM2, from the loop-fastener, attachment means, ATM1, and re-attach it on detachable, re-attachable basis. Thus, any part of the strap, STR, can be attached to the support or the strap in any desired area.

FIG. 3 shows the front view of a wound dressing unit that is similar to the unit shown at previous FIG. 1, except that this unit utilizes special pieces (previously introduced by this applicant and referred to as YD pieces), shown better at FIG. 4. YD pieces are made from a piece of medical adhesive tape with a having zone of loop-fastener attachment means as shown at ATM1 on its lower surface where the adhesive material is located, as shown at FIG. 4. It allows the end of the YD piece to attach to the zone of ATM2-S from the support unit. The rear surface of this zone, ATM-1 on the YD piece has a zone of hook-fastener, ATM2, of its own that allows a complementary piece, such as strap, to attach to it on a detachable, re-attachable basis.

The external end of the YD piece has a layer of adhesive, ADH, covered with a folded protective layer, PC, that allows it to adhere the adhesive part onto the skin. This allows the user to apply this unit with one hand and exchange the wound dressing without the need for another adhesive part each time, since the piece, YD, can be detached from the support on a detachable, re-attachable basis.

FIG. 4 shows the vertical cross cut view of a wound dressing unit shown at FIG. 3. This figure shows the vertical-cut view of the support, SUP, and the strap, STR, as shown in FIG. 3. The support, SUP, has patches of the attachment means which, in general, are shown at, ATM2, on its upper surface. These are further specified by the zones such as ATM2-B, ATM2-S, etc. In this figure only the ATM2-S is shown, but the attachment means ATM2-B is not shown, since the cross-cut was in the middle of the unit. On the right side of this figure the piece YD is shown. The left lower surface of the piece YD has a zone of loop-fastener attachment means, ATM-1 that allows it to be attached to the zone of ATM2-S from the support, SUP, on a detachable, re-attachable basis. The piece YD, has a layer of adhesive, shown at ADH, on a dotted-line, that allows this part to adhere to the skin and hold the end of the support, SUP, securely on the skin. The layer of adhesive has a folded protected cover (PC) that will be peeled off before use. Importantly, the folded protective cover PC allows it to be held and pulled off easily from the adhesive layer to expose the adhesive layer. This allows users with latex gloves to use these units easily, without touching the adhesive layer that sticks to the latex gloves. The piece YD, has a patch of the attachment means: ATM2 on its upper surface, made from hook type of hook-loop-fastener (VELCRO™). This patch allows a complementary piece such as the body of the strap, STR, or other units with loop-fastener properties to be attached to it on a detachable, re-attachable basis.

The gauze pad, GP, is attached to the lower surface of the support, SUP, by attachment means ATM.

The free end of the strap, STR, shown on the left side has a zone of attachment means: ATM2 made from hook type of hook-loop-fastener (VELCRO™). This patch allows the free end of the strap, STR, to be attached to the outer surface of the body of the strap, STR on a detachable, re-attachable basis. Please note that such an attachment can be achieved when the outer surface of the strap, STR, is able to attach to the hook-fastener, attachment means. This is possible either by altering the manufacturing process of the strap or making a double sided strap by sewing the fabric with the loop-fastening, attachment means property outside. The cross-cut of the adhesive tape, ADT, is shown both on the upper and lower surfaces of the strap, STR, by marking the layer of adhesive, ADH, with a short, dotted-line. This layer is pointed out at the upper surface but not on the lower surface to avoid a crowded figure. The adhesive, ADH, has a protective cover, PC, which is shown at the upper surface by a folded shape and at the lower surface by a straight line. The folded model is easier to be removed without being touched by the gloves. Thus, please note that the adhesive layer can be on either or both the upper and lower surfaces of the strap, STR.

FIG. 5 shows the front view of a support unit, SUP, which has a non-stretchable body (may in some cases be stretchable) and openings, OP, that allow air and gasses to pass through. It has the zones of the attachment means, ATM2 made from hook type of hook-loop-fastener and which are farther specified by ATM2-A, ATM2-B and ATM2-S. Importantly, many of the supports used for the units in this application use a material that is now commercially available and has an outer surface made from a layer of loop-fastener attachment means, ATM1, an inner surface made of a soft lining that stands on the skin and a thin layer of foam in between. The use of this material with zones of hook-fastener attachment means, ATM2, gives the option of attaching straps with both loop-fastener body and hook-fastener end pieces. Also importantly, the double-sided, hook-fastener pieces such as the one shown at FIGS. 18 and 18A may be used with these units with or without adhesive zones. Importantly, a double-sided ATM2 piece will allow a strap and support that have a body with loop-fastener to be attached to each other on a detachable, re-attachable basis.

Importantly, instead of the zones of the attachment means, ATM2-A and ATM2-B, the unit may have a second long zone of the hook-fastener attachment means, such as the zone ATM2-S, on the left border of the support. This allows the attachment of the strap, STR or the bands BAND-A and BAND-B to the support to occur.

FIG. 5A shows the front view of a support unit which is similar to the model shown at FIG. 5, except the support is made from a body with an outer surface made from a layer of loop-fastener attachment means, ATM1. This support, SUP, has a second support piece, referred to as Support A, SUP-A, that is attached to the body of the first support along the Attachment Line, AL. The free end of the support A, SUP-A has a zone of hook-fastener attachment means, L-ATM2, that allows the Support A, SUP-A, to attach to the outer surface of the first support on a detachable, re-attachable basis. The advantage of the second support, SUP-A, is that it allows tubings, wires, suction bulbs, etc., to be kept between these two layers securely. The outer surface of the second support, SUP-A has a pocket, POC, of its own that allows a suction bulb to be placed inside it as well, if needed.

This unit will have a strap that will be attached to one side of support, SUP, and the free end of the strap will attach to the attachment means, ATM2, of this support as explained previously. These units may be placed in the arm, around the limb, chest, abdomen, etc.

FIG. 6 shows the general view of a support unit similar to the unit shown at FIG. 1, except this unit is modified for use on the leg area and to support the legs as well. This unit allows secure and easy dressing of the leg without the need for adhesive tapes. In this model the support, SUP, has a long, rather rectangular shape and covers the front of the leg, or the wound site. The support, SUP, is shown in more detail at FIG. 6A. It has a long zone of hook-type, attachment means on its right border that allows pieces made of loop-fastener attachment means, ATM1 to be attached to it on a detachable, re-attachable basis. The left border of the support unit, SUP, is attached to three straps: STR1, STR2 and STR3. These straps are attached to the support unit on a permanent basis although importantly, they may be attached to the support on a detachable, re-attachable basis. These straps are sized to wrap around the leg on its upper, middle and lower part. These straps will wrap around the leg and their free ends, attach to the support, SUP, by use of loop-fastener attachment means, at their ends shown at ATM1-1, ATM1-2 AND ATM1-3 which are respectedly attached to the end of the straps STR1, STR2 AND STR3. The applicant had made this method for dressing/supporting the legs and thighs in a very practical, adjustable fashion. In this model the straps are also made from one or two layers of (LYCRA™) and the support means are made from vinyl, although they may be also made from any other materials such as fabrics or any other proper manmade materials. The support may have openings in it to allow sweat and air to pass through. The support also allows a gauze pad or a long, removeable layer of lining, shown at LIN, in FIG. 6A, or a pad, to be placed under it. The lining or pad prevents irritation, and also allows application of pressure and/or medication to be applied as well.

Importantly, this unit allows electrical leads/pads to be held in place for a programmed stimulation of the leg muscles and tissues. This will be done for various reasons such as prevention of muscle weakness, or of phlebitis.

Importantly, the unit is very valuable, since it allows the pressure in different segments of the leg to be adjusted. Also importantly, the unit can be removed and easily applied, and can be placed over the regular stocking and pants as well.

The lining will be attached to the support, SUP, on a detachable, re-attachable basis, to allow washing or exchanging. This model can be made to extend to the thigh area as shown in this applicant's previous applications. In this model a couple of straps will attach the thigh piece to a waist strap in order to prevent it from sliding.

Importantly, the straps of this unit may be attached to the body of the support unit independently, by having one end of the straps be attached to one border of the support and the other end attached to the other border of the support both on a detachable, re-attachable basis. This was shown by the applicant in his previous models and applications to USPTO.

FIG. 6A shows the general view of the support unit shown at FIG. 6. In this figure the body of the support is shown at SUP, and it has openings, OP, a long zone of hook-fastener attachment means, ATM2, which is shown in its right border. A layer of lining, LIN, is attached to the rear surface of the support, SUP, and extends from its borders. The lining, LIN, is attached to the body of the support on detachable, re-attachable basis to allow the exchange.

FIG. 6B shows schematically a support unit similar to the unit shown at FIG. 6 placed on a leg. This unit has three straps, each of which have straps with their own attachment means and that are attached to the support, SUP, on a detachable re-attachable basis. The support of this unit has one long zone of hook-fastener attachment means, ATM2, in the right and left border of its body. This model allows the effective length of the straps to be adjusted from both ends of the straps. The three straps are further marked as STR1, STR2 AND STR3, and are attached to the support unit by use of the loop-fastener attachment means, ATM1, which are part of the free ends of the straps. When the straps have the loop-fastener attachment property of their own, they will attach to the support themselves. These straps are properly sized to wrap around the leg on its upper, middle and lower part. They can be attached to the support, SUP, by use of the pieces of loop-fastener attachment means at their ends shown at ATM1-1, ATM1-2 AND ATM1-3 which are respectedly attached to the one end of the straps STR1, STR2 AND STR3. The other ends of the straps have similar attachment pieces as well, which are not marked in this figure to prevent a crowded picture. In this model the straps are also made from one or two layers of (LYCRA, ™) and the support means is made from clear vinyl, although it may also be made from any other materials such as fabric or any other manmade material.

FIG. 6C shows schematically the general view of a support unit similar to the unit shown at FIG. 6, except in this unit the body of the strap is made from a non-segmented fabric, marked CSTR. This fabric is attached to the body of the support along one of its borders and continues to wrap around the leg, but ends with three separate loop-fastener attachment means, ATM1-1, ATM1-2 AND ATM1-3. The end pieces allow the end units to attach to the hook-fastener attachment means, ATM2 from the support, SUP, on a detachable, re-attachable basis. Importantly, the value of this model is that the continuous body of the strap does not leave an open area or a line of compression on the legs. Importantly, this unit is also chosen to show that a strap may have more than one ending.

FIG. 7 shows the front and side views of a support unit similar to the unit shown at FIG. 5, which is modified by adding a U-shape extension to it. This unit is designed to support the middle and lower ankle area in both sides of the ankle, inside and out, and allows the compression of those areas. In this model a support piece similar to the support, SUP, shown at FIG. 5 or an extension of the support of the leg support is utilized and shown as the inner support, I-SUP, and functions to compress the inner part of the ankle. This support, I-SUP, moves down and covers the inner ankle and connects to a piece of an elastic strap shown at U-STR. This U-strap makes a U-turn under the foot and attaches to another non-stretchable support that functions as the outer support, O-SUP. This compresses and supports the outer ankle area and has a band, C-BAND, which is an elastic strap that wraps around the lower leg or ankle area and holds the O-SUP in place. The C-BAND allows a wider strap, such as STR3, shown at FIG. 6B to wrap around the I-SUP AND O-SUP keep these supports in place, squeezing the tissue in between them. The importance of this unit is:

A. The U-shaped support means supports the middle, lower and lateral part of the ankle and allows the compression of the tissues in these areas. The importance of this unit is that it allows dressing and compression of the tissue and vessels on the lower inner ankle-foot area to occur for a better result and in a measurable with placement of a balloon connected to a gauge and adjustable manner. The use of this unit is in vascular problems, particularly in venous insufficiencies of the legs, where compression of vessels for decreasing the inner pressure of the vessels and prevention of extravasation of fluid in this area is needed. Please note that in order to prevent confusion, the upper parts of the unit are not shown in this figure.

Importantly, in some cases there is a need for further compression of the lower leg to raise the amount of pressure on the tissue. In such cases the inner support, I-SUP and the outer support, O-SUP, are made from rather rigid pieces, such as a shaped polymer or metal, that are connected to each other in the lower side by a strap. The position of this strap on the supports is adjustable and allows the distance of these two inner support, I-SUP, and the outer support, O-SUP, to be adjusted. Importantly, the outer surfaces of the inner support, I-SUP, and the outer support, O-SUP, have attachment means, such as hook-fastener attachment means, ATM2. This allows a wider, horizontal strap or two straps similar to one shown at C-BAND to wrap around the lower leg and hold the I-SUP and the O-SUP in place to further compress the tissues in this area. This combination can be used as a separate unit, or in combination with the leg support. Importantly, the rigid supports can be pre-shaped or alternatively made from a material which accepts the shape of the area after placement. Pieces of shaped foams or pads may also be placed between the wound dressing and these supports. A flat, fluid-filled balloon attached to a measurement unit may be placed between the support and lining to monitor the pressure in the wound.

FIG. 7A shows a support unit for the leg as shown at FIG. 6C, except this figure shows a U-shaped extension attached to it. In this figure the support, shown at FIG. 6C, has an extension which will function as the inner support, I-SUP. This piece moves down and covers the inner ankle and then connects to a piece of strap shown at U-STR. This follows a model which was shown at FIG. 7.

FIG. 7B shows the side views of the pieces for a U-shape extension for use with the leg support. This unit is designed to support the upper and lower ankle and allows the compression of these area for prevention and treatment of the wounds particularly, in the inner, lower leg and the ankle area. This figure shows inner and outer supports, I-RIG-SUP and the O-RIG-SUP, that are made from rather rigid pieces, such as a shaped polymer or metal. The outer surface of these supports have zones of attachment means, such as hook fastener, ATM2S-A and ATM2S-B. These zones of attachment means allow a series of horizontal straps, similar to the band shown at C-BAND from FIG. 7 and other wider straps to wrap around them and hold the inner and outer rigid supports, I-RIG-SUP and the O-RIG-SUP. To squeeze them together, for further compressing the lower leg-inner ankle, tissues in between. The lower ends of the inner and outer supports, I-RIG-SUP and the O-RIG-SUP are attached to each other by use of a piece of elastic strap or a loop attachment means ATM1-S, that attaches to the inner hook fastener attachment means, I-ATM2S, and outer hook fastener attachment means, O-ATM2S, on a detachable, re-attachable basis. This method allows the distance between the two support pieces to be adjusted and match the width of the ankle area of a given user.

The inner surface of the inner and outer supports, I-RIG-SUP and the O-RIG-SUP has a zone of hook fastener, attachment means, ATM2 that allows a foam pad to attach to the inner surfaces of the supports on a detachable, re-attachable basis.

These support units will hold one or two pads made from one or two kinds of foams, FOAM, which allows the ankle area to be compressed by the use of this pad. The foam pad may be made from:
1. A layer of rather non-compressible foam that stands outside of the ankle area.
2. A layer of rather soft foam that covers the ankle area and allows the foam to accept the shape for the ankle area.
3. A soft lining that will cover the inner surface of the inner foam and will stand on the wound dressing of the ankle.

The outer surface of the non-compressible foam has a zone of attachment means, ATM1-F that allows this pad to attach to the inner surface of the inner and outer supports, I-RIG-SUP and the O-RIG-SUP, on a detachable, re-attachable basis.

A series of elastic straps will wrap around the supports to squeeze these two supports toward each other in order to compress the lower leg-inner ankle tissue in between.

Importantly, a flat, fluid-filled balloon attached to a measurement unit as shown at FIG. 7D may be placed under the inner support, and between another rather rigid unit on the foam, FOAM. This unit has a shape and size that matches the support unit, and allows the pressure in the wound area to be known.

FIG. 7C shows schematically a padding made from a foam, FOAM, that will be placed under the supports, to allow the pressure formation in the wound area to be applied. The outer surface of the pad has a zone of loop-fastener attachment means, ATM1-F, that allows this pad to attach to the inner surface of the inner and outer supports, I-RIG-SUP and the O-RIG-SUP on a detachable, re-attachable basis. Importantly, this unit has an opening that is designed to stand on the inner and outer bony prominence of the ankle joint. This is critically important, since this method will allow the soft tissue of the ankle to be compressed. Otherwise, it will prevent proper transmission of the compression to the soft tissue.

FIG. 7D shows schematically an inflation unit for use with the unit shown at FIG. 7B. This unit consists of a flat, fluid-filled inflatable balloon, IB, which is attached to a measurement unit, such as a gauge, G, by use of a three-way stopcock, TWS. The unit will be inflated by a pump, P, and after the optimum pressure inside the balloon is achieved the three-way stopcock can be closed and the pump and gauge removed.

The inflatable balloon, IB, will be placed under the inner support, I-RIG-SUP a detachable, re-attachable basis. Importantly, the system may be a closed unit to allow the pressure to be noted all the time. An alarm unit may be incorporated to allow significant change of the pressure to be known.

FIG. 7E shows schematically, the general view of a protective-support unit for the feet, designed to prevent compression of the heel and the sides of the ankle, and may be used with the units shown at FIGS. 6-7 to prevent pressure to the foot. This unit consists of a thick foam, FO, balloon/s or similar pads which are shaped for being placed on the ankle area and to wrap around it. This piece of foam, FO is held in place properly by a method consisting of:

1. Attaching the free ends of the foam, FO together by hook-loop fastening means, shown at ATM2-L and ATM1-L which are placed at the ends of the foam, FO. The ATM2-L is a piece of hook-fastener, attachment means, that attaches to the zone of loop-fastener, attachment means, ATM1-L, from the outer surface of the body of the foam, FO, on a detachable, re-attachable basis.
2. An elastic strap, STR, shown at left, of this unit. This strap, STR, is made of a double sided, LYCRA (™) and has an outer free end with a zone of hook fastener, attachment means, ATM2-F. The inner end of the strap, STR, is attached to the side of the foam, FO, somewhat distant from the free end of the foam, FO. At the site of attachment of the strap, STR, to the foam, FO, the strap, STR, has a zone of loop fastener attachment means, ATM1-F. Importantly, the loop fastener, attachment zone, ATM1-F may be part of the foam, FO or attached to it. At the time of use the foam, FO, will be wrapped around the lower leg above the ankle and held in place by attaching the ATM2-L to ATM1-L. So it will be doughnut-shaped.

Importantly, the strap, STR, is sized to move down from one side of the ankle and wrap around the sole of feet in a U shape fashion and to move up in the other side of the ankle and attach to the zone of the hook attachment means, ATM2-S located on the side of the foam, FO. Then Importantly, the strap, STR, will follow its move and will be pulled in front of the shin to attach to the zone of the loop fastener attachment means, ATM1-F located on the foam, FO, on a detachable, re-attachable basis, by use of the ATM2-F. Importantly, the elastic strap, STR, will create a reasonable tension in order to keep the foam, FO, in place securely. This method and means will prevent from the foam, FO, to move up in the leg and the prominence of the ankle of the humans will prevent the foam, FO, from moving further down to the foot.

It is very important that the body of the elastic strap, STR is not irritant to the leg and this is an advantage and makes the use of such a unit possible.

Please note that the design of this unit is important since it will prevent from the
a. Movement of the foam, FO, along the shin.
b. The rotation of the foam, FO around the shin, since the strap, STR, will prevent from such a move.
c. Importantly, the body of the strap, STR, allows it to attach to the surface of the foam, FO, by attaching to the attachment means ATM2-S, due to the special property of the strap. This is a critical issue that plays a very important role in function of this unit.

Importantly, the strap may have a Y shape with two end pieces, in order to allow one of the ends of the strap, to move in the rear part of the leg and the other end of the strap to move in front of the leg and to attach to the ATM1-F. This may give some more stability to these units.

Importantly, the strap may also have and attachment means to allow it to be attached to the hook of the leg elevator unit, described in this application.

Please note that the foam, FO may have a cover made from fabric on its surface or to go over it in order to make it a comfortable unit and to allow the attachment means to be fixed on it.

The foam may have extra pieces attached to it to add thickness to the body of the foam, and to function as a further protective means. One such piece may be attached to the body of the strap, STR, to stand on the sole of the foot and prevent it from touching the footpiece of a bed if such prevention is necessary.

The shape of the foam may vary and have more thickness in the bottom to prevent from the heel reaching the bed etc. This unit may be used with the units shown at FIGS. 6-7 to prevent from pressure to the foot. In this case the unit may be used alone or to be attached to the sides of the U shaped supports.

FIG. 8 shows the front view of a special stretchable support unit made from shaping the same material used for the strap or the LYCRA (™). Here, the Lycra is modified with use of bands made from materials such as latex as shown at L-BAND. The shaping of this stretchable material or the use of sewing techniques allow an elastic, shaped support to be made. Such a support is useful in areas with a particular shape and function, such as knees, ankles, elbows, toes, etc. This shaped, stretchable support allows better handling and placement of these units. Importantly, the following advantages are also available:

a. In this method the support has an elastic body that will be pulled to keep it in place with a comfortable tension. This mild, comfortable tension is an important property for use in these areas.
b. The support unit stretches and conforms to some degree and accepts the shape of the area. Also, such a body allows this body of the support to change with change of the wound areas such as over joints, knees, ankles, hips, elbows with extension and closure.
c. The inner part of the support is a soft, non-irritant fabric and does not cause skin reaction.
d. On the scalp it allows an easy dressing of the wound.
e. Importantly, the side where the strap is attached stretches in both direction and allows this unit to fit a shaped area, such as the scalp. A transverse strap allow this unit to be further stable on the scalp. This will make a cross-shaped unit.

In this figure the attachment means of the support is shown at ATM2 and the strap at STR. A D-Ring may also allow the strap to be adjusted.

FIG. 9. Shows a long strap that is attached to a transparent support, SUP. This figure also illustrates two important parts:

1. a transparent pocket for placement of information, here referred to as the Information Pocket, IP which is on the support, SUP or on the strap. The Information Pocket, IP, allows a piece of paper, consisting information to be placed inside the pocket. This information may be, for example, time of the use of the dressing, medication underlying IV line, or other information about the person using the unit, etc., and can be exchanged as needed.

Importantly, the information pocket, IP, may be placed on the wall of the strap to be part of the wall or simply attached to it.

2. Importantly, the body of the straps, STR, may have zones of materials such as latex, LA, in or on it in order to allow the shape of the strap to be conformed or modified to a desired shape. It can be used to prevent curling of the strap, etc. The shape, width, thickness, materials utilized, and other characteristics of these zones may vary.

Importantly, two straps may criss-cross to allow a better placement. This is more useful in strapping the head wounds, with one strap going around the front and occipital area and the other going from the vertex to the under chin area.

FIG. 10. Shows schematically the use of D-Rings with the support unit. In this figure a transparent support, SUP has a D ring, D-RING on its right side that allows the strap of the unit to go through, make a U-turn, and attach to its own surface. This is another method of adjusting the length of the strap as mentioned in the text.

FIG. 11. Shows schematically a cradle, CR, on a stand that allows a limb to be placed on it. The angle and height of the cradle can be adjusted by means connected to the base, BA. The height can be adjusted by control of the height of the pole, PO and the angulation by the hinge, HI. This unit allows a strap or the support part of the support unit, shown at FIGS. 3-4 to be placed on the cradle of this unit and be attached to it by use of a weak adhesive or by a detachable, re-attachable means. Thus, the combination allows the user to place the support on a limb with one hand and adjust its size and tension. This unit may also be useful in dressing a wound manually. This unit may have an exchangeable cover in case changing is needed in hospitals or wound clinics.

FIG. 12 shows a general view of the rear piece of a support unit designed for use for the supporting of the wounds on the heels and toes. In this figure the piece that stands on the heel is shown at, HE and it has a lower sole, SOL-1 that has a hook-fastener attachment means, ATM2, on its surface. This piece also has a strap, STR-1 with a zone of hook-fastener, attachment means, ATM2, on its end this piece complements the piece shown at FIG. 13 to make a unit shown at FIG. 14.

Importantly, these heel and toe pieces which may be made from shaped Lycra (™) or similar fabric, with use of latex material as mentioned, so that this combination will:
a. Be soft, non-irritant and comfortable.
b. Allow the unit to be pulled to accept the form of the underlying area and fit well.
c. Allow one size to be used in many patients.
d. Allow the pieces to be placed inside one another and so that many of them, such as 15-20 at a time, may be placed inside one box, thus reducing storage size.
e. Allow the patients themselves to adjust the length of the unit as needed.
f. Importantly, both the heel and front pieces may have a cut with a strap on their lengths to allow their width to be adjusted as well. The strap will hold the open area in control.
g. Importantly, both the heel and front pieces themselves may be made from two pieces to allow the width to be adjusted as one piece can be attached to the other one along a zone of attachment of a detachable, re-attachable basis.
h, Importantly, these pieces may be made from other shaped materials.

Importantly, the attachment means will be complementary and one attachment means, ATM, will be faced with a complementary attachment means on the other side. Or, the body of the shaped areas will function as the complementary attachment means. This method allows, for example, the attachment means in the straps to be hook-fastener attachment means, ATM2, to be attached to the surface of the body of the heels made from loop-fastener attachment means.

FIG. 13 shows the general view of the front piece of the support unit shown at FIG. 12. In this figure the front piece, FR, also has a sole, SOL-2, that allows the hook-fastener attachment means, ATM2, from the rear piece shown at FIG. 12 to attach to its surface on a detachable, re-attachable basis. This piece has a strap with a piece of hook-fastener attachment means on its end. The front and rear pieces of these units are made from shaped materials.

FIG. 14 shows schematically the general view of the support unit for the heels and toes made from the combination of rear piece shown at FIG. 12, and front piece shown at FIG. 13. In this figure, sole, SOL-1, from the rear piece is attached to SOL-2 from the front piece on a detachable, re-attachable basis. Importantly, this allows the length of the unit to be adjusted. The strap STR-2 holds strap STR-1 from the rear piece and attaches to its own surface by the attachment means on a detachable, re-attachable basis. The strap STR-1 from the rear piece, HE, attaches to the body of the rear piece, HE, on a detachable, re-attachable basis.

FIG. 15 shows schematically a support unit for the heels and toes, made from the combination of the unit shown at FIG. 14, which is placed inside an outer piece that functions as the body of a shoe. The outer piece is made from a front sole shown at SOL-3 that is attached to the SOL-4 from a rear piece, OHE on a detachable, re-attachable basis. The combination is attached to the piece shown at FIG. 14 by attachment means between them.

This combination has the advantage of allowing an adjustable piece be used for use both in and out of the house. The outer piece will be removed inside the house and used when leaving the house.

The Use of Heel and Foot Protector with These Units:

Importantly, these units allow pieces of foam to be attached to their surfaces in order to prevent bed sores in these areas. For this purpose, shaped sponges will be attached to these pieces and prevent pressure sores. The shaped sponges may have open spaces in particular pressure areas to avoid pressure to those sensitive areas. It is important to note that the use of soles allow the sponges to be kept in place securely and not to rotate as commonly occurs.

FIG. 15A shows schematically the general view of a simple support unit for the dressing of the toes. This unit has a pocket, POK, made from a combination of a front and rear wall attached to each other along their borders, as shown in lines, SEW. In this particular model, the fabric is folded so the front border is closed, as well. The rear wall of this unit has two elastic straps, STR-1 and STR-2, which are made from Lycra and are attached to the body of the rear wall. The free ends of these straps have a complementary attachment means made from loop-fastener attachment means, ATM1, and hook-fastener attachment means, ATM2, respectively. Please note that one of the attachment means will be in front of one of the straps and the other will be on the rear surface of the other strap. This method will allow the end of these straps to attach to each other on a detachable, re-attachable basis.

At the time of use:
a. The pocket of the support, POC, will be placed in front of the foot and will cover the toes and its dressings. In this position the straps will be under the sole.
b. The strap, STR1, will be pulled to wrap around the heel to move up and cover the front of the ankle. This will be kept in position to allow the end of the other strap to attach to it.
c. The second strap, STR2, will be pulled to wrap around the heel and move up from the other side of the ankle so that its free end will attach to the attachment means, ATM1, from the strap, STR1.

This method will make a secure and simple means of holding the dressing of the toes in its place which is commonly difficult.

The support may be made from:
1. Elastic fabric
2. A regular fabric
3. A thicker unit such as the body of the supports mentioned earlier
4. Other various materials
5. The attachment of the straps to the body of the support may vary.

However, making this unit from the LYCRA (™) makes a very nice comfortable unit that has many advantage such as:

a. A support with an elastic body that will be pulled to keep it in place with a comfortable tension. This mild, comfortable, tension is an important property for keeping the dressing in place.
b. The support unit stretches and conforms to some degree and accepts the shape of the area.
c. The support is a soft, non-irritant fabric and does not cause skin reaction.

FIG. 15B shows schematically, the general view of support unit similar to the unit shown at FIG. 15A, except that the two bands or the straps of this unit, strap, STR-A, and strap, STR-B are placed in different directions. This unit also has a pocket, POK, made from a folded layer of a stretchable fabric, particularly, LYCRA (™) whose sides are sewn or attached together along the lines, SEW. The outer/top surface of this pocket, POK has a zone of loop fastener, attachment means, ATM1-AB. The rear/bottom surface of the pocket, POK, has one elastic strap, STR-A made from LYCRA (™) attached to it. The free end of the strap, STR-A, has a zone of loop-fastener, attachment means, ATM2-A, that allows this strap to wrap around the ankle and attach to the attachment means, ATM1-AB of the top of the pocket, POK. Importantly, when the body of the pocket is made from LYCRA (™) then the ATM2-A, of the strap, STR-A, will attach to the outer surface of the pocket, POK, on a detachable, re-attachable basis.

The unit may have another elastic strap, STR-B, made from LYCRA (™) that wraps around the base of the pocket, POK, and attaches to the loop-fastener, attachment means, ATM1-AB or the body of the pocket, POK, on a detachable, re-attachable basis. The function of the strap, STR-B, is to hold the base of the pocket together if there is a need for it.

Method of use.
1. The dressing will be placed on the wound and may be held momentarily in place by an elastic loop, E-LO, shown in the left lower part of this figure and is made from LYCRA (™).
2. The pocket, POK, will be pulled over the dressing via its opening, OP.
3. The elastic strap, STR-A, will be pulled to go around the ankle to have the zone of the loop-fastener, attachment, ATM2, of its free end to attach to the zone of loop-fastener, attachment means, ATM1-AB of the body of the pocket, POK.
4. The second strap, STR-B, will wrap around the bottom of the foot and will pull the side of the pocket and then the zone of the loop-fastener, attachment means, ATM2-B, of its free end, will attach to the zone, ATM1-AB, from the pocket, POK, or to the body of the pocket, POK.

This makes a simple unit that allows an easy dressing of the wound and its opening and closing.

The pocket may be made from.
1. Elastic fabric, particularly the LYCRA (™).
2. A regular fabric
3. A thicker unit such as the body of the supports mentioned.
4. Latex or any other man made materials.
5. The attachment of the straps to the body of the support may vary.

Importantly, this unit may have two straps similar to the strap STR-A, attached to the lower/bottom layer of the pocket, POK, in order for each one to move from one side of the ankle, as shown in previous figure.

FIG. 16 shows the top view of a buckle means designed to allow the length of the strap to be adjusted and a more durable, convenient unit for use with these units. This unit allows the length of the strap to be adjusted initially and yet allow some further adjustment after the initial placement of the strap on the support. This buckle consists of a lower flat piece, LP, and an upper flat piece, UP, that are hinged at hinge, HI. The other end of the upper piece, UP, will be snapped to the lower piece, LP, by the snap, SNAP. The snap allows the upper piece to be opened and closed along the hinge, HI. The upper piece, UP, has a series of spins, SPIN, on its lower surface that, when the buckle is closed, allow the strap to move in a one way direction as the arrows point and not be pulled back. The upper surface of the upper piece, UP consists of attachment means, ATM that allows the end of the strap to be attached to it on a detachable, re-attachable basis.

Importantly, the spins may be placed on the upper surface of the lower piece, LP.

The lower surface of the lower piece, LP, consists of a loop-fastener attachment means, ATM, that allows it to be attached to the hook-fastener attachment means of the surface of the support on a detachable, re-attachable basis.

At the time of use the strap will be pulled in the direction of the arrows and will be placed between the upper, UP, and lower pieces, LP. Then it will make a U-turn along the border of the upper piece, UP, and attach to the surface of the upper piece, UP, by itself or with the help of a matching attachment means or weak adhesive, with the extra length cut after length adjustment. The free end of the strap will finally be attached to this buckle and the buckle attached to the support, SUP, on a detachable, re-attachable basis. The extra length of the strap will allow its length to be adjusted and the position of the buckle on the support allows the effective length of the strap to be adjusted as well. The snap, SNAP, allows the upper piece, UP, to be opened and the strap be moved back and forth for the length adjustment.

FIG. 17 shows a vertical, horizontal, cross-cut view of a buckle piece shown at FIG. 16. In this figure the lower flat piece, LP, is shown and its lower surface consists of attachment means, ATM.

The upper surface of the upper piece, UP, has hook-fastener attachment means, ATM2, that allow the end of the strap to be attached to it on a detachable, re-attachable basis.

The lower surface of the upper piece, UP, has the spin, SPIN. At the time of use the strap will be pulled in the direction of the straight arrow, and then the unit will be snapped and the rest of the strap will make a U-turn in the direction of the curved arrow to attach to the attachment means of the upper surface of the upper piece, UP.

FIG. 17A shows a vertical, longitudinal, cross-cut view of a buckle piece shown at FIG. 16. In this figure the lower flat piece, LP, is shown and its lower surface consists of attachment means, ATM. The upper piece, UP, is hinged to the lower piece, LP, at hinge, HI. The upper surface of the upper piece, UP, consists of attachment means, ATM2, the spin, SPIN, is shown at the lower surface of the upper piece, UP, and the snap, SNAP, is also shown.

FIG. 18 shows the front view of an end unit, designed to allow the length of the strap to be adjusted. This unit has a rectangular, flat base, BASE, made from a layer of fabric with a zone of hook-fastener attachment means on its right side, ATM2, placed on its upper and lower surfaces. Here, the upper zone of attachment means, U-ATM2 is shown on the right side. A similar zone on the left side is made with a layer of adhesive on it, shown at ADH, at FIG. 18A, which is protected by a protective cover, PC. The inner edge of the protective cover is shown at BPC. The lower surface of the base in the right side also has attachment means, L-ATM2, best shown at FIG. 18A. This unit gives significant advantage and will allow the length of the strap to be adjusted for many units such as the heel and shoulder and other units.

Importantly, instead of U-ATM2 the unit may have a zone of adhesive to allow the fabric to attach to this zone. The adhesive zone will be protected by a protective cover similar to the piece shown at, PC.

At the time of use:
1. Initially this piece will be attached in a proper position to the body of the outer surface of the support, SUP.
2. Then the strap will be pulled to attach to the ATM2 zone of this piece, which will be possible due to the capability of the strap.
3. When the proper length of the strap is decided, then the extra piece of strap will be cut along the left border of the upper attachment means, ATM2 on the upper surface of this unit. Please note that at this point the strap is attached to hook-fastener attachment means, ATM2, from the upper surface of this piece.
4. Then the user will remove the protective cover, PC, and adhere the lower or base of this piece to the upper surface of the strap through use of the adhesive layer.

This combination will make:
a. The free end of the strap have a neat cut.
b. The combination make a zone of hook-fastener, attachment means, ATM2, in the lower surface of the free end of the strap that will be used to attach the free end of the strap to the outer surface of special supports that will accept this end. This will be very useful in units for use in various areas, such the heels and shoulder, etc.

The advantage of this unit is that allows a one-size unit to be used as a universal unit or will allow a better adjustment of the length of the straps.

FIG. 18A shows the cross cut view of the unit shown at FIG. 18. In this picture the unit has base, BASE, made from a layer of fabric, with a zone of hook, fastener, attachment means, ATM2 on its upper and lower surfaces shown in the right side. On the upper surface of the left half of the base, the fabric has a layer of adhesive, ADH, that has a protective cover, PC, on it. At the time of use this piece will be attached to the top surface of a matching support by virtue of the lower attachment means, L-ATM2. The elastic strap will attach to the upper attachment mean, U-ATM2, of end unit and with adjustment, proper length of the strap will be known and then the extra piece will be cut along the left border of the upper attachment means which is on the border of the protective cover. Then the user will remove the protective cover, PC, and adhere the base to the upper surface of the strap. This will make a clean-cut side and the combination will make a zone of attachment means, ATM2, on the lower end of the strap that will be used to attach the end of the strap to the surface of the units for use in the heel and shoulder, etc.

Again please note that, instead of U-ATM2 the unit may have a zone of adhesive to allow the fabric to attach to this zone. The adhesive zone will be protected by a protective cover similar to the piece shown at, PC.

FIG. 18B (also note FIG. 18C) shows the front view of an end unit shown at FIG. 18 that is placed on a support, SUP. This support has a non-stretchable body with an outer surface made from a layer of loop-fastener, attachment means, ATM1, its inner surface being a soft lining that stands on the skin, and a thin layer of foam sandwiched in between. The strap, STR, is attached to the right border of the support. The outer surface of the left border of the support, SUP, has a long, narrow zone of hook-fastener attachment means, ATM2. The end unit piece is attached to the surface of the support, SUP, due to the attachment means, ATM2, in its lower surface, this part is shown better in FIG. 18C.

FIG. 18C shows the vertical, cross-cut view of the support, SUP, shown at FIG. 18B with an end piece close and parallel to it. The strap is not shown. The upper layer of the support is a loop-fastener attachment means, marked at ATM1, and its lower surface is a soft lining, LIN, the layer of foam, FOAM is in between. The end unit is shown on top of the surface of the support, SUP, and consists of a base, BASE, made from a layer of fabric or a polymer. A zone of hook-fastener attachment means, ATM2 is on its upper surface, U-ATM2, and another zone of hook-fastener attachment means is in the lower surface of this piece but is not marked. The other segment of the base, BASE has a layer of adhesive shown at ADH, that has a protective cover, PC, on it.

The method of use:
1. Initially the end unit will be attached to the body of the outer surface of the support, SUP, due to its loop, fastener attachment means, ATM2.
2. Then the strap will wrap around the limb and be pulled to attach to the zone of ATM2 shown on the left border of the support, SUP. This occurs due to the strap's own capability that functions as a loop-fastener attachment means. This step allows the length of the strap to be decided.
3. After the proper length of the strap is decided, it will be further to attach to the upper attachment means, U-ATM2, of the end piece.
4. The extra strap will be cut along the right border of the upper attachment means, U-ATM2, on the upper surface of this piece. Please note that at this point the strap is attached to the U-ATM2 from the outer surface of this piece.
5. Then the user will remove the protective cover, PC, and adhere the base, BASE to the upper surface of the strap by use of the adhesive layer.

At this point the lower surface of the end piece is attached to the upper surface of the support by virtue of the lower attachment means, ATM2 and importantly, its position may be further changed by moving it back and forth on the support.

FIG. 18D shows the vertical, cross-cut view of a mating piece that allows the unit shown at FIG. 18 to be used with a support that is made from a material, such as vinyl, that does not have the loop-fastener means on its own surface. This piece has an outer surface made from a loop-fastener attachment means, ATM1, and its lower surface has a layer of adhesive shown at ADH covered with a protective cover, PC, on it.

The method of use:
1. Initially the protective cover, PC, of this mating piece will be removed and the unit adhered to the outer surface of the support, SUP.

This will modify the vinyl or similar supports, and allow the end piece shown at FIG. 18 to be attached to the loop-fastener attachment means, ATM1, of this piece to function.

FIG. 19 shows the general view of a support unit designed for use in the head. This unit consists of two similar pieces of support units, SUP-A and SUP-B, that will be attached to each other by use of straps, H-STR and C-STR. The supports have a trapezoid body as shown at SUP-A, with a wider, upper area for the head area and a narrower, lower area for placement on the chin area. Importantly, this support has a laminated body with an outer layer made of loop-fastener attachment means, ATM1, an inner layer which is a soft, fabric, lining to contact skin and a layer of foam in between. In the units shown here, the outer surface of the support, SUP, has two zones of long and narrow hook-fastener attachment means, ATM2, that allow the body of a strap made from lycra with a smaller support on its end almost similar to the one shown at FIGS. 1-4 to be attached to it on a detachable, re-attachable basis. This strap, shown in more detail at FIG. 20, will attach to the unit shown at FIG. 19 on a detachable, re-attachable basis. This is important since the body of this particular strap allows such an attachment, which will keep the unit stable and prevent it from moving.

The upper border of the trapezoid support, SUP-A, has two stretchable straps made from Lycra, shown at H-STR. These straps attach the head areas of these two support pieces together on a stretchable, detachable and re-attachable basis. The free ends of these two straps have a hook-fastener attachment means, ATM2, that allow the ends of these straps to be attached to the outer surface of the other support, SUP-B, on a detachable, re-attachable basis.

The lower border of the support, SUP-A, for the chin area also has two stretchable, but narrower, straps made from Lycra, shown at C-STR, that attach the chin areas of the supports SUP-A AND SUP-B, together on a stretchable, detachable and re-attachable basis. The free ends of these two chin straps, C-STR, have small zones of hook-fastener attachment means, ATM2, that allow the ends of these straps to be attached to the outer surface of the second support, SUP-B, on a detachable re-attachable basis.

The second support, SUP-B, has a similar body, except that it does not have the H-STR and C-STR straps, since the these straps will be attached to it on a detachable, re-attachable basis.

FIG. 20 shows schematically the side view of the unit for the head shown at FIG. 19. In this figure, the body of the support, SUP-A, is shown made of a laminated piece with an outer surface made from a layer of loop, fastener attachment means, ATM1, an inner layer made from a layer of soft fabric lining, LIN, and a layer of foam, FO, which is sandwiched between. The elastic strap for the head is shown at H-STR and the elastic strap for the chin is shown at C-STR both of these have zones of attachment means, ATM2.

FIG. 21 shows schematically the general view of a complementary strap for use with the unit shown at FIG. 19. This strap is similar to the strap shown at FIGS. 1-4. Basically, this shows a long, stretchable strap, STR, that is attached to a support, SUP. The support has a zone of hook-fastener, attachment means, ATM2, on its front surface that allows the body of strap, STR, to attach to it on a detachable, re-attachable basis. The rear surface of this support, STR, may also have another zone of hook-fastener attachment means, ATM2, (which cannot be seen in this view) that allows the support, SUP, from this strap to attach to the outer surface of the support, SUP, for the head and chin on a detachable, re-attachable basis. Please note that the support for the head and chin, has a laminated body with an outer layer made from a layer of loop-fastener attachment means.

The free end of the strap, STR, shown on the left side of this figure has an adhesive piece similar to one shown at FIGS. 1-4 that allows the end of this strap to be attached to the outer surface of the strap, STR. This can also have a zone of hook-fastener attachment means, ATM2.

This combination of strap and head and chin support makes a valuable unit, since it allows a very stable and versatile unit for use for the wounds of the head and face.

This unit allows the head straps, H-STR, for the head site to be opened to adjust the size or tension of the unit or for the examination of the wound site. Also the chin straps, C-STR allow the size and the tension of the unit to be adjusted, as well. The strap, STR, goes horizontally around the head and allows the size of the strap and thus, the horizontal tension to be adjusted. Also, it allows the wounds in the occipital or the frontal part of the head to be checked.

FIG. 22 shows schematically the general view of a support unit for the shoulder. This unit has a non-stretchable support unit shown as ARM-SUP, that covers the outer side of the arm. This support has laminated body with an outer layer made from a loop-fastener attachment means, ATM1, and an inner layer which is a soft fabric lining to contact skin and a layer of foam/sponge in between. In the units shown here, the outer surface of the support, SUP, will have at least two long and narrow zones of hook-fastener attachment means, ATM2. This allows the body of an arm strap, ARM-STR, made from LYCRA (™), with a smaller support on its free end, almost similar to the one shown at FIGS. 1-4 to be attached to the ARM-SUP, the strap, ARM-STR, is designed to wrap around the upper arm and attach to the surface of the ARM-SUP on a detachable, re-attachable basis.

Another wider, elastic shoulder strap, SH-STR, is also made from LYCRA (™) and is attached to the upper border of the ARM-SUP. The shoulder strap, SH-STR is designed to cover the shoulder and keep the dressing securely on it. Importantly, the stretchable body of this strap allows the shoulder to move easily. The shoulder strap, SH-STR, has two support pieces of its own that cover the front and rear (FR-SUP and RE-SUP) upper part of the chest. These two supports are made from the same material as the arm support, ARM-SUP, and also have zones of hook-fastener attachment means, ATM2, on their front surfaces. At the time of use, the FR-SUP is placed on the front of the upper chest and the RE-SUP placed on the rear surface of the chest on the user's back. A strap shown at FIG. 23 goes in front of the chest and wraps in the armpit of the opposite arm, with one free end of the strap attaching to the outer surface of the FR-SUP and the other to the outer surface of the RE-SUP on a detachable, re-attachable basis.

A piece of support, shown as axillary sup, AX-SUP, in FIG. 23 and made from same laminated material will go under the armpit and function as a stabilizer, preventing the strap from curling.

Method of use:

1. The body of arm strap, ARM-STR, will wrap around the arm and first attach to the attachment zone, ATM2, from the arm-support, ARM-SUP, due to the special property of the strap that functions as the loop-attachment means. Then the hook-fastener attachment means, ATM2, of the free end of the arm strap, ARM-STR, will attach to the outer surface of the arm support, ARM-SUP, on a detachable re-attachable basis. This will hold the arm support, ARM-SUP on the outer surface of the arm in a stable, comfortable fashion.
2. The shoulder straps will be next be wrapped on the shoulder area; its front support, FR-SUP, being placed on the front of the upper chest and its rear support, RE-SUP, placed on the rear surface of the chest behind the user.
3. One free end of strap STR shown at FIG. 23 will be placed on the front of the chest and be pulled to a comfortable tension, wrapped in the armpit of the opposite arm.
4. In the armpit area, the strap, STR, will be attached to the outer surface of the axillary sup, AX-SUP shown in FIG. 23 on a detachable, re-attachable basis. Please note that the axillary sup, AX-SUP, is made from a laminated material and has a zone of hook-fastener attachment means on its own outer surface that allows the attachment of the strap, STR, to its body occur. This axillary sup, AX-SUP functions as a stabilizer and prevents the strap from curling.
5. Then the free end of the strap, STR, will be pulled in the back of the chest, and be attached to the outer surface of the RE-SUP on a detachable, re-attachable basis.

This method and means makes a stable, comfortable unit for the shoulder joint. Importantly, one end of the strap for the chest will be attached first, and a buckle system as shown at FIGS. 16-18 (or similar units) may be used to adjust the length of this strap. FIG. 23 shows schematically the general view of the strap for the shoulder support unit shown at FIG.

22. In this figure the body of the axillary support, AX-SUP, is shown. The front/outer surface of this support has a zone of hook-fastener attachment means, ATM2, which is under the strap, STR, and cannot be seen in this view. Both free ends of the strap, STR, have zones of hook-fastener attachment means, ATM2. As mentioned above, one free end of this strap will be attached to the front of the front support, FR-SUP. The strap will then be wrapped around the chest, and go under the opposite armpit to have its other free end attach to the outer surface of the RE-SUP on a detachable, re-attachable basis. The body of the axillary support, AX-SUP, covers the axillary area and will keep the strap, STR, in proper position, simultaneously preventing it from curling.

FIG. 24 shows schematically the general view of a support unit for the ankle. This unit also consists of a non-stretchable, support, shown at, HEEL-SUP, that stands on the front or the upper surface of the ankle. The heel support, HEEL-SUP is made from the laminated material with the outer surface made from a layer of loop attachment means, ATM1, an inner surface, a soft lining to contact skin with a thin layer of foam in between. The outer surface of the support has a zone of hook-fastener, attachment means, shown at ATM2-HS. An elastic strap, made from LYCRA (™) shown at HEEL-STR, is attached to the right border of the HEEL-SUP. The free end of this strap has a zone of loop-fastener, attachment means, ATM2-H-ST. This strap will wrap around the heel and will attach to the outer surface of the heel support, HEEL-SUP, on a detachable, re-attachable basis. The two bands BAND-A and BAND-B are similar to the bands shown at FIGS. 1-2, except that they are located at the same site as the main strap. These bands will go around the ankle on each side and will attach to the zone of the hook-fastener, attachment means, ATM2-HS from the support HEEL-SUP on a detachable, re-attachable basis due to their own property. They may have their own smaller zones of hook attachment means, ATM2-A and ATM2-B as shown, which may be attached to the outer surface of the HEEL-SUP. Importantly, the heel strap, HEEL-STR, and the bands BAND-A and BAND-B are made from a special material (LYCRA. ™) that has a loop fastener function and allows these pieces to attach to the hook attachment means, ATM2-HS, on a detachable, re-attachable basis. This facilitates the application of this unit very significantly, and has a very significant importance.

Method of use.
a. The user places the heel-support, HEEL-SUP, on the front/upper surface of the heel.
b. The user wraps one of the bands, BAND-A or the BAND-B around the ankle joint in its upper part and attaches it to the hook attachment zone, ATM2-HS from the heel-support, HEEL-SUP, on a detachable, reattachable basis. This will hold the support in place and allows further attachments.
c. The user wraps the second band, BAND-B or the BAND-A around the lower part of the ankle joint and attaches it to the hook attachment zone, ATM2-HS from the heel-support, HEEL-SUP, on a detachable, reattachable basis. This will hold the support in place even more stable and allows the attachment of the heel strap, HEEL-STR.
d. The heel strap, HEEL-STR, will be wrapped around the heel and it will be first attached to the attachment zone, ATM2-HS from the heel-support, HEEL-SUP, due to the special property of the body of strap that functions as the stretchable, loop attachment means. Then the hook-fastener, attachment means, ATM2-H-ST, of the free end of this strap will attach to the outer surface of the heel support, HEEL-SUP on a detachable re-attachable basis.

This method makes a comfortable, sturdy unit on the heel area. The elastic heel strap, HEEL-STR wraps around the heel comfortably, and allows the ankle joint to move freely.

Importantly, it is possible to use these units without the use of the bands, BAND-A or the BAND-B, therefore, some units may not have the bands, BAND-A and BAND-B or the unit may only have one of such bands. In models which do not have bands, the steps b and c from the method of use will be omitted.

Importantly, the use of end units shown at FIGS. 18-18A will be quite helpful with this unit, since it will allow the length of the heel strap to be chosen.

FIG. 25 schematically shows the general view of a support unit for the elbow. This unit has two pieces of a non-stretchable, support shown at ELBO-SUP1 and ELBO-SUP2 that are designed to stand on the front part of the elbow, above and under the elbow crease. These supports are made from type II support means which have a laminated body with a layer of loop-fastener attachment means, ATM1, on its outer surface, as mentioned earlier. The outer surface of these supports has a zone of hook-fastener attachment means shown at ATM2, on its left border. A wide, continuous elastic strap, made from LYCRA, (™) shown at ELBO-STR, is attached to the right border of the elbow supports, ELBO-SUP1-2. The elbow strap, ELBO-STR, has two free ends, F-END1 and F-END2. The inner surface of these free ends has a zone of hook-fastener attachment means, ATM2 (this can be a double sided, hook-fastener, attachment means,). This strap is designed to wrap around the elbow and have its free ends, F-END1 and F-END2, attached to the outer surface of the elbow supports, ELBO-SUP1 and ELBO-SUP2, on a detachable, re-attachable basis.

Importantly, the body of the strap, STR, will first attach to the attachment zone, ATM2, from the outer surface of the support units, ELBO-SUP1 and ELBO-SUP2. This attachment is possible due to the special property of the elbow strap, ELBO-STR, which functions as the stretchable, loop-fastener attachment means. Then the attachment means, ATM2, of the free ends of the strap, F-END1 and F-END2 will attach to the outer surface of the supports, ELBO-SUP1 and ELBO-SUP2 on a detachable, re-attachable basis. This method makes a comfortable, sturdy unit for the elbow joint. Importantly, this leaves the front of the elbow open to bend freely.

Method of use.
1. The ELBO-SUP1 will be placed on the front of lower arm above the elbow crease.
2. The upper part and the upper end of the ELBO-STR, will be wrapped around the elbow joint in the lower arm area above the elbow crease and its upper end piece, F-END1, will be attached to the outer surface of the support, ELBO-SUP1 on a detachable, re-attachable basis.
3. The lower part and the lower end of the ELBO-STR, along its main body, will be wrapped around the elbow joint in the elbow joint, upper forearm area under the elbow crease and its end piece, F-END2, will be attached to the outer surface of the support, ELBO-SUP2 on a detachable, re-attachable basis.
4. At this point the user will be able to adjust the end pieces further to position the unit and change the tension of the strap by further adjustment of the free ends of the strap, F-END1 and F-END2 to make an effective, yet comfortable, unit.

Importantly, the body of the strap, STR, will first attach to the attachment zone, ATM2, from the support unit. Such an attachment is possible due to the special property of the body of the strap that functions as the stretchable, loop-fastener attachment means. Then the attachment means, ATM2, of the free ends, F-END1 and F-END2 will attach to the surface of the supports ELBO-SUP1 and ELBO-SUP2, on a detachable, re-attachable basis. This method makes a comfortable, sturdy unit for covering the elbow-joint area. Importantly, this leaves the front of the elbow open to bend freely.

FIG. 26 schematically shows the general view of a support unit for the hip. This unit consists of one non-stretchable, support unit shown at SUP, that is placed on the hip/joint area. This support has zones of hook-fastener attachment means, ATM2, on its front/outer surface, that allow a strap with a loop-fastener attachment means, ATM1, to be attached to it on detachable, re-attachable basis. Alternatively, this support may have a series of D-Rings shown at D.RIN, on its sides in order to allow the free end of the straps to go through, make a U-turn, and attach to their own outer surface on a detachable, re-attachable basis. This method allows the length of the straps to be adjusted. In the models made, the applicant has used three straps with these units. This unit may have another support unit to be placed on the other hip joint in order to hold the straps in a stable position. A pad will be placed under the support for a better result.

FIG. 26B schematically shows a support unit for the hip that consists of hinging two support pieces so that it allows the person to bend the hip joint. In this view, the first support made from a non-stretchable piece, is shown at SUP1 and hinges to the second support, SUP2, at hinge HIN. The outer surfaces of the support pieces have zones of hook-fastener attachment means, ATM2. These zones are not shown for the support 2, SUP2 to prevent a crowded Figure. This allows a series of the straps made from loop-fastener attachment means, ATM1, to be attached to the supports on a detachable, re-attachable basis. This support also may have a series of D-Rings on the sides. The supports shown at these two figures will hold a cushion pad made from a foam covered with fabric that will be attached to the support unit on a detachable, re-attachable basis. This allows the cushion to compress the wound area.

FIG. 26C schematically shows a protective support unit for the chest. This is designed to keep clothing away from the wound site of various forms, particularly after open-heart surgeries. This unit prevents clothing from touching the chest wound, and has a rather rigid and clear support piece that will be held away from the chest wall by use of walls made of foam pads. The outer surface of the support, SUP, has zones of hook-fastener attachment means, ATM2, on its upper and side borders. This allows the straps made from loop-fastener attachment means, ATM1, to be attached to it on a detachable, re-attachable basis. These straps of this unit consists of following:

1. A vertical strap that hangs on each side of the neck, both end pieces attaching to the zone of the hook-fastener attachment means, ATM2, which is located on the upper border of the support.
2. One or two horizontal straps wrap around the chest. Their end pieces will attach to the zone of the hook-fastener attachment means, ATM2, which is located on the borders of the support on its sides. Commonly, one strap around the neck and two from the chest area are used with this unit.

FIG. 26D shows schematically the vertical, cross-cut view of the unit shown at FIG. 26C. In this figure the body of the support, SUP, is shown and has a curve that keeps it away from the wound site. The upper/outer surface of the support has hook-fastener attachment means, ATM2, on its right and left borders. The lower surface of the support has two foam pads, FOAM, that will keep the chest support, SUP, away from the chest wall.

FIGS. 27-28 schematically shows the front and rear view of a support unit for the ear. The front view is shown at FIG. 27 and is rotated 180 degrees to show its rear image that looks somewhat similar to its mirror image at FIG. 28. This unit has a support, SUP, made from a laminated body, with an outer surface made of a layer of loop-fastener attachment means, ATM1, and an inner, soft lining for contacting skin with a thin layer of foam in between. In the process of use this support will fold along a line, FO-LIN. The body of the support, SUP, on the right side has an oval opening, O-OP, with a cut, CUT, on its lower pole. This opening allows the support to be placed around the base of the ear and prevent it from moving. The rear/outer surface of the support, SUP, on the left side has two zones of hook-fastener attachment means, shown at ATM2. A wide, elastic strap, made from LYCRA, (™) and shown at HE-STR, is designed to wrap around the head. This strap is attached to the body of the support, SUP, along the dotted-line, D-LINE. Importantly, the attachment line, D-LINE, is intentionally away from the edge of the support. This allows the band of attachment means, B-ATM2, to attach to the rear surface of the support, SUP, near the D-LINE, so that the strap will finally wrap over this band.

At the time of use:
A. The oval opening, O-OP of the body of the support, SUP, will be placed around the base of the ear via the cut, CUT. This method will prevent the movement of the support after placement.
B. The rear half of the support, SUP, shown at the left side will fold along the folding line, FO-LIN, and cover the ear. The free borders of these two pieces will be held together by attaching the band of the attachment means, B-ATM2, to the rear surface of the support, SUP, adjacent to the D-LINE. The folded support holds the dressing of the ear on it securely.
C. Then the head strap, HE-STR, which is made from Lycra, will wrap around the head horizontally, on the front of the head, the temporal side and the occipital area respectively. So that ultimately, its free end will attach to the outer surface of the folded support, SUP, by use of the two zones of the attachment means, ATM2.

This method makes a secure and simple means of holding the dressing on the ear, which is commonly difficult. The body of the support may be made to have more foam and be thicker, or also to have a more protective, non-compressible body to avoid compression of the ear. The strap may also have a piece to go vertically and use the method shown for the head support.

Importantly, a small envelope made from fabric may be used to go over the wound of the ear and be held in place by this unit.

FIG. 29 schematically shows the side view of the unit shown at the previous two figures. This figure shows the support, SUP, the zones of the hook-fastener attachment means, ATM2, on its lower surface, (only one zone is marked), the folding line, FO-LIN and the head strap, HE-STR. Note that the point of the attachment of the head strap, HE-STR to the body of the support, SUP, which is marked at D-LINE is intentionally away from the very edge of the support. This is to allow the band of attachment means, B-ATM2 to attach to the rear surface of the support, SUP, near the D-LINE. This special design allows the head strap, HE-STR, to wrap over this band.

FIG. 30 schematically shows the general view of a support unit for the Pacemaker-Defibrilator Wound. This unit consists of a non-stretchable support unit, SUP, that stands on the front of the upper chest in the subclavian area and holds a pad, PAD, on the wound site. The pad, PAD, is attached to the inner surface of the support, SUP, on the upper half area of the support, by a hook-fastener attachment means, ATM2. The body of this support is also made from a laminated body with an outer surface made from a layer of loop-fastener attachment means, ATM1, and an inner soft lining for contact skin, with a thin layer of foam in between. The body of the support on its upper half has a thicker body made from a folded support. In this area the support makes a U-turn and attaches to its own body, shown better at U-SUP at FIG. 31. Thus, this part has a body with a surface made of a loop-fastener attachment means, ATM1, on both sides. The support and attached pad will be held in the upper shoulder area by use of two straps made from a laminated layers of loop-fastener attachment means, ATM1, both its outer and its inner surfaces with a thin layer of foam in between. The straps consist as follows:

a. A horizontal strap shown at H-STR that is designed to wrap around the chest and attach to the outer surface of the support, SUP, by use of a zone of hook-fastener attachment means, ATM2. This is located on both ends of the strap or by use of an extra piece of a double-sided ATM2.

b. A vertical shoulder strap, S-STR, that covers the shoulder. The rear end of this strap makes a U-turn around the horizontal strap, H-STR, shown at U1, to attach to the surface of its own body. This will in turn keep the horizontal strap H-STR and the shoulder strap, S-STR, attached to each other on an adjustable basis, and is shown best at FIG. 31A.

c. The front portion of the shoulder strap, S-STR, stands in front of the support, SUP, and may attach to it by use of pieces of double-sided hook-fastener attachment means, ATM2. The strap then moves down, and will wrap around the patient's wrist, where it makes a U-turn and moves up to attach to the rear surface of its own body as shown at U2 FIG. 31A.

This unit:

1. Provides a compression to the wound site and prevents hematoma.
2. Holds the wrist of the patient in position and prevents it from moving.
3. Prevents other objects from reaching the wound site and causing pain.

Importantly, the size, shape and the make up of the pads may vary. Also the nature of the straps may vary; the straps may be made to be:

1. Non-stretchable
2. Stretchable, elastic material
3. Combination of non-stretchable and stretchable materials.

The elastic straps may have their own attachment property or they may have pieces of attachment means attached to their body.

Importantly, in these units the body of the support is primarily made from a material that has an outer surface made from a layer of loop-fastener attachment means ATM1 and its inner surface is a soft lining that would stand on the skin, with a thin layer of foam in between. This allows the shoulder and horizontal straps to be attached to the surface of the support in any area by placing a piece of a double sided hook-fastener attachment means, ATM2, between them. This design and method makes these units more versatile and stable.

FIG. 31 schematically shows the side view of the support unit shown in FIG. 30. In this figure the support, SUP is shown with the upper body of the support made from a folded support so that the upper half has an outer surface made of a loop-fastener attachment means, ATM1, on both sides as shown at U-SUP. The pad, PAD is attached to the front surface of the U-SUP. The rear surface of the pad is specified at S-PAD and may have a layer of loop-fastener attachment means, ATM1. The pad, PAD, is attached to the inner surface of the support, U-SUP, through use of attachment means, ATM2.

FIG. 31A schematically shows the side view of the arrangement of the straps. In this view the shoulder strap, S-STR, stands on the shoulder (not shown). The rear segment of the strap makes a U-turn, U1, around the horizontal strap, H-STR, and attaches to its own body by use of ATM2, on a detachable, re-attachable basis. This keeps the horizontal strap, H-STR, and the shoulder strap, SSTR, attached to each other on an adjustable basis.

The front segment of the shoulder strap, S-STR, stands in front of the support (not shown) and may attach to it by use of pieces of double-sided ATM2 patches. It moves down in front of the chest, the free end of the strap making a U-turn, U2, around the wrist, WR, of the patient and attaches to the front surface of its own body by the zone of the ATM2 at its end.

FIG. 32 shows a support unit similar to the unit shown in FIG. 30, except this unit has two complementary support pieces. The first support stands in the front of the chest and is referred to as the Front Support, F-SUP, and the second support stands on the back of the chest and is referred to as the Rear Support, R-SUP. The Front Support, F-SUP, stands on the wound site and will be kept in place through use of a strap in the right side, R-STR, another strap on the left side, L-STR and a vertical strap, V-STR that will come together and attach to the surface of the Rear Support, R-SUP. The free ends of these straps have pieces of hook-fastener attachment means shown at ATM2 that attach to the surface of the R-SUP, made from the laminated body with an outer surface made of a layer of loop-fastener attachment means, ATM1, with an inner soft lining and layer of foam in between. The outer surface (the side that does not come in contact with the body site) of the support also has zones of hook-fastener attachment means, ATM2. This allows the body of the strap to attach to these attachment means on a detachable, re-attachable basis. Thus, the rear support, R-SUP, will in fact act as a catalyzer, allowing the ends of the straps to attach to each other easily. Alternatively, the free ends of the attachment means may be attached to each other through use of double-sided loop or hook fasteners, ATM1 and ATM2. The dressings or pads may be placed under the front or rear support.

Importantly, this model makes the process of the dressing easier in some cases by preventing a crowded area in front.

Importantly, the front support may have a body made of stretchable or non-stretchable layers.

FIG. 33 shows the general view of a support unit similar to the unit shown at FIG. 6, except this unit is modified for use in the arm and forearm to allow the wound dressing and/or compression of limb in these areas. This unit allows a secure and easy dressing without the need for adhesive tapes. In this model, the support, SUP, has a long, rather rectangular shape with cuts in its sides, CUT, for composure on the elbow crease. The support of this unit stands on the front of the arm and forearm, or on its rear. The support, SUP, has a long zone of hook-fastener attachment means, ATM2, on its left border that allows pieces made of loop-fastener attachment means, ATM1, or a strap made from lycra to be attached to it on a detachable, re-attachable basis. The right border of the support unit, SUP, is attached to a series of straps: STR-A, STR-B that will wrap around the arm area and STR-C, STR-D and STR-E, which are designed to wrap around the forearm. These straps are attached to the border of the support, SUP, on a permanent basis, although importantly, they may be attached to the support on a detachable, re-attachable basis as shown for the leg support. These straps are properly sized to be wrapped around the arm from the axillary area to the elbow-joint area. Importantly, this unit may have three straps for the arm part as well or more.

The straps for the forearm will be placed in the upper, mid- and lower forearm.

These straps may be attached to the support, SUP, by use of pieces of loop-fastener attachment means, ATM2, at their ends. Similar to the leg straps, this method allows the unit to be used for dressing, supporting and compressing the arm and forearms in a very practical, adjustable manner. In this model the straps are also made from one or two layers of LYCRA (™) and the support means, SUP, is made from a non-stretchable, clear vinyl, or from a laminated body with an outer surface made from a layer of loop-fastener attachment means, ATM1, and an inner layer made from a soft lining that stands on the skin with a thin layer of foam in between. It may also be made from any other materials such as fabric or any other man-made materials. The support may have openings to allow sweat and air to move and also allows a gauze pad or a long, removeable layer of lining shown at LIN, in FIG. 6A or a pad to be placed under it to prevent irritation, place pressure, and allow the application of medication, etc. This unit allows the placement of electrical leads in the area to allow a programmed stimulation of the arm muscles and tissues for reasons such as the prevention of muscle weakness or prevention of phlebitis.

Importantly, the narrow area of the support between two cuts, CUT, on each side will function, to.
1. Keep the lower part of the support in place and prevent it from falling.
2. It will function as a hinge and allows the lower segment of the support to rotate in different directions (compared to the upper part) without being disconnected from the upper segment.

The advantages of this unit are that:
1. It makes the placement of this unit with one hand possible.
2. It is possible to adjust the tension of each strap individually. This allows the pressure in each segment of the arm or forearms to be modified easily, without disturbing the whole unit. This is not possible by a commonly used wrapping system.
3. The arm and the elbow to function easily due to presence of the cut in the support.
4. The arm and elbow to be hung from a stand in order to facilitate the drainage of the tissue. 5. This unit can be placed and removed rather easily. Since placement of only one strap holds the support in place and allows the other straps to be placed. Then by adjusting each strap the whole unit can be adjusted.
6. Placement of a lining which may be attached to the support, SUP, of the unit on a detachable, re-attachable basis. This allows the lining to be washed or exchanged.

The lower part of this figure shows a piece that allows this unit to be extended to the hand area and be attached to an automatic height elevator shown at FIG. 34. This part shows a support for hand, SUP, that stands on the rear of the hand, and will be attached to the lower extension of the support of the arm-elbow by the hook-fastener attachment means, ATM2, in the upper end of the hand support. The straps of this support will wrap around the palm and fingers and will attach to the rear surface of the body of the hand support. The hook in its lower end allows this support to be attached to the hook, HOOK, of the remote-controlled elevator from FIG. 34.

Please note that the straps shown in the upper part of the picture are not attached to each other and are separate, so that they can be attached to the support individually.

Importantly, the straps of these units may be attached to the support unit independently by having both their ends attached to each side of the support on a detachable, re-attachable basis.

Importantly also, the straps may be made from a continuous layer of LYCRA, (™), to allow a uniform coverage of the area. One continuous layer of the strap is attached to the border of the support without having a cut or space in the body of the strap in this side.

However, their very end pieces will be separate to allow easy placement. An example of this model is shown for the leg at FIG. 6C and is not repeated here to avoid a lengthy application.

FIG. 34 shows schematically a limb elevator which allows a limb to be lifted by being raised from below or to be pulled up by being hanged to its hooks, HO. This unit consists of a remote controlled electrical motor (not shown), that rotates a wheel, RW which is secured on a pole, PO, that stands on a base, BA. The unit has a limb stand, LS, which has a flat surface that allows one or two limbs to be placed on it. The lower surface of the limb stand, LS, has hooks, HO that allow a limb support to be hooked to it and be raised when the base is moved up. The base holds a pipe which can move up and down over a central shaft, CS. The outer surface of this pipe of the limb stand, LS has a indented zone, EP which engages with the teeth of the rotating wheel, RW. By utilizing this method the rotation of the wheel will move the pipe up and down for elevation of the limb stand, LS. The central shaft, CS and the pole, PO stand on a base, BA. A remote controller, RC, controls the movement of the electrical motor from a distance. The elevation of the hands or feet by this unit will allow the hydrostatic pressure to be used in a positive way to reduce the swelling of the tissue in the limb. The applicant believes that this will be useful in cases such as; breast removal, or swelling of the arms or legs due to vascular problems.

Importantly, this unit may be modified for placement in the lower bed area, which will allow the user to place his/her leg/s on the limb stand and to have them raised.

The limb stand, LS of this unit will be moved down to stand on the bed surface so that the user can place his/her feet on the top of the limb stand, LS. Then the limb stand, LS will move up by use of the remote controller, RC. Importantly, this model not only allows the limbs to be moved up, but its design allows the limbs to be hanged in its hook, HO and to be moved up and down as desired.

Many other methods such as jack type machinery may be also used to elevate the limb stand, LS. An extension can be attached to this unit for the height control. Importantly, the base of this unit may be used:
1. By attachment to the bed structure.
2. It can be moved around and may have wheels of its own.

FIG. 34A shows schematically a unit that allows a limb to be placed on it and be lifted by the elevator shown at FIG. 34. This piece will tolerate the weight of the limb and prevent from discomfort of the joints.

This unit consists of the following pieces.
a. A flat base that will be placed either under a bed or the body of the user, is schematically shown a body rest, BR. This piece allows the body to rest on it, and is hinged to a cradle, AR that allows a limb to be placed on it.
b. The cradle, AR, is hinged to the body rest from one end and has an extension for the hand to rest on it shown at, HR.
c. The hand rest, HR, has a hook, HO, that allows it to be hanged on the HR, of the elevator.

Method of use.
1. The person attaches the hook, HO, to the elevator.
2. The user places the body rest, BR, of this unit under his/her body, for the shoulder or the hip to be on the hinge area.
3. The user places his or her arm on the cradle, AR, and the hand on the hand rest, HR, a series of straps may help to keep these limb parts in place.

This unit may be made from a rigid cradle or a cradle made from a non-stretchable fabric. In either case, it will have proper cushioning to make a comfortable bed for the limb.

FIG. 35 shows the general view of a support unit similar to the unit shown at FIG. 6 and 33, except this unit is modified for use in the thigh area. This unit has a support, SUP, which has a long, rather rectangular shape with cuts, CUT in the sides as shown to stand on the hip joint and functions as a hinge. The upper part, above the cut, CUT, of the support, SUP, is for placement on the waist and its lower part will be placed on the lateral side of the thigh. The cut, CUT, will allow the lower part of the support, SUP, to rotate in the different directions without being disconnected from the upper part.

The support, SUP, has a series of straps attached to it. The first strap functions as the belt and is marked at, BELT. This will hold the support and prevent it from falling. Other straps, STR-1, STR-2, and STR-3, are attached to the body of the support on a permanent basis in one side. These straps will individually wrap around the thigh and attach to the hook-fastener, attachment means, ATM2, of the support due to their own properties which allow such an attachment due to the presence of the hook fastener attachment means, ATM2, at the free ends of the strap, and on a detachable, re-attachable basis (as shown for the leg support). These straps are properly-sized to wrap around the thigh from the groin area to the upper knee. Importantly, the support, SUP, may have an extension to cover the knee area with a strap going around the knee.

Importantly, the extension, shown at EXT, will allow the attachment of this unit to the support of the leg support.

Importantly, the effective length of these straps may be modified by use of the methods and means explained in different parts of this application. Similar to the leg straps, this method allows the support and straps to be used for dressing and supporting the thigh in a very practical, adjustable manner. In this model the straps are also made from one or two layers of LYCRA (™) and the support means, SUP, is made from non-stretchable, clear vinyl or a laminated body with an outer surface made from a layer of loop attachment means, ATM1. It may also be made from any other materials such as fabrics or any other proper manmade materials, however, in such cases they need to have their own attachment means to attach to the support unit.

Importantly, the thickness of the straps may vary in this unit and every other unit to fulfill the need, thinner straps will hold dressing in place while the thicker straps will allow more tension build up and pressure in the tissues.

The support may have openings to allow sweat and air to pass through and also allows gauze pad or a long, removeable layer of lining shown at, LIN, in FIG. 6A or pad to be placed under it to prevent irritation, place pressure, and allow application of medication, etc. This unit may allow electrical leads to be held in place as well, in order to allow a programmed stimulation of the thigh muscles and tissues for various reasons such as prevention of muscle weakness or prevention of phlebitis.

The advantage of this unit is that it allows compression of the whole thigh with the option to adjust the pressure in every special segment of the thigh. Also the unit can be removed and placed with ease.

When a lining is used it may be attached to the support, SUP of the unit on a detachable, re-attachable basis. This allows the lining to be washed and used or exchanged when needed.

Please note that these straps are not attached to each other and are separate.

Importantly, the straps of may be attached to the support unit independently, by having their both ends attached to each side of the support on a detachable, re-attachable basis.

Importantly, the straps may be made from a single layer of LYCRA (™) to allow a uniform cover of the area although their end pieces or the attachment means and the area adjacent to it will be separated to allow easy placement. An example of this model is shown for the leg and will not be repeated to avoid a lengthy application.

Method of use.
1. The user places the support, SUP, on the side of the hip so that the cut, CUT, will be at the hip joint.
2. The user will wrap the belt, BELT, around the waist and attach its free end to the outer surface of the support, SUP, and then attaches the free end of the belt to the outer surface of its own. This is possible due to the presence of the attachment means at the end of the belt and the fact that the belt has a body made from a layer of loop-fastener, attachment means, in its own inner and outer surfaces.
3. The user will wrap the stretchable straps, STR-1, STR-2 and STR-3, around the thigh and attach their free end to the hook fastener attachment means of the support marked at H-ATM2, and will continue to attach the free ends of the straps to the outer surface of their own if the strap was longer. Other means of such an attachment may be used as explained in the text.
4. Further adjustments allows the unit to be in its proper condition.

FIG. 35A, shows schematically, a pad means for use with the hip support unit which consist of three pieces, PAD-A, PAD-B and PAD-C, which are loosely attached by use of an attachment means and can be separated when desired. This unit will be placed under the hip support when the patient is in supine position and when the patient wishes to sit then the middle pad, Pad-B, will be removed to allow the user to bend the hip and sit on the chair or similar places such as the bed pan.

FIG. 36 shows the general view of a support unit that is similar to the unit shown at FIG. 35, except that it is modified for use in the groin area to hold a pad over the wound area in the inguinal region. A sample of such a pad is shown at, PAD, which has a trapezoid-shape and can be used after cases such as a hernia surgery in this region. This unit has a support, SUP, that extends and moves down to cover the inguinal area. The body of this support is made from a type II support which is a non-stretchable layer, such as a laminated body, with an outer surface made from a layer of loop fastener attachment means, ATM1, an inner soft lining for contact skin with a thin layer of foam in between. It may also be made from any other manmade materials. The support, SUP, will be held in place securely by a non-stretchable strap, NS-STR, that is attached to the support, SUP, on one side in a permanent, or detachable, re-attachable basis, and allows the other end of the strap to wrap around the waist and function as a belt. The belt strap will hold the support, SUP, in a stable position. Please note that due to the extra length of the strap, NS-STR it is schematically shown with a cut in its length. A second, but stretchable, strap, S-STR, is attached to the body of the NS-STR, on a detachable, re-attachable basis, in the posterior part of the NS-STR. This method allows the stretchable strap, S-STR, to move down the buttock area of and pass the inner side of the groin, moving up and attaching to the horizontal hook-fastener, attachment means of the support marked at H-ATM2. This combination makes a secure unit for holding the support unit and compresses the pad, PAD, on the wound area in the groin.

Importantly, when the stretchable strap, S-STR, is made from LYCRA (™) it will:
1. Expand in the back to function as a comfortable layer of fabric
2. Shrink and roll in the groin area to limit its presence and the pressure to the sides of the groin.
3. Expand like a wing and cover a wider area in the inguinal area, to hold the support means, SUP, in a stable condition. This combination will make a fine unit for this use.

Importantly, the stretchable strap, S-STR, attaches to the body of the NS-STR on a detachable, re-attachable basis so that the position and location of such an attachment can be changed as needed.

Importantly, the straps may be attached to the support unit independently, by having both their ends attached to each side of the support on a detachable, re-attachable basis.

Method of use.
1. The user will place the combination of the pad, PAD and support, SUP on the inguinal wound site.
2. The user will wrap the non-stretchable strap, NS-STR around the waist and attach its free end to the outer surface of the support, SUP, due to the presence of the attachment means.
3. The user will move the stretchable, strap, S-STR, down from the buttock area and pass it from the inner side of the groin, moving it up and attaching it to the horizontal hook fastener attachment means of the support marked at H-ATM2.
4. Further adjustments allows the unit to be in its proper condition.

FIG. 37 shows schematically the side view of a special foot pedal, designed for use by patients with peripheral vascular disease. This will allow them to pedal for improvement. The use of this unit not only will improve the circulation in the feet and the legs due to the exercise and exercise related vasodilation, but also will improve the movement of the extra fluid in the legs if it exist. This unit consists of.
a. Pole, POLE which stands on a base, BASE and functions to hold the axle, AXEL of the pedals. This pole will be made from combinations of poles to allow the length of this piece to be adjusted.
b. A base, BASE that allows the pole to be placed on the bottom of a bed spring or similar area. This will be fixed on the bed by various methods and means, such as clamps etc. In this prototype, it is designed to sit on the top of the base board of the hospital beds.
c. The unit has an axle, AXEL that goes from one pedal to the another and allows pedals to function similar to the pedals of a bicycle.
d. Specially, designed, cushioned and protected foot pedals, PED-1, PED-2 which are made to allow the foot of the user to be placed on them and prevent from the compromised tissues of the feet and leg from being damaged. These pedals have a horizontal, lower wall which the heel of the foot will be seated on and also have a vertical, flat wall that allows the sole of the foot to push. The pedals also have side walls designed to prevent each foot from moving to the sides, thus they will prevent the feet from being injured.

These pedals allow the feet to be placed inside and to be kept in place by use of bands which will stand in front of the ankles, and keep the foot on the pedals. This is particularly important if the patient is too weak or has neuro-muscular problems that does not allow them to keep their foot inside the pedals. This design is very important since it will prevent from further trauma to the compromised and vulnerable tissues of the feet and will keep the feet stable to benefit from exercise.
e. The unit also has side walls made from circular well-padded pieces, shown at CIR, in this picture and CIR-R AND CIR-L in FIG. 38. The circular pieces, CIR, are fixed to the free ends of the axle, AXEL from one side and holds the poles, POL1 of the foot pedals, PED-1. This allows the foot pedals to rotate around their poles, and is shown better at FIG. 39. This design is chosen for such a use because it does not have a sharp ends or points for a potential trauma to the feet.
f. An electrical motor, EM schematically shown, allows the circular pieces, CIR-R AND CIR-L and the attached pedals, PED-1 AND PED-2 to rotate automatically due to the power of the electrical motor, EM.

The speed of the rotations will be controlled by control of the function of the electrical motor, EM.

This method allows the feet of weak patients to be moved by the controlled movement of pedals in order to circulate the blood and help the muscles tones. The transfer of the movement from the electrical motor, EM to the axle, AXEL may be done by use of chains or wheels used in bicycles or similar means that are part of the available knowledge.
g. A computerized programmer (is not shown since it will be part of the electrical motor, EM) will allow the timing, frequency of function, the resistance, duration of use and other important factors of such automatic unit to be controlled.
h. A remote controller allows the function of the computer to be adjusted from distance.

FIG. 38 shows schematically the front view of a specially designed feet pedal from the FIG. 37. In this figure the
a. Pole, POLE is shown, with that its function is to hold the axle, AXEL, of the pedals on its top and stands on the base, BASE in its lower end.
b. The base, BASE is shown and holds the pole, POLE and allows the pole to be placed on the bottom of a bed spring or similar place.
c. The Axle, AXEL, moves horizontally, from the CIR-R to CIR-L and goes through the pole, POLE in order to allow the circular pieces to rotate around the axle, AXEL.
d. The foot pedals, PED-1, PED-2 are schematically shown.
f. The electrical motor, EM, is shown schematically.
g. A computerized programmer is part of the electrical motor, EM.
h. A remote controller, similar to the unit shown at, RC at FIG. 34, not shown in this picture allows the function of the electrical motor, EM, to be adjusted from distance.

FIG. 39 shows schematically one cushioned, well padded foot pedal such as PED-1 that has side walls designed to allow the foot of the user to be placed inside it and prevent from tissue damage. This unit has a padded walls that allows the foot to be seated for a comfortable safe usage and to push the pedal. The side walls prevent from the feet to move to the sides. The strap, STR, goes from one wall and attaches to the outer surface of the other wall and keeps the foot in place, if the patient is too weak or have neuro-muscular problems that can not keep the foot in the pedals. The pole, POL1, attaches to the circular flat piece, CIR-R and allows the pedal to rotate around it. The inner surface, IS of this pedal is cushioned and the outer surface, OS is shown, and can be made from a rather rigid plastic or a protective fabric.

DETAILED EXPLANATION OF THE INVENTION

This invention is related to the problems associated with wound dressing, supports and wound care on humans and animals. It also addresses the issues of wound dressings, enhancing the process of healing and dressing a wound using one hand. Commonly gauze pad/s or wound dressings are used and are held in place by use of adhesive tapes or a bandage. However, the use of adhesives has multiple problems as listed:
1. It is difficult to do with elastic gloves since the adhesive tapes stick to the gloves and creates problems.
2. The adhesive tapes cause skin irritations and create discomfort on removal. Importantly, they do not adhere to the skin in the areas that are covered with hair. Many times the hair has to be shaved which is a process of its own.
3. Some wounds need frequent inspections or need to be changed. The removal and adhering of adhesive tapes over and over, increases their problems.
4. Many wounds in the limbs and body need wrapping which can not be done by use of adhesive tapes effectively and conveniently.
5. The issue of dressing with one hand is a very important issue and this will be helped by use of these units.
6. The dressing of the ulcers in the toes and heels are difficult and time consuming and a better unit will be useful.
7. Compression of the some wounds are important to decrease tissue swelling and related ulcers; these models will help in this regard.
7. Also, dressing a wound as quickly as possible is a vital issue and may make a big difference in daily life and in man-made or natural disasters. Therefore, the methods and means used in this application are aimed to reduce the time needed for wound dressing to the least possible.

This application introduces methods and means of dressings that not only will simplify the process, but will decrease the use of adhesives and makes this process easier. These goals are achieved by the following methods and means:
1. The use of support units and wound dressing as shown in FIGS. 1 and 2 and a series of wrapping methods that use little adhesives and are held in place with use of straps and bands. The use of supports simplifies the application of wound dressing significantly. And importantly, the applicant has introduced the use of straps and wrapping means shown at FIGS. 1-6 in which the body of these straps, STR, are made from a special material. This applicant believes he is the first to introduce the use of this particular unit for this purpose.

The body of these straps, STR, is made from a woven fabric, comprising of elastic threads providing stretchability of the fabric. The fabric also has a woven construction that provides the VELCRO (™) hook material to separably hook onto the woven fabric. The applicant has used the combinations of the fabric, LYCRA (™), which functions quite well for this purpose. The applicant considers this combination to be a very useful tool for making these units and many other similar units. Therefore, he reserves his right to ask for a patent for this combination alone for use in construction of different materials for various uses.

This material has the following favorable properties and characteristics:
a. It has an elastic body which pulls the attached units, such as support units, and keeps them in place with reasonable tension. This mild, comfortable, non-strangulating, and uniform tension is an important property for the use of this material in many of the wound dressings since it functions well with the skin. Importantly, it stretches when the underlying part of the body such as a joint moves.
b. The strap stretches, conforms and accepts the shape of the area, which is also very important since it makes this unit to be properly used in many areas of the body and stays on curved areas, such as the legs, arms etc., easily and comfortably.
c. Very importantly, it functions as an attachment means for the attachment of the hook fastener attachment means, VELCRO (™). This makes a very unique property and allows the hook attachment means to attach to this strap on a detachable, re-attachable basis in any desired area, which is very convenient and important.
d. The above mentioned properties of this unit allows the effective length of this strap to be chosen and adjusted easily.
e. The material is soft and comfortable and does not irritate the skin.
f. The material is thin and allows it to be used without much difficulty.
g. The material is a thin fabric which allows heat and sweat to dissipate.
h. Structurally, this fabric is a thin woven fabric that allows it to be stretched in one direction more than the other, and has one face that is shiny and has properties that the hook fastening properties will engage with it on a detachable basis.

It is reasonable to believe that the construction of this fabric to be modified to make new kinds with following properties.
1. To have loop fastener attachment means properties on both its front and rear surfaces.
2. To have different thicknesses and still function as the loop fastener attachment means. This is to allow a different degree of tension to be provided.
3. To alter the elasticity of these fabric in order to produce fabrics with different degree of tension in their body for different uses.
4. The applicant believes that modification of this fabric is possible to make a unit that its attachment function to a hook fastener will be enhanced and improved.
5. To stretch in both directions.

The applicant has previously discussed the properties of this fabric with his patent lawyer but still has not be able to define this material in any other way. Although, he claims that these units will be made with other fabrics that have similar properties.

This material which is commercially available with name of "Lycra" (™) is a woven fabric, made from a polymer that has a rather shiny surface on one side that functions as the loop fastener attachment means. The other side is not as shiny and has a weaker loop fastener attachment means.

Importantly, the applicant has sewn, or attached, two layers of this fabric to make a thicker fabric that provides more elastic power with double the sides-loop-fastening attachment means function.

The applicant introduces these straps as one important part of this application. Furthermore, more modifications of these straps can be made as follows:

The body of these straps may be modified by adding bands of stretchable, non-stretchable or shaped pieces such as a layer of latex material, vinyl, a polymer, latex paints, elastic or rubber means or similar materials to them. These parts may be embedded inside their body during the manufacturing process or they may be applied, attached, adhered or fixed onto them at a later time. These bands function to prevent the thin body of these straps from changing, curling, etc. The elastic means will allow this unit to expand and retract as well. Importantly, this interaction allows the development of a particular shape for a special use, such as that of the elbows, knees, heels, etc. This construction, when stretchable, allows the unit to conform to accept the shape of the part of the body.

The straps may have different shapes or sizes, the reason for which being to provide a special configuration or body to some parts of these straps.

Importantly, an elastic strap with an adjustable end piece such as a buckle system may be used with these support units as well. The use of such units allows the effective length of the elastic strap to be modified. It is very important however, to note that the use of buckles and similar units that can modified the effective length of any elastic fabric is still different from the use of these straps due to its special property. The applicant also has noticed that attaching this fabric to the surface of a sponge layer makes it stronger.

Some models of such modifications are shown at, FIGS. 8 and 9, by adding bands of stretchable or non-stretchable shaped pieces such as a latex, vinyl, different polymers, elastic or rubber means to the body of the strap. An interaction that allows development of a particular shape for a special use is shown at FIG. 9. Use of a buckle means is shown in FIGS. 16-17A which allows the length of the straps to be adjusted, etc.

Importantly, the method of handling the extra strap or free end of the strap can be varied such as:
1. The use of adhesives that allow the end of the strap to be attached to the rear of its own or the support on any particular location. The applicant has used adhesives tapes that allow the adhesion of the end of the strap to its own rear surface to occur on a detachable, re-attachable basis and more than few times.
2. The use of other attachment means that allow the end of the strap to be attached to the rear of its own. The applicant has used hook-loop fastener attachment means for this purpose. The free end of the strap has a hook fastener which allows the free end of the strap, STR, to attach to the rear surface of the strap, STR in any location and on a detachable, re-attachable basis. This occurs when the outer surface of the strap has the same property to function as the loop-fastener attachment means.
3. Snaps may also be used as attachment means that allow the end of the straps to be attached to the rear surface of its own in any optional location. Snaps with small spores will function in this capacity. The snaps can be made from a flat piece of metal or plastic with a small hook that will attach to the outer surface of the strap. This can be removed and attached again.
4. The applicant believes that other attachment means can also be made to allow the free end of the straps to be attached to the body or the surface of the straps or its free end. This attachment by design will be on a detachable re-attachable basis. This is to allow the free end of the strap to be attached to the rear surface of its own in any optional location. Mechanical means, buckle means or similar units may be also made to allow that piece to be attached to:
   a. the body of the strap, STR.
   b. to the free end of the strap STR, or both to allow this piece or means to be attached during initial use and allow the future attachments of the free end to the body of the strap to be done on a detachable, re-attachable basis.
5. This application shows means of modifying the end of the strap in order to allow it to attach to the surface of the support or the rear surface of its own. Such methods are shown in FIGS. 1E, 1F, 18, 18A, 18B, 18C and 18D.
6. The use of D. Ring is shown at FIGS. 10 and 26.
7. A buckle means is shown at FIGS. 16-17A.
8. Also please note the applicant has shown models which allow the end of the strap to be modified on the site where it attaches to the support as shown at FIGS. 1C and 1D.

Further modifications of these methods may be done to find different means to fit this use.

The supports and their functions.

The supports are mainly made from non-stretchable materials, such as:
1. Clear PVCs that allow the underlying area such as wound site to be seen for bleeding, etc.
2. Use of a laminated material that is available and is a non-stretchable, material made with a layer fabric in its outer surface that functions as the loop fastener attachment means, ATM1, and an inner part which is a layer of soft lining for placement on skin, with a layer of foam sandwiched between them.
3. The support may be made from screens, different fabrics, or other man-made materials.
4. Particular supports may be made by modifying the elastic fabrics by adding bands of stretchable, non-stretchable or shaped pieces such as a layer of latex material, vinyl, a polymer, latex paints, elastic or rubber means, or other similar materials. One model of such modifications is shown at FIG. 8, which shows the front view of a special, stretchable support unit made from shaping the same material used for the strap, STR or lycra (™). Here the Lycra is modified with use of bands made from materials such as latex as shown at L-BAND. The shaping of this stretchable material by this method or the use of sewing techniques creates an elastic, shaped support. Such a support is useful in areas with a particular shape and function, such as the knees, ankles, elbows, toes, etc. This shaped, stretchable support, SUP, allows better handling and placement of these units.
5. In some cases the supports are made from stretchable materials or the stretchable part of the strap stands on the wound.

The function of the supports are very important in these units as following:
1. They stand on the wound site and keep the dressing in place.
2. In some cases they function as a vital piece that allows the straps to be handled easily, may be used to hold the unit together and prevent it from moving. Although the placement of the first strap may not be perfect, in practice it allows the second and third straps to be placed more precisely. Then, the user can return and re-position the first strap and other straps to achieve the best result. This function will otherwise not be possible particularly, by one operator, thus such function of the supports is extremely important and vital.
3. In many units the other vital roles of the supports is its function as the stabilizer, to make the units stable and prevent the straps from moving. For example, in areas such as the leg and forearm, the limb has a wider body in proximal area, which varies in its shape and decreases gradually. These are areas that move, as well, and cause wrapped material to slide to the thinner distal area such as the ankle and wrist. This can be easily-controlled with use of a strap that matches the length of these limbs and uses multiple straps as shown in FIGS. 6, 7A, 33 and 35.

Please note that support may be made to be simple, narrow, to bend to rotate and from different materials and to have different shapes. It can be a very simple support with a narrow body but still to allow the strap to attach and function. It can be made to be complicated with having various forms and attachment means.

4. The use of supports with multiple straps allows the tension of the straps in one segment to be adjusted while the other straps stay stable in their place. This function is also very important in areas such as the legs, where adjustment of the tension in one segment may be needed.

5. Importantly, combinations of multiple supports and straps as specified in this application allow parts of the body that are commonly very difficult to be wound dressed or supported to be handled with ease. Examples of these models are shown for the head and chin in FIGS. 19-21, for the shoulder in FIGS. 22-23, for the elbow in FIG. 25, for the hip in FIGS. 26-26B, and for the arm/hands in FIG. 35.

6. In some other cases the support may function as a protective means that shields the wound from coming into contact with unwanted objects. An example of such a unit is shown in FIGS. 26C-D. These figures show schematically a protective support unit for the chest, in which a rather rigid support is held away from the wound site by use of walls made from foams and is kept in place with use of straps. This particular unit is designed to keep the clothing away from the wound after open-heart surgeries. Importantly, it can be modified to be used in any other wounds that need such a protection such as the head, neck, body or limbs. It is important to note that the use of multiple straps in different directions allows such a unit to be held in place with ease, which would otherwise be impossible.

By use of these basic ideas, methods and means, the applicant has designed multiple units that are useful in solving the problem with wound dressing, compression and supports for various areas of the body. In the following parts he specifies how the basic units are modified for use in different areas.

FIGS. 1 and 2 show the front/top view of a wound dressing unit which consists of a clear front support, SUP, which has a strap, STR, attached to it on the left side of the support. The support, SUP, has zones of attachment means, ATM2, made from hook type of hook-loop-fastener (VELCRO™). These zones are further specified by ATM2-A, ATM2-B and ATM2-S. These hook-fastener patches allow complementary pieces such as the body of the strap, STR, which function as a loop-fastener, attachment means. This property allows the strap, STR, to attach to the zones of the hook-fastener attachment means shown at ATM2-A, ATM2-B and ATM2-S, or any similar zones, on a detachable, re-attachable basis. Specifically the applicant has found during his experiments that when the strap is made from special material such as (LYCRA-™), it allows the strap to attach to the hook type attachment means, categorically shown at ATM2, on a detachable, re-attachable basis. The free end of the strap, STR, also has a band made of hook-fastener attachment means ATM2 (this may be double-sided) that allows it to be attached to the rear surface of the body of the strap, STR, on a detachable, re-attachable basis. The zones of the attachment means, ATM2-A and ATM2-B, allow complementary bands, BAND-A and BAND-B, made from LYCRA, (™) to be attached to them on a detachable, re-attachable basis. These bands are designed to attach to the attachment patches, ATM2-A, ATM2-B and ATM2-S of the support, SUP, on a detachable, re-attachable basis.

Importantly, instead of the zones of the attachment means (ATM2-A) and (ATM2-B) the unit may have a second, long zone of the hook-fastener attachment means such as the zone ATM2-S on the left border of the support, SUP, as shown in FIGS. 1A and 1B. This method allow the attachment of the strap, STR, or the bands BAND-A, BAND-B to support. The free end of the strap, STR, shown in the left side of this figure has a piece of adhesive tape, ADT, (the actual size is bigger) which allows it to be attached to the rear surface of the strap, STR, after making a U-turn, and keep the end piece stable. The adhesive tape has folded protective cover (PC). This part is shown in detail in FIG. 2. Instead of the adhesive tape, ADT, this part may be made from any other materials or means that will allow the end of the strap, STR, to be attached to the surface of the strap, STR, or the support, SUP, on a detachable, re-attachable basis. The protective cover of the adhesive tape allows it to be removed without touching the gloves.

Importantly, the line of attachment of the strap, STR, to the support, SUP, may be made optional by having a matching layer of adhesive attached to the border of the support, SUP, and protected by a protective layer, PC, as shown at FIGS. 1C and 1D. This allows the end of the strap, STR, to be attached to the zone of the adhesive layer on an optional basis. The user will then choose the length of the strap and cut the extra end and attach the end of the strap to the outer surface of the support, SUP. This method allows the length of the strap to be chosen for any given person.

FIG. 2 shows the side view of a wound dressing unit shown at FIG. 1. This figure shows the cross-cut side view of the support, SUP, and the strap, STR, attached to it on left side. The support, SUP, has zones of the attachment means: ATM2, on its upper surface which is made from hook type of hook-loop-fastener (VELCRO™). ). In this view the ATM2-B and ATM2-S are shown. These zones allow complementary pieces such as the body of the strap and Band-B to be attached to them on a detachable, re-attachable basis. BAND-B is attached to the right side of the support in this view and has a body made from the same material as the strap, STR.

The piece of gauze pad, GP, is attached to the lower surface of the support, SUP, by a detachable, attachment means, ATM, which can be a layer of adhesive. This allows the pad to be removed and replaced by a similar or another piece. This allows a soiled gauze pad to be exchanged with a fresh one.

Importantly, the zone of the attachment means, ATM, shown in the lower surface of the support, SUP, may be made from a zone of adhesive tape with multiple individually, removeable protective covers as shown at FIG. 1D. This method allows some of these zones such as a zone in the lateral side of the support adjacent to the base of the BAND-B to be used for the attachment of the support, SUP, to the skin, after the removal of its protective cover. The center zone may be used for the attachment of the gauze pad, GP to the support. The free end of the strap, STR, shown on the left side has a patch attachment means: ATM2 made from hook type of hook-loop-fastener (VELCRO™). This patch allows the free end of the strap, STR, to be attached to the outer surface of the body of the strap, STR, on a detachable, re-attachable basis. The cross-cut of the adhesive tape, is shown both on the upper and lower surfaces of the strap, STR. The layer of adhesive, ADH, is shown with a short, dotted-line. It has a protective cover, PC, which is shown on the upper surface by a folded shape and in the lower surface by a straight line. The folded model is easier to be removed without being touched by the gloves. Thus, please note that the adhesive layer can be in either or both upper and lower surfaces of the strap, STR.

The unique importance of this unit is that it allows the subject to dress a wound with use of one hand, which the applicant believes is very important.

Method of use:
1. The user places the support piece, SUP, on the wound and places the strap, STR, under the limb so that by pressing on the strap, STR, it will loosely prevent the support, SUP, from moving.
2. He/she wraps one of the bands, the proximal band, BAND-A (it is optional to choose BAND-A or BAND-B) around the limb in the opposite direction of the strap, STR, and bring its free end to attach to the ATM2-A from the support, SUP, on detachable, re-attachable basis.
3. The user wraps the distal band, Band-B, around the limb on the opposite direction of the strap, STR, to bring its free end and attach it to the ATM2-B on the support on a detachable, re-attachable basis.
4. The user wraps the strap, STR, around the limb for attachment to the ATM2-S on the side of the support, SUP, on a detachable, re-attachable basis. Then he/she can wrap the end of the strap around the outer surface of the strap to make a U-turn and adhere the adhesive tape ADT from the end of the strap to the rear surface of the strap, or by use of a connection means ATM2.

Importantly, in models which the layer of adhesive, ADH, is placed on the lower surface of the strap, STR, (instead of being on the upper surface of the strap as shown), the user will wrap the strap on the support. Then the attachment means, ATM2, or the adhesive layer, ADH, from the free end of the strap, STR, will be attached or adhered to the outer surface of the body of the strap, STR.

Based on the experiments of this applicant, this process takes only about 15-20 seconds of time or less and makes a very stable and easy method of wrapping a wound with the use of one hand only.

Importantly, the unit may consist of only one strap, the strap, STR, with the bands, BAND-A and BAND-B omitted. This unit is functional except that it does not allow the placement by one hand as easier as can be done with the presence of the bands.

Importantly, in some cases the user may need to have the gauze pad, GP, or the support, SUP, adhered to skin. To satisfy this need the front of the gauze pad or its border may have a layer of adhesive to allow such an adherence to be achieved. The adhesive layer will have a protective cover such as PC, which will be removed before use. In some cases, the support may be needed to adhere to the skin in its border or some portion of its body. In such cases, again the lower surface of the support or its border will also have a layer of adhesive to allow the support to be adhered to the skin. The adhesive layer will have a protective cover such as PC, which will be removed before use. This model is shown in more details at FIG. 1D.

Importantly, this system can be modified to be used in any area that can be used such as the head, face, neck, arms, chest, abdomen thigh, legs, ankles etc.

FIG. 1A shows the front view of a wound dressing unit that is similar to the unit shown previously in FIG. 1 except that this unit shows some more beneficial features such as:
1. The support, SUP, has two parallel zones of hook-fastener attachment means, shown at ATM2-A and ATM2-B. The importance of these attachment means is that it allows an easier control of the strap, STR. So that the strap will first attach to the attachment means ATM2A and then to ATM2-B.
2. The adhesive tape at the end of the strap, STR, is shown at ADT-S, consists of two separate pieces or a piece with a cut on it. The importance of this method is that it allows an easy placement of the adhesive tapes since it will be the handling of two smaller adhesive tapes rather then one big one.

Second, the two pieces allow one piece to be in a different area of a wound side. This will make a different curve that will help in some places such as the leg area, with the upper adhesive tape above the large muscle of the leg and the lower adhesive tape on the lower part of the calf. This will prevent the strap from moving.
3. The support, SUP, has an adhesive tape of its own shown at ADT-C which will adhere to the skin of an area such as the thigh to prevent the movement and falling of the support in areas such as the thigh and groin. However, when this adhesive tape is adhered to the skin it will prevent the support from moving.

Importantly, instead of the adhesive tape of its own shown at ADT-C, the lower surface of the support, SUP, may have a zone of adhesive with multiple individually, removeable protective covers, as shown in FIG. 1D. This allows some of these zones such as a zone in the lateral side of the support on the lower surface of ATM2-A to be used for the attachment of the support, SUP, to the skin, after the removal of its protective cover, and other zone to be used for attachment of the gauze pad.
4. The strap, STR, has another adhesive tape shown at ADT-B which will be adhered to the skin of the user on an area such as the thigh to prevent the strap from moving and falling. This piece of adhesive tape will prevent such a move.

Please note that each one of these adhesive tapes will have their own protective layer, which will be removed before use.

FIG. 1B shows the side view of a wound dressing unit shown at FIG. 1A. This figure shows the vertical, cross-cut view of the support, SUP, with two zones of hook-fastener attachment means, shown at ATM2-A and ATM2-B on its upper surface. The adhesive tape of the support, SUP, is shown on its lower surface at, ADT-C. (the arrow is aimed to the cover of the this tape)

The strap, STR, is attached to the support on the left border. Two adhesive tapes of the strap, STR, are shown in this figure. The cross-cut of the adhesive tape, ADT-S, is shown at the left side and the figure shows an adhesive layer, ADL, covered with a piece of protective layer, PC. The cross-cut of the adhesive tape, ADT-B, is shown at the lower, middle part of the strap (the arrow is aimed to the cover of the this tape).

FIG. 1AX is designed to show another method of preventing the support from falling in areas such as the forearm—which due to its anatomical and functional virtue may cause the support to slide down. In this model, a band similar to the BAND-A is attached to the support and will circle around the lower arm and attach to the zone of the hook-fastener, attachment means, ATM2, from the support. This will help prevent the movement of the support. Importantly, this strap may also have a zone of adhesive means of its own to adhere to the skin to prevent it from moving. In this view, the front of the support, SUP, and strap, STR are shown and the BAND-A is attached to the upper border of the support, SUP. BAND-A has its own zone of the loop-fastener, attachment means, ATM1-A, to attach to the zone of the hook-fastener, attachment means, ATM2, from the support.

FIG. 1C shows the front view of a support, SUP, that has a body made from a layer of clear PVC shown at SUP, which has a zone of adhesive in its left border covered with a protective layer, PC. The support, SUP, has two zones of hook-fastener, attachment means, shown at, ATM2, that allow a strap to be attached to them on a detachable, re-attachable basis. Also importantly, the lower surface of this support, SUP, has a zone of adhesive layer, not shown in this figure but in FIG. 1D, with multiple individually, removeable protective covers explained in detail at FIG. 1D.

FIG. 1D shows the vertical cut view/side of the support, SUP, which has two zones of hook-fastener, attachment means, ATM2, on its upper surface. The adhesive layer, ADH, is shown at the upper surface on the left side with a dotted line. The adhesive, ADH, has a protective layer, PC. Also importantly, the lower surface of the support, SUP, has zones of adhesive layer, ADH, shown in a dotted line with multiple individually, removeable protective covers, PC-S1, PC-GP AND PC-S2 which allow the following options:

a. The adhesive layer, ADH, under the protective covers, PC-S1 AND PC-S2 allows the support, SUP, to be adhered to the skin for preventing movement and falling of the support from the wound site.

b. The adhesive layer, ADH, under the protective covers, PC-GP allows the gauze pad, GP, to be adhered to the body of the support.

Method of use.

1. The user measures the circumference of the limb to decide about the length of the strap, STR, and cuts the strap in a proper length.
2. The user removes the protective layer from the layer of adhesive, ADH, on the upper surface of the support, SUP.
3. The user attaches the free end of the strap to the layer of adhesive, ADH. This will make a unit that has a strap with a proper length and can be used to dress the wound site.
4. The user removes the protective cover, PC-GP to adhere a gauze to the body of the support.
5. The user removes the protective covers, PC-S1 AND PC-S2, from the lower surface of the support, SUP, and adheres the support, SUP, to the wound side. This prevents the support, from moving.
6. Then he/she will be able to attach the strap and use the unit as explained earlier.

FIG. 1E shows the side view of a method that allows the end of the strap to be attached to the outer surface of the support or the strap STR, itself and also allows the strap to be detached and re-attached afterward. In this method, the lower surface of the strap, STR, has a zone of hook-fastener, attachment means, ATM2, which is adjacent/attached to a longer zone of loop-fastener, attachment means, shown at ATM1. The lower surface of the loop-fastener, attachment means, ATM1, has a layer of adhesive, ADH, that has a cover of its own, PC. The attachment of the hook-fastener, attachment means to the loop-fastener, attachment means is on a detachable, re-attachable basis. This method allows the user to attach the loop-fastener, attachment means, ATM1, located at the lower surface of this combination to the outer surface of the support or the strap on a desired place by removing the protective cover, PC. This will adhere the loop-fastener, attachment means, ATM1, on the outer surface of the support or the strap on a permanent basis. The user can then detach the zone of hook-fastener, attachment means, ATM2, from the loop-fastener, attachment means, ATM1, and re-attach it to a detachable, re-attachable basis. Thus, the end of the strap will be attached to the support or its own surface on any desired area.

FIG. 1F shows the side view of a unit similar to the unit shown in the previous FIG. 1E except that this model allows the end of the strap to be placed in any desired area of the support or the strap. In this model, the rear surface of the hook-fastener, attachment means, ATM2, has its own layer of adhesive layer, ADL, that is protected by a cover, PC. The rest of the body of this unit is similar to the unit shown in the previous FIG. 1E. This allows the user to remove the protective cover, PC, from the lower surface of the loop-fastener, attachment means, ATM1, and adhere the combination to the outer surface of the support or the strap. Then the user will wrap the strap, STR, over the support, SUP, shown at FIGS. 3-4 and adhere the end of the strap, STR, to the outer surface of the hook-fastener, attachment means by removing the protective cover, PC. This will fix the hook-fastener attachment means, ATM2, the lower surface of the strap, STR, and loop-fastener, attachment means, ATM1, on the outer surface of the strap, STR, on a permanent basis. The user can then detach the zone of hook-fastener, attachment means, ATM2, from the loop-fastener, attachment means, ATM1, and re-attach it on a detachable, re-attachable basis. Thus, any part of the strap, STR, can be attached to the support or the strap in any desired area.

FIG. 3 shows the front view of a wound dressing unit that is similar to the unit shown in FIG. 1, except this unit utilizes special pieces (previously introduced by this applicant and referred to as YD pieces), shown better at FIG. 4. YD pieces are made from a piece of medical adhesive tape with a having zone of loop-fastener attachment means as shown at ATM1 on its lower surface where the adhesive material is located, as shown at FIG. 4. It allows the end of the YD piece to attach to the zone of ATM2-S from the support unit. The rear surface of this zone, ATM-1 on the YD piece has a zone of hook-fastener, ATM2, of its own that allows a complementary piece, such as strap, to attach to it on a detachable, re-attachable basis.

The external end of the YD piece has a layer of adhesive, ADH, covered with a folded protective layer, PC, that allows it to adhere the adhesive part onto the skin. This allows the user to apply this unit with one hand and exchange the wound dressing without the need for another adhesive part each time, since the piece, YD, can be detached from the support on a detachable, re-attachable basis.

FIG. 4 shows the vertical cross cut view of a wound dressing unit shown at FIG. 3. This figure shows the vertical-cut view of the support, SUP, and the strap, STR, as shown in FIG. 3. The support, SUP, has patches of the attachment means which, in general, are shown at, ATM2, on its upper surface. These are further specified by the zones such as ATM2-B, ATM2-S, etc. In this figure only the ATM2-S is shown, but the attachment means ATM2-B is not shown, since the cross-cut was in the middle of the unit. On the right side of this figure the piece YD is shown. The left lower surface of the piece YD has a zone of loop-fastener attachment means, ATM-1 that allows it to be attached to the zone of ATM2-S from the support, SUP, on a detachable, re-attachable basis. The piece YD, has a layer of adhesive, shown at ADH, on a dotted-line, that allows this part to adhere to the skin and hold the end of the support, SUP, securely on the skin. The layer of adhesive has a folded protected cover (PC) that will be peeled off before use. Importantly, the folded protective cover PC allows it to be held and pulled off easily from the adhesive layer to expose the adhesive layer. This allows users with latex gloves to use these units easily, without touching the adhesive layer that sticks to the latex gloves. The piece YD, has a patch of the attachment means: ATM2 on its upper surface, made from hook type of hook-loop-fastener (VELCRO™). This patch allows a complementary piece such as the body of the strap, STR, or other units with loop-fastener properties to be attached to it on a detachable, re-attachable basis.

The gauze pad, GP, is attached to the lower surface of the support, SUP, by attachment means ATM.

The free end of the strap, STR, shown on the left side has a zone of attachment means: ATM2 made from hook type of hook-loop-fastener (VELCRO™). This patch allows the free end of the strap, STR, to be attached to the outer surface of the body of the strap, STR on a detachable, re-attachable basis. Please note that such an attachment can be achieved when the outer surface of the strap, STR, is able to attach to the hook-fastener, attachment means. This is possible either by altering the manufacturing process of the strap or making a double sided strap by sewing the fabric with the loop-fastening, attachment means property outside. The cross-cut of the adhesive tape, ADT, is shown both on the upper and lower surfaces of the strap, STR, by marking the layer of adhesive, ADH, with a short, dotted-line. This layer is pointed out at the upper surface but not in the lower surface to avoid a crowded figure. The adhesive, ADH, has a protective cover, PC, which is shown on the upper surface by a folded shape and in the lower surface by a straight line. The folded model is easier to be removed without being touched by the gloves. Thus, please note that the adhesive layer can be in either or both upper and lower surfaces of the strap, STR.

FIG. 5 shows the front view of a support unit, SUP, which has a non-stretchable body (may in some cases be stretchable) and openings, OP, that allow air and gasses to pass through. It has the zones of the attachment means, ATM2 made from hook-fastener, attachment means, and which are farther specified by ATM2-A, ATM2-B and ATM2-S. Importantly, many of the supports used for the units in this application use a laminated material with an outer surface made from a loop-fastener attachment means, ATM1, an inner surface made of a soft lining that stands on the skin and a thin layer of foam in between. The use of this material with having zones of hook-fastener attachment means, ATM2, on its outer surface gives the option of attaching straps with both loop-fastener body and hook-fastener zones and end pieces. Also importantly, the double-sided, hook-fastener pieces such as the one shown at FIGS. 18 and 18A may be used with these units with or without adhesive zones. Importantly, a piece made of double-sided, ATM2, will allow a strap and support that have a body with loop-fastener to be attached to each other on a detachable, re-attachable basis.

Importantly, instead of the zones of the attachment means, ATM2-A and ATM2-B, the unit may have a second long zone of the hook-fastener attachment means, such as the zone ATM2-S, on the left border of the support. This allows the attachment of the strap, STR or the bands BAND-A and BAND-B to the support.

FIG. 5A shows the front view of a support unit which is similar to the model shown at FIG. 5, except the support is made from a body with an outer surface made from a layer of loop-fastener attachment means, ATM1. This support, SUP, has a second support piece, referred to as Support A, SUP-A, that is attached to the outer body of the first support, SUP, along the Attachment Line, AL. The free end of the support A, SUP-A has a zone of hook-fastener attachment means, L-ATM2, that allows the Support A, SUP-A, to attach to the outer surface of the first support, SUP, on a detachable, re-attachable basis. The advantage of the second support, SUP-A, is that it allows tubings, wires, suction bulbs, etc., to be kept between these two layers securely. The outer surface of the second support, SUP-A, has a pocket, POC, of its own that allows a suction bulb to be placed inside it as well, if needed.

This unit will have a strap, attached to one side of support, SUP, and the free end of the strap will attach to the attachment means, ATM2, of this support as explained previously. These units may be placed in the arm, around the limb, chest, abdomen, etc.

FIG. 6 shows the general view of a support unit similar to the unit shown at FIG. 1, except this unit is modified for use on the leg and to support them as well. This unit allows secure and easy dressing of the leg without the need for adhesive tapes. In this model the support, SUP, has a long, rather rectangular shape and covers the front of the leg, or the wound site. The support, SUP, is shown in more detail at FIG. 6A. It has a long zone of hook-fastener, attachment means on its right border that allows loop-fastener attachment means, ATM1 to be attached to it on a detachable, re-attachable basis. The left border of the support unit, SUP, is attached to three straps: STR1, STR2 and STR3, on a permanent basis although importantly, they may be attached to the support on a detachable, re-attachable basis. These straps are sized to wrap around the leg on its upper, middle and lower part. The straps will wrap around the leg and their free ends, will be attached to the support, SUP, by use of the loop-fastener attachment means, at their ends shown at ATM1-1, ATM1-2 AND ATM1-3 which are respectively attached to the end of the straps STR1, STR2 AND STR3. This method allows the dressing/supporting of the legs and thighs in a very practical, adjustable fashion. In this model the straps are also made from one or two layers of (LYCRA™) and the support means are made from vinyl, although they may be also made from any other materials such as fabrics or any other proper man-made materials. The support may have openings in it to allow sweat and air to pass through. The support also allows a gauze pad or a long, removeable layer of lining, shown at LIN, in FIG. 6A, or a pad, to be placed under it. The lining or the pad prevents irritation, and also allows application of pressure and/or medication.

Importantly, this unit allows electrical leads/pads to be held in place for a programmed stimulation of the leg muscles and tissues. This will be done for various reasons such as prevention of muscle weakness or of phlebitis.

Importantly, the value of these units is that allows the pressure in different segments of the leg to be adjusted independently. Also the unit can be removed and applied easily, it is easy to learn how to use and can be placed over the stockings and pants.

This model can be used with extension to the thigh area as shown in this applicant's previous applications and also is shown at FIG. 35.

Importantly, the straps of this unit may be attached to the body of the support unit independently, by having one end of the straps be attached to one border of the support and the other end attached to the other border of the support both on a detachable, re-attachable basis. This was shown by the applicant in his previous models and applications to USPTO.

FIG. 6A shows only the general view of the support piece shown at FIG. 6. In this figure the body of the support is shown at SUP, and it has openings, OP, a long zone of hook-fastener attachment means, ATM2, which is shown in its right border. A layer of lining, LIN, is attached to the rear surface of the support, SUP, and extends from its borders. The lining, LIN, is attached to the body of the support on detachable, re-attachable basis to allow the exchange.

FIG. 6B shows schematically a support unit similar to the unit shown at FIG. 6 placed on a leg. This unit has three straps which each have straps with their own attachment means at each ends and that are attached to the support, SUP, on a detachable re-attachable basis. The support of this unit has one long zone of hook-fastener attachment means, ATM2, in the right and left border of its body. This model allows the effective length of the straps to be adjusted from both ends of the straps. The three straps are further marked as STR1, STR2 AND STR3, and are attached to the support unit by use of the loop-fastener attachment means, ATM1, which are part of the free ends of the straps. When the straps have the loop-fastener attachment property of their own, they will attach to the support themselves. These straps are properly-sized to wrap around the leg on its upper, middle and lower part. They can be attached to the support, SUP, by use of the pieces of loop-fastener attachment means at their ends shown at ATM1-

1, ATM1-2 AND ATM1-3 which are respectively attached to the one end of the straps STR1, STR2 AND STR3. The other ends of the straps have similar attachment pieces as well, which are not marked in this figure to prevent a crowded picture. In this model the straps are also can be made from one or two layers of (LYCRA, ™) and the support means is made from clear non-stretchable vinyl, although it may also be made from any other materials such as fabric or any other man-made material.

FIG. 6C shows schematically the general view of a support unit similar to the unit shown at FIG. 6, except in this unit the body of the strap is made from a non-segmented fabric, marked, CSTR. This fabric is attached to the body of the support along one of its borders and continues to wrap around the leg, but ends with three separate loop-fastener attachment means, ATM1-1, ATM1-2 AND ATM1-3. The end pieces allow the end units to attach to the hook-fastener attachment means, ATM2 from the support, SUP, on a detachable, re-attachable basis. Importantly, the value of this model is that the continuous body of the strap does not leave an open area or a line of compression on the legs. Importantly, this unit is also chosen to show that a strap may have a single body with more than one ending.

FIG. 7 shows the front and side views of a support unit similar to the unit shown at FIG. 5, which is modified by adding a U-shape extension to it. This unit is designed to support the middle and lower ankle area in both sides of the ankle, inside and out, and allows the compression of those areas. In this model a support piece similar to the support, SUP, shown at FIG. 5 or an extension of the support of the leg support is utilized and shown as the inner support, I-SUP, and functions to compress the inner part of the ankle. This support, I-SUP, moves down and covers the inner ankle and connects to a piece of an elastic strap shown at U-STR. The U-strap makes a U-turn under the foot and attaches to another non-stretchable support that functions as the outer support, O-SUP. This compresses and supports the outer ankle area and has a narrow band, C-BAND, which is an elastic strap that wraps around the lower leg or ankle area and holds the O-SUP in place. The C-BAND allows a wider strap, such as STR3, shown at FIG. 6B to wrap around the I-SUP AND O-SUP keep these supports in place, squeezing the tissue in between them. The importance of this unit is:

A. The U-shaped support means supports the middle, lower and lateral part of the ankle and allows the compression of the tissues in these areas. The importance of this unit is that it allows dressing and compression of the tissue and vessels on the lower inner ankle-foot area to occur for a better result and in a measurable and adjustable manner with placement of an inflatable balloon connected to a gauge. The use of this unit is in vascular problems, particularly in venous insufficiencies of the legs, where compression of vessels for decreasing the hydrostatic pressure and the prevention of the extravasation of fluid in this area is needed. Please note that in order to prevent confusion, the upper parts of the unit are not shown in this figure.

Importantly, in some cases there is a need for further compression of the lower leg to raise the amount of pressure on the tissue. In such cases the inner support, I-SUP and the outer support, O-SUP, are made from rather rigid pieces such as a shaped polymer or metal that are connected to each other in the lower side by a strap. The position of this strap on the supports is adjustable and allows the distance of these two inner support, I-SUP, and the outer support, O-SUP, to be adjusted. Importantly, the outer surfaces of the inner support, I-SUP, and the outer support, O-SUP, have attachment means, such as hook-fastener attachment means, ATM2. This allows a wider, horizontal strap or two straps similar to one shown at C-BAND to wrap around the lower leg and hold the I-SUP and the O-SUP in place to further compress the tissues in this area. This combination can be used as a separate unit, or in combination with the leg support. Importantly, the rigid supports can be a pre-shaped or alternatively made from a material which accepts the shape of the area after placement. Pieces of shaped foams or pads may also be placed between the wound dressing and these supports. A flat, fluid-filled balloon attached to a measurement unit may be placed between the support and lining to monitor the pressure in the wound.

FIG. 7A shows a support unit for the leg as shown at FIG. 6C, except this figure shows a U-shaped extension attached to it. In this figure the support, shown at FIG. 6C, has an extension which will function as the inner support, I-SUP. This piece moves down and covers the inner ankle and then connects to a piece of strap shown at U-STR. This follows a model which was shown at FIG. 7.

FIG. 7B shows the side views of a U shape extension for use with the leg support. This unit is designed to support the upper and lower ankle and allows the compression of these area for prevention and the treatment of the wounds particularly, in the inner, lower leg and the ankle area. This figure shows rather rigid inner and outer supports, I-RIG-SUP and the O-RIG-SUP that are made from rather rigid pieces such as a shaped polymer or metal. The outer surface of these supports have zones of attachment means, such as hook fastener, ATM2S-A and ATM2S-B. These allow a series of horizontal straps, such as the band C-BAND shown at FIG. 7 and other wider straps (particularly made from LYCRA™.) to wrap around them and hold the inner and outer rigid supports, I-RIG-SUP and the O-RIG-SUP. This method will squeeze these support together for further compressing the lower leg-inner ankle, tissues in between. The lower ends/poles of the inner and outer supports, I-RIG-SUP and the O-RIG-SUP are attached to each other by use of an elastic strap or loop attachment means, ATM1-S, that attach to the inner and outer zones of hook attachment means I-ATM2S and O-ATM2S on a detachable, re-attachable basis. This method allows the distance between the two inner and outer supports, I-RIG-SUP and the O-RIG-SUP to be adjusted to match the width of the ankle area. The inner surface of the inner and outer supports, I-RIG-SUP and the O-RIG-SUP has a zone of hook attachment means, ATM2 that allows a pad made from a foam shown at FIG. 7C to attach to the inner surface of the supports on a detachable, re-attachable basis.

These supports, will hold one or two pads made from one or two kinds of foams, FOAM, (shown at FIG. 7C) that allow the ankle area to be compressed by the use of this pad. The foam pad is designed in the following manner.

1. A layer of rather non-compressible foam that stands outside of the ankle area.
2. A layer of rather soft foam that stands on the ankle area and allows this foam to accept the shape of the ankle area.
3. A soft lining that will cover the inner surface, the inner foam and will stand on the wound dressing of the ankle.
4. Importantly, this pad has an opening, OP shown at FIG. 7C which is designed to stand on the inner and outer bony prominences of the ankle. This is critically important, since this method allows the soft tissue of the ankle to be compressed, without pressing the bony prominences of the ankle. Without this design the boney prominences will prevent proper transmission of the pressure of the pads to the soft tissue of these areas.

The outer surface of the non-compressible foam has a zone of attachment means, ATM1-F that allows this pad to attach to the inner surface of the inner and outer supports, I-RIG-SUP and the O-RIG-SUP on a detachable, re-attachable basis.

A series of elastic straps will wrap around the inner and the outer supports, I-RIG-SUP and O-RIG-SUP for squeezing these two supports toward each other to compress the lower leg-inner ankle tissue in between.

Importantly, a flat fluid filled balloon attached to a measurement unit, (as shown at FIG. 7D) may be placed under the inner support and between another rather rigid unit on the foam, FOAM. This balloon has a shape and size that matches the support.

FIG. 7C shows schematically a padding made of a foam, FOAM for placement under the support, that allows the pressure in the wound area to be applied to the soft tissue. The outer surface of the pad, FOAM has a zone of attachment means, ATM1-F, that allows this pad to attach to the inner surface of the inner and outer supports, I-RIG-SUP and the O-RIG-SUP on a detachable, re-attachable basis. Importantly, this unit shows the opening, OP designed to stand on the inner and outer bony prominence of the ankle. This is critically important, since this method allows the soft tissue of the ankle to be compressed. Without this design the boney prominences will prevent from proper transmission of the pressure of the pads to the soft tissue of these areas.

FIG. 7D shows schematically an inflation unit for use with the unit shown at FIG. 7B. This unit consist of a flat fluid, filled inflatable balloon, IB which is attached to a measurement unit, shown at gauge, G by use of a three-way stopcock, TWS. The unit inflates by use of a pump, P. When the optimum pressure inside the balloon is achieved the three-way stopcock can be closed and the pump and gauge removed.

The inflatable balloon, IB will be placed under the inner support, I-RIG-SUP with a detachable, re-attachable basis. Importantly, the system may be a closed unit to allow the pressure to be noted all the time. An alarm unit may be incorporated to allow the significant change in pressure. The inner and outer surfaces of this balloon will have zones of attachment means that will complement the attachment means of the inner support, I-RIG-SUP and the padding so that it will be hold in place securely.

FIG. 7E shows schematically, the general view of a support unit for the feet. This is designed to prevent from the compression of the heel and the sides of the ankle and may be used with the units shown at FIGS. 6-7 for preventing the bed sores in the heel, ankles and the foot. This unit consists of a piece of thick foam means, FO, a balloon or similar pad that is round-shaped for being placed on the ankle area and for being wrapped around it. The thickness and the width of this foam means, FO will prevent the bony parts of the heels and ankles to reach the mattress. Thus, it will prevent from pressure sores. This unit, FO will be held in place properly by the following method that consists 1. Attaching the free ends of the foam means, FO together by use of hook and loop fastening means, shown at ATM2-L and ATM1-L that are placed in its ends. The ATM2-L is a piece of hook fastener that will attach to the zone of loop attachment fastener, ATM1-L from the body of the foam, FO on a detachable, re-attachable basis.
2. An elastic strap, STR shown at left is made from a double-sided Lycra (™) that has a free end with a zone of hook attachment means, ATM2-F. The inner end of the strap, STR is attached to the side of the foam, FO somewhat distant from its end. At the side of attachment to the foam, FO the strap, STR has a zone of loop attachment means, ATM1-F. The loop-fastener, attachment means, zone ATM1-F may be part of the foam, FO or attached to it. The strap, STR is sized to move down from one side of the ankle and wrap around the sole of feet in a U-shaped fashion, and then to move up in the other side of the ankle to attach to the hook attachment means, ATM2-S on the side of the foam, FO.
3. Then, the strap, STR, will be further pulled in front of the shin to attach to the zone of the loop-fastener, attachment means, ATM1-F, on the strap and on a detachable, re-attachable basis, by use of ATM2-F.

Importantly, by this method the elastic strap, STR, will create a reasonable tension for keeping the foam, FO, in place securely. This method will prevent the foam, FO to move up in the leg and the prominence of the ankle of the humans will prevent the foam, FO from moving further down to the foot.

It is very important that the body of the elastic strap, STR, is not irritant to the leg. This is an advantage and makes the use of such a unit possible.

Please note that the design of this unit is important since it will prevent from:
a. Up and down movement of the foam, FO along the shin.
b. The rotation of the foam, FO around the shin, due to the presence of the strap, STR in the front of the shin which will prevent from such a move.
c. Importantly, the body of the strap, STR, allows it to attach to the surface of the foam, FO by attaching to the attachment means, ATM2-S, from the foam, FO, due to the special property of the strap. This is a critical issue that plays a very important role in the function of this unit and helps to keep it secure.

Importantly, the strap, STR may be made to be a Y-shaped strap with two end pieces, in order to allow one of the ends of the strap to move in the rear part of the leg and the other end of the strap to move in front of the leg and to attach to the ATM1-F. This may give some more stability to these units.

Importantly, the strap may also have an attachment means to allow it to be attached to the hook of a leg elevator unit, described in this application at FIG. 34.

Please note that the foam, FO may have a cover made from fabric on its surface or to go over it in order to make it a comfortable unit and to allow the attachment means to be fixed on it.

The foam may have extra pieces attached to it to add thickness to the body of the foam. The shape of the foam may vary and have more thickness in the bottom to prevent from the heel reaching the surface of the bed etc.

Also the unit may use a pad of foam, FOAM, shown in lower left side of this figure which is designed for placement on the sole. It will be held in place by the strap, STR, and will function to prevent the sole of the user from touching the lower board of the bed.

This unit may be used with the units shown at FIGS. 6-7 to prevent from pressure to the foot. In this case, the unit may be used alone or to be attached to the sides of the U shaped supports.

FIG. 7F shows schematically the view of the unit shown at FIG. 7E when viewed from the side. In this view, the body of thick foam means, FO, is shown with a zone of hook-fastener attachment means, ATM2-S on the right side of the foam, FO. The cross-cut of the strap, STR, is shown on the left with the zone of the loop-fastener, attachment means, ATM1-F attached to the foam, FO and the zone of hook-fastener, attachment means, ATM2-F on its left border.

FIG. 7G shows schematically the side view of the unit shown at FIGS. 7E-F when it is placed on a leg. In this view, the body of foam means, FO, is standing around the leg with having the piece of hook-fastener attachment means, ATM2-L being attached to the zone of loop-fastener attachment means, ATM1-L from the body of the foam, FO. The strap, STR has pulled down from the side of the ankle and wraps around the sole of feet in a U-shaped fashion, then has moved up on the other side of the ankle and is attached to the hook-fastener, attachment means, ATM2-S on the side of the foam, FO which cannot be seen in this view. Then the strap, STR is further pulled in front of the shin and is attached to the zone of the loop-fastener, attachment means, ATM1-F (not shown in this figure) due to the attachment of the ATM2-F. In this figure only the attachment means, ATM2-F, is shown. The foam, FOAM, is also not shown to prevent crowding the illustrations.

FIG. 8 shows the front view of a special stretchable support unit made from shaping the same material used for the strap or the LYCRA (™). Here, the Lycra is modified with use of bands made from materials such as latex as shown at L-BAND. The shaping of this stretchable material or the use of sewing techniques allow an elastic, shaped support to be made. Such a support is useful in areas with a particular shape and function, such as knees, ankles, elbows, toes, etc. This shaped, stretchable support allows better handling and placement of these units. Importantly, the following advantages are also available:
  a. In this method the support has an elastic body that will be pulled to keep it in place with a comfortable tension. This mild, comfortable tension is an important property for use in these areas.
  b. The support unit stretches and conforms to some degree and accepts the shape of the area. Also, such a body allows this body of the support to change with change of the wound areas such as over joints, knees, ankles, hips, elbows with extension and closure.
  c. The inner part of the support is a soft, non-irritant fabric and does not cause skin reaction.
  d. On the scalp it allows an easy dressing of the wound.
  e. Importantly, the side where the strap is attached stretches in both direction and allows this unit to fit a shaped area, such as the scalp. A transverse strap allow this unit to be further stable on the scalp. This will make a cross-shaped unit.

In this figure the attachment means of the support is shown at ATM2 and the strap at STR. A D-Ring may also allow the strap to be adjusted.

FIG. 9. Shows a long strap that is attached to a transparent support, SUP. This figure also illustrates two important parts:
1. a transparent pocket for placement of information, here referred to as the Information Pocket, IP which is on the support, SUP or on the strap. The Information Pocket, IP, allows a piece of paper, consisting information to be placed inside the pocket. This information may be, for example, time of the use of the dressing, medication underlying IV line, or other information about the person using the unit, etc., and can be exchanged as needed.

Importantly, the information pocket, IP, may be placed on the wall of the strap to be part of the wall or simply attached to it.

2. Importantly, the body of the straps, STR, may have zones of materials such as latex, LA, in or on it in order to allow the shape of the strap to be conformed or modified to a desired shape. It can be used to prevent curling of the strap, etc. The shape, width, thickness, materials utilized, and other characteristics of these zones may vary.

3. Also Importantly, the body of the strap may have zones of adhesive shown at ADH, to allow the strap to be adhered to the skin when needed. The adhesive layer will have a protective cover which will be removed before use.

Importantly, two strap may criss-cross to allow a better placement. This is more useful in strapping the head wounds, in which one strap will go around the front and occipital area and the other from the vertex to area below the under chin.

FIG. 10. Shows schematically the use of D-Rings with the support unit. In this figure a transparent support, SUP has a D ring, D-RING on its right side that allows the strap of the unit to go through, make a U-turn, and attach to its own surface. This is another method of adjusting the length of the strap as mentioned in the text.

FIG. 11. Shows schematically a cradle, CR, on a stand that allows a limb to be placed on it. The angle and height of the cradle can be adjusted by means connected to the base, BA. The height can be adjusted by control of the height of the pole, PO and the angulation by the hinge, HI. This unit allows a strap or the support part of the support unit, shown at FIGS. 3-4 to be placed on the cradle of this unit and be attached to it by use of a weak adhesive or by a detachable, re-attachable means. Thus, the combination allows the user to place the support on a limb with one hand and adjust its size and tension. This unit may also be useful in dressing of the wound by hand. This unit may have an exchangeable lining in case the user wants to change them.

FIG. 12 shows a general view of the rear piece of a support unit designed for use for the supporting of the wounds on the heels and toes. In this figure the piece that stands on the heel is shown at, HE and it has a lower sole, SOL-1 that has a hook-fastener attachment means, ATM2, on its surface. This piece also has a strap, STR-1 with a zone of hook-fastener, attachment means, ATM2, on its end this piece complements the piece shown at FIG. 13 to make a unit shown at FIG. 14.

Importantly, these heel and toe pieces which may be made from shaped Lycra (™) or similar fabric, with use of latex material as mentioned, so that this combination will:
a. Be soft, non-irritant and comfortable.
b. Allow the unit to be pulled to accept the form of the underlying area and fit well.
c. Allow one size to be used in many patients.
d. Allow the pieces to be placed inside one another and so that many of them, such as 15-20 at a time, may be placed inside one box, thus reducing storage size.
e. Allow the patients themselves to adjust the length of the unit as needed.
f. Importantly, both the heel and front pieces may have a cut with a strap on their lengths to allow their width to be adjusted as well. The strap will hold the open area in control.
g. Importantly, both the heel and front pieces themselves may be made from two pieces to allow the width to be adjusted as one piece can be attached to the other one along a zone of attachment of a detachable, re-attachable basis.
h, Importantly, these pieces may be made from other shaped materials.

Importantly, the attachment means will be complementary and one attachment means, ATM, will be faced with a complementary attachment means on the other side. Or, the body of the shaped areas will function as the complementary attachment means. This method allows, for example, the attachment means in the straps to be hook-fastener attachment means, ATM2, to be attached to the surface of the body of the heels made from loop-fastener attachment means.

FIG. 13 shows the general view of the front piece of the support unit shown at FIG. 12. In this figure the front piece, FR, also has a sole, SOL-2, that allows the hook-fastener attachment means, ATM2, from the rear piece shown at FIG. 12 to attach to its surface on a detachable, re-attachable basis. This piece has a strap with a piece of hook-fastener attachment means on its end. The front and rear pieces of these units are made from shaped materials.

FIG. 14 shows schematically the general view of the support unit for the heels and toes made from the combination of rear piece shown at FIG. 12, and front piece shown at FIG. 13. In this figure, sole, SOL-1, from the rear piece is attached to SOL-2 from the front piece on a detachable, re-attachable basis. Importantly, this allows the length of the unit to be adjusted. The strap STR-2 holds strap STR-1 from the rear piece and attaches to its own surface by the attachment means on a detachable, re-attachable basis. The strap STR-1 from the rear piece, HE, attaches to the body of the rear piece, HE, on a detachable, re-attachable basis.

FIG. 15 shows schematically a support unit for the heels and toes, made from the combination of the unit shown at FIG. 14, which is placed inside an outer piece that functions as the body of a shoe. The outer piece is made from a front sole shown at SOL-3 that is attached to the SOL-4 from a rear piece, OHE on a detachable, re-attachable basis. The combination is attached to the piece shown at FIG. 14 by attachment means between them.

This combination has the advantage of allowing an adjustable piece be used for use both in and out of the house. The outer piece will be removed inside the house and used when leaving the house.

The use of heel and foot protector with these units:

Importantly, these units allow pieces of foam to be attached to their surfaces in order to prevent bed sores in these areas. For this purpose, shaped sponges will be attached to these pieces and prevent pressure sores. The shaped sponges may have open spaces in particular pressure areas to avoid pressure to those sensitive areas. It is important to note that the use of soles allow the sponges to be kept in place securely and not to rotate as commonly occurs.

FIG. 15A shows schematically the general view of a simple support unit for the dressing of the toes. This unit has a pocket, POK, made from combination of a front and rear wall that are attached to each other along their borders shown at lines, SEW. In this particular model, the fabric is folded so the front border is closed as well. The rear wall of this unit has two elastic straps, STR-1 and STR-2, which are made from Lycra and are attached to the body of the rear wall. The free ends of these straps have a complementary attachment means made from loop-fastener attachment means shown at ATM1 and hook-fastener attachment means, ATM2 respectively. Please note that one of the attachment means will be in front of one of the straps and the other will be on the rear surface of the other strap. This method will allow the end of these straps to attach to each other on a detachable, re-attachable basis.

At the time of use:
a. The pocket of the support, POC, will be placed in front of the foot and will cover the toes and its dressings. In this position, the straps will be under the sole.
b. The strap, STR1, will be pulled to wrap around the heel to move up and cover the front of the ankle. This will be kept in position to allow the end of the other strap to attach to it.
c. The second strap, STR2, will be pulled to wrap around the heel and move up from the other side of the ankle so that its free end will attach to the attachment means, ATM1, from the strap, STR1.

This method will make a secure and simple means of holding the dressing of the toes in its place which is commonly difficult.

The support may be made from:
1. Elastic fabric
2. A regular fabric
3. A thicker unit such as body of the supports as mentioned.
4. Various materials may be used.
5. The attachment of the straps to the body of the support may vary.

However, making this unit from the LYCRA (™) makes a very nice comfortable unit that has many advantage such as:
a. A support with an elastic body that will be pulled to keep it in place with a comfortable tension. This mild, comfortable, tension is an important property for keeping the dressing in place.
b. The support unit stretches and conforms to some degree and accepts the shape of the area.
c. The support is a soft, non-irritant fabric and does not cause skin reaction.

FIG. 15B shows schematically, the general view of support unit similar to the unit shown at FIG. 15A, except the two straps of this unit, STR-A, and strap, STR-B are placed in different directions. This unit also has a pocket, POK, made from a folded layer of an stretchable fabric, particularly, LYCRA (™) with sides that are sewn or attached together along the lines, SEW. The outer/top surface of this pocket, POK has a zone of loop-fastener, attachment means, ATM1-AB. The rear/bottom surface of the pocket, POK, has one elastic strap, STR-A made from LYCRA (™) attached to it. The free end of the strap, STR-A, has an zone of loop-fastener, attachment means, ATM2-A, that allows this strap to wrap around the ankle and attach to the attachment means, ATM1-AB of the top of the pocket, POK. Importantly, when the body of the pocket is made from LYCRA (™) then the ATM2-A, of the strap, STR-A, will attach to the outer surface of the pocket, POK, on a detachable, re-attachable basis and in any part of the pocket.

The unit may have another elastic strap, STR-B, made from LYCRA (™) that wraps around the base of the pocket, POK, and attaches to the loop-fastener, attachment means, ATM1-AB or the body of the pocket, POK, on a detachable, re-attachable basis. The function of the strap, STR-B, is to hold the base of the pocket together if there is a need for it.

Method of use.
1. The dressing will be placed on the wound and may be held momentarily in place by an elastic loop, E-LO, shown in the left lower part of this figure and is made from LYCRA (™).
2. The pocket, POK, will be pulled over the dressing via its opening, OP.
3. The elastic strap, STR-A, will be pulled to go around the ankle to have the zone of the loop-fastener, attachment, ATM2, of its free end to attach to the zone of loop-fastener, attachment means, ATM1-AB from the body of the pocket, POK.
4. The second strap, STR-B, will wrap around the bottom of the foot and will pull the side of the pocket and then the zone of the loop-fastener, attachment means, ATM2-B, of its free end, will attach to the zone, ATM1-AB, from the pocket, POK, or to the body of the pocket, POK.

This makes a simple unit that allows an easy dressing of the wound and its opening and closing.

The pocket may be made from.
1. Elastic fabric, particularly the LYCRA (™).
2. A regular fabric
3. A thicker unit such as body of the supports as mentioned.
4. Latex or any other man made materials.
5. The attachment of the straps to the body of the support may vary.

Importantly, this unit may have two straps similar to the strap STR-A, attached to the lower/bottom layer of the pocket, POK, in order to each one to move from one side of the ankle, as shown in previous figure.

FIG. 16 shows the top view of a buckle means designed to allow the length of the strap to be adjusted and a more durable, convenient unit for use with these units. This unit allows the length of the strap to be adjusted initially and yet allow some further adjustment after the initial placement of the strap on the support. This buckle consists of a lower flat piece, LP, and an upper flat piece, UP, that are hinged at hinge, HI. The other end of the upper piece, UP, will be snapped to the lower piece, LP, by the snap, SNAP. The snap allows the upper piece to be opened and closed along the hinge, HI. The upper piece, UP, has a series of spins, SPIN, on its lower surface that, when the buckle is closed, allow the strap to move in a one way direction as the arrows point and not be pulled back. The upper surface of the upper piece, UP consists of attachment means, ATM that allows the end of the strap to be attached to it on a detachable, re-attachable basis. Importantly, the spins may be placed on the upper surface of the lower piece, LP.

The lower surface of the lower piece, LP, consists of a loop-fastener. attachment means, ATM, that allows it to be attached to the hook-fastener attachment means of the surface of the support on a detachable, re-attachable basis. At the time of use the strap will be pulled in the direction of the arrows and will be placed between the upper, UP, and lower pieces, LP. Then it will make a U-turn along the border of the upper piece, UP, and attach to the surface of the upper piece, UP, by itself or with the help of a matching attachment means or weak adhesive, with the extra length cut after length adjustment. The free end of the strap will finally be attached to this buckle and the buckle attached to the support, SUP, on a detachable, re-attachable basis. The extra length of the strap will allow its length to be adjusted and the position of the buckle on the support allows the effective length of the strap to be adjusted as well. The snap, SNAP, allows the upper piece, UP, to be opened and the strap be moved back and forth for the length adjustment.

FIG. 17 shows a vertical, horizontal, cross-cut view of a buckle piece shown at FIG. 16. In this figure the lower flat piece, LP, is shown and its lower surface consists of attachment means, ATM. The upper surface of the upper piece, UP, has hook-fastener attachment means, ATM2, that allow the end of the strap to be attached to it on a detachable, re-attachable basis.

The lower surface of the upper piece, UP, has the spin, SPIN. At the time of use the strap will be pulled in the direction of the straight arrow, and then the unit will be snapped and the rest of the strap will make a U-turn in the direction of the curved arrow to attach to the attachment means of the upper surface of the upper piece, UP.

FIG. 17A shows a vertical, longitudinal, cross-cut view of a buckle piece shown at FIG. 16. In this figure the lower flat piece, LP, is shown and its lower surface consists of attachment means, ATM. The upper piece, UP, is hinged to the lower piece, LP, at hinge, HI. The upper surface of the upper piece, UP, consists of attachment means, ATM2, the spin, SPIN, is shown at the lower surface of the upper piece, UP, and the snap, SNAP, is also shown.

FIG. 18 shows the front view of an end unit, designed to allow the length of the strap to be adjusted. This unit has a rectangular, flat base, BASE, made from a layer of fabric with a zone of hook-fastener attachment means on its right side, ATM2, placed on its upper and lower surfaces. Here, the upper zone of attachment means, U-ATM2 is shown on the right side. A similar zone on the left side is made with a layer of adhesive on it, shown at ADH, at FIG. 18A, which is protected by a protective cover, PC. The inner edge of the protective cover is shown at BPC. The lower surface of the base in the right side also has attachment means, L-ATM2, best shown at FIG. 18A. This unit gives significant advantage and will allow the length of the strap to be adjusted for many units such as the heel and shoulder and other units.

Importantly, instead of U-ATM2 the unit may have a zone of adhesive to allow the fabric to attach to this zone. The adhesive zone will be protected by a protective cover similar to the piece shown at, PC At the time of use:
1. Initially this piece will be attached in a proper position to the body of the outer surface of the support, SUP.
2. Then the strap will be pulled to attach to the ATM2 zone of this piece, which will be possible due to the capability of the strap.
3. When the proper length of the strap is decided, then the extra piece of strap will be cut along the left border of the upper attachment means, ATM2 on the upper surface of this unit. Please note that at this point the strap is attached to hook-fastener attachment means, ATM2, from the upper surface of this piece.
4. Then the user will remove the protective cover, PC, and adhere the lower or base of this piece to the upper surface of the strap through use of the adhesive layer.

This combination will make:
a. The free end of the strap have a neat cut.
b. The combination make a zone of hook-fastener, attachment means, ATM2, in the lower surface of the free end of the strap that will be used to attach the free end of the strap to the outer surface of special supports that will accept this end. This will be very useful in units for use in various areas, such the heels and shoulder, etc.

The advantage of this unit is that allows a one-size unit to be used as a universal unit or will allow a better adjustment of the length of the straps.

FIG. 18A shows the cross cut view of the unit shown at FIG. 18. In this picture the unit has base, BASE, made from a layer of fabric, with a zone of hook, fastener, attachment means, ATM2 on its upper and lower surfaces shown in the right side. On the upper surface of the left half of the base, the fabric has a layer of adhesive, ADH, that has a protective cover, PC, on it. At the time of use this piece will be attached to the top surface of a matching support by virtue of the lower attachment means, L-ATM2. The elastic strap will attach to the upper attachment mean, U-ATM2, of end unit and with adjustment, proper length of the strap will be known and then the extra piece will be cut along the left border of the upper attachment means which is on the border of the protective cover. Then the user will remove the protective cover, PC, and adhere the base to the upper surface of the strap. This will make a clean-cut side and the combination will make a zone of attachment means, ATM2, on the lower end of the strap that will be used to attach the end of the strap to the surface of the units for use in the heel and shoulder, etc.

Again please note that, instead of U-ATM2 the unit may have a zone of adhesive to allow the fabric to attach to this zone. The adhesive zone will be protected by a protective cover similar to the piece shown at, PC.

FIG. 18B (also note FIG. 18C) shows the front view of an end unit shown at FIG. 18 that is placed on a support, SUP. This support has a non-stretchable body with an outer surface made from a layer of loop-fastener, attachment means, ATM1, its inner surface being a soft lining that stands on the skin, and a thin layer of foam sandwiched in between. The strap, STR, is attached to the right border of the support. The outer surface of the left border of the support, SUP, has a long, narrow zone of hook-fastener attachment means, ATM2. The end unit piece is attached to the surface of the support, SUP, due to the attachment means, ATM2, in its lower surface, this part is shown better in FIG. 18C.

FIG. 18C shows the vertical, cross-cut view of the support, SUP, shown at FIG. 18B with an end piece close and parallel to it. The strap is not shown. The upper layer of the support is a loop-fastener attachment means, marked at ATM1, and its lower surface is a soft lining, LIN, the layer of foam, FOAM is in between. The end unit is shown on top of the surface of the support, SUP, and consists of a base, BASE, made from a layer of fabric or a polymer. A zone of hook-fastener attachment means, ATM2 is on its upper surface, U-ATM2, and another zone of hook-fastener attachment means is in the lower surface of this piece but is not marked. The other segment of the base, BASE has a layer of adhesive shown at ADH, that has a protective cover, PC, on it.

The method of use:
1. Initially the end unit will be attached to the body of the outer surface of the support, SUP, due to its loop, fastener attachment means, ATM2.
2. Then the strap will wrap around the limb and be pulled to attach to the zone of ATM2 shown on the left border of the support, SUP. This occurs due to the strap's own capability that functions as a loop-fastener attachment means. This step allows the length of the strap to be decided.
3. After the proper length of the strap is decided, it will be further to attach to the upper attachment means, U-ATM2, of the end piece.
4. The extra strap will be cut along the right border of the upper attachment means, U-ATM2, on the upper surface of this piece. Please note that at this point the strap is attached to the U-ATM2 from the outer surface of this piece.
5. Then the user will remove the protective cover, PC, and adhere the base, BASE to the upper surface of the strap by use of the adhesive layer.

At this point the lower surface of the end piece is attached to the upper surface of the support by virtue of the lower attachment means, ATM2 and importantly, its position may be further changed by moving it back and forth on the support.

FIG. 18D shows the vertical, cross-cut view of a mating piece that allows the unit shown at FIG. 18 to be used with a support that is made from a material, such as vinyl, that does not have the loop-fastener means on its own surface. This piece has an outer surface made from a loop-fastener attachment means, ATM1, and its lower surface has a layer of adhesive shown at ADH covered with a protective cover, PC, on it.

The method of use:
1. Initially the protective cover, PC, of this mating piece will be removed and the unit adhered to the outer surface of the support, SUP.

This will modify the vinyl or similar supports, and allow the end piece shown at FIG. 18 to be attached to the loop-fastener attachment means, ATM1, of this piece to function.

FIG. 19 shows the general view of a support unit designed for use in the head. This unit consists of two similar pieces of support units, SUP-A and SUP-B, that will be attached to each other by use of straps, H-STR and C-STR. The supports have a trapezoid body as shown at SUP-A, with a wider, upper area for the head area and a narrower, lower area for placement on the chin area. Importantly, this support has a laminated body with an outer layer made of loop-fastener attachment means, ATM1, an inner layer which is a soft, fabric, lining to contact skin and a layer of foam in between. In the units shown here, the outer surfaces of the supports, SUP-A and SUP-B have two zones of long and narrow hook-fastener attachment means, ATM2, that allow the body of a strap shown at FIG. 21 made from lycra with a smaller support on its end almost similar to the one shown at FIGS. 1-4 to be attached to it on a detachable, re-attachable basis. This strap, shown in more detail at FIG. 21, will attach to the unit shown at FIG. 19 on a detachable, re-attachable basis. This is important since the body of this particular strap allows such an attachment which keeps the unit stable and prevents it from moving.

The upper border of the trapezoid support, SUP-A, has two stretchable straps made from Lycra, shown at H-STR. These straps attach to the upper areas or the head areas of these supports, SUP-A AND SUP-B to keep them together on a stretchable, detachable and re-attachable basis. The free ends of the head straps, H-STR have a hook-fastener attachment means, ATM2, that allow the ends of these straps to be attached to the outer surface of the other support, SUP-B, on a detachable, re-attachable basis.

The lower border of the support, SUP-A, for the chin area also has two stretchable, but narrower, straps made from Lycra, shown at C-STR, that attaches the chin areas of the supports SUP-A and SUP-B, to each other on a stretchable, detachable and re-attachable basis. The free ends of these two chin straps, C-STR have small zones of hook-fastener attachment means, ATM2 that allow the ends of these straps to be attached to the outer surface of the second support, SUP-B, on a detachable re-attachable basis.

The second support, SUP-B, has similar a body, except that it does not have the H-STR and C-STR straps, since these straps will be shared and attached to it on a detachable, re-attachable basis.

FIG. 20 shows schematically the side view of the unit for the head shown at FIG. 19. In this figure the body of the support, SUP-A, is shown. This has a laminated body with an outer surface made from a layer of loop, fastener attachment means, ATM1, an inner layer made from a layer of soft fabric lining, LIN, and a layer of foam, FO, sandwiched between. The elastic strap for the head is shown at H-STR and the elastic strap for the chin is shown at C-STR. Both of these have zones of attachment means, ATM2. The body of the support, SUP-B, is shown in the right side of the figure and has similar body as the support, SUP-A.

FIG. 21 shows schematically the general view of a complementary strap for use with the unit shown at FIG. 19. This strap is similar to the strap shown at FIGS. 1-4. Basically, this figure shows a long, stretchable strap, STR, that is attached to a support, SUP. The support has a zone of hook-fastener, attachment means, ATM2, on its front/outer surface that allows the body of strap, STR, to attach to it on a detachable, re-attachable basis. The rear surface of this support, STR, may also have another zone of hook-fastener attachment means, ATM2, (which cannot be seen in this view) that allows the support, SUP, from this strap to attach to the outer surface of the support, SUP-A or SUP-B, for the head on a detachable, re-attachable basis. Please note that the support for the head, has a laminated body with an outer layer made from a layer of loop-fastener attachment means.

The free end of the strap, STR, shown on the left side of this figure has an adhesive piece similar to one shown at FIGS. 1-4 that allows the end of this strap to be attached to the outer surface of the strap, STR. This can also have a zone of hook-fastener attachment means, ATM2.

This combination of strap and head supports, SUP-A and SUP-B, makes a very stable and versatile unit for the wounds of the head and face.

This unit allows the head straps, H-STR, to be opened for adjusting the size or the tension of unit or for the examination of the wound site. Also the chin straps, C-STR allow the size and the tension of the unit to be adjusted, as well. The strap, STR, goes horizontally around the head and allows the size of the strap and thus, the horizontal tension, to be adjusted. Also, it allows the wounds in the occipital or the frontal part of the head to be checked.

FIG. 22 shows schematically the general view of a support unit for the shoulder. This unit has a non-stretchable support unit shown as ARM-SUP, that covers the outer side of the arm. This support has a laminated body with an outer layer made from a loop-fastener attachment means, ATM1, and an inner layer which is a soft fabric lining to contact skin and a layer of foam/sponge in between. In the units shown here, the outer surface of the support, SUP, will have at least two long and narrow zones of hook-fastener attachment means, ATM2. This allows the body of an arm strap, ARM-STR, made from LYCRA (™), with a smaller support on its free end, almost similar to the one shown at FIGS. 1-4 to be attached to the ARM-SUP, the strap, ARM-STR, is designed to wrap around the upper arm and attach to the surface of the ARM-SUP on a detachable, re-attachable basis.

Another wider, elastic shoulder strap, SH-STR, is also made from LYCRA (™) and is attached to the upper border of the ARM-SUP. The shoulder strap, SH-STR is designed to cover the shoulder and keep the dressing on it. Importantly, the stretchable body of this strap allows the shoulder to move easily and keeps the dressing secure. The shoulder strap, SH-STR, has two support pieces of its own, FR-SUP and RE-SUP, that cover the front and rear upper part of the chest. These two supports are made from the same material as the arm support, ARM-SUP, and have zones of hook-fastener attachment means, ATM2, on their front/outer surfaces.

At the time of use, the FR-SUP is placed on the front of the upper chest and the RE-SUP placed on the rear surface of the chest on the user's back. A strap shown at FIG. 23 goes in front of the chest and wraps around the opposite armpit, with one free end of the strap attaching to the outer surface of the FR-SUP and the other free end attaches to the outer surface of the RE-SUP on a detachable, re-attachable basis.

A piece of support, shown as axillary sup, AX-SUP, in FIG. 23 which is made from same laminated material stands under the armpit and under the strap and functions as a stabilizer, preventing the strap from curling.

Method of use:
1. The body of the arm strap, ARM-STR, will wrap around the arm and first attach to the attachment zone, ATM2, from the arm-support, ARM-SUP, due to the special property of the strap that functions as the loop-attachment means. Then the hook-fastener attachment means, ATM2, of the free end of the arm strap, ARM-STR, will attach to the outer surface of the arm support, ARM-SUP, on a detachable re-attachable basis. This will hold the arm support, ARM-SUP on the outer surface of the arm in a stable, comfortable fashion.
2. The shoulder strap will next be wrapped on the shoulder area; so that its front support, FR-SUP, is on the front of the upper chest and its rear support, RE-SUP, placed on the rear surface of the chest.
3. One free end of strap, STR, shown at FIG. 23 will be attached to the outer surface of the front support, FR-SUP, due to the attachment means on both sides, and will be pulled on the front of the chest to create a comfortable tension. It will then be attached to the outer surface of the axillary sup, AX-SUP, shown in FIG. 23, in a proper spot so that the axillary sup, AX-SUP, will be comfortably under the armpit. The attachment of the strap, STR, to the axillary sup, AX-SUP, is on a detachable, re-attachable basis. Please note that the axillary sup, AX-SUP, is made from a laminated material and has a zone of hook-fastener attachment means on its own outer surface that allows the attachment of the strap, STR, to its outer body. This axillary sup, AX-SUP functions as a stabilizer and prevents the strap from curling.
4. Then the free end of the strap, STR, will be pulled on the back of the chest, and be attached to the outer surface of the RE-SUP on a detachable, re-attachable basis.

This method and means makes a stable, comfortable support for the shoulder joint. Importantly, one end of the strap for the chest will be attached first, and a buckle system as shown at FIGS. 16-18 (or similar units) may be used to adjust the length of this strap.

FIG. 23 shows schematically the general view of the strap for the shoulder support unit shown at FIG. 22. In this figure the body of the axillary support, AX-SUP, is shown. The front/outer surface of this support has a zone of hook-fastener attachment means, ATM2, which is under the strap, STR, and cannot be seen in this view. Both free ends of the strap, STR, have zones of hook-fastener attachment means, ATM2. The axillary support, AX-SUP, covers the axillary area and will keep the strap, STR, in proper position, simultaneously preventing it from curling.

FIG. 24 shows schematically the general view of a support unit for the ankle. This unit also consists of a non-stretchable, support, shown at, HEEL-SUP, that stands on the front or the upper surface of the ankle. The heel support, HEEL-SUP, is made from laminated material with an outer surface made from a layer of loop attachment means, ATM1, an inner surface, a soft lining to contact skin with a thin layer of foam in between. The outer surface of the support has a zone of hook-fastener attachment means, shown at ATM2-HS. The support may have a second zone of hook-fastener attachment means parallel to ATM2-HS. An elastic strap, made from LYCRA (™) shown at HEEL-STR, is attached to the right border of the HEEL-SUP. The free end of this strap has a zone of loop-fastener attachment means, ATM2-H-ST. This strap will wrap around the heel and attach to the outer surface of the heel support, HEEL-SUP, on a detachable, re-attachable basis. The two bands, BAND-A and BAND-B, are similar to the bands shown at FIGS. 1-2, except they are located in the same site as the main strap. These bands will wrap around the ankle on each side and attach to the zone of the hook-fastener attachment means, ATM2-HS, from the support HEEL-SUP on a detachable, re-attachable basis due to their own property. These bands may have their own zones of hook attachment means, ATM2-A and ATM2-B as shown, which may be attached to the outer surface of the HEEL-SUP. Importantly, the heel strap, HEEL-STR, and the bands, BAND-A and BAND-B, are made from a special material (LYCRA.™) that has a loop fastener function and allows these pieces to attach to the hook attachment means, ATM2-HS, on a detachable, re-attachable basis. This facilitates the application of this unit significantly, and has a very significant importance.

Method of use.
a. The user will place the heel-support, HEEL-SUP, on the front/upper surface of the heel.
b. The user will wrap one of the bands, BAND-A or the BAND-B around the ankle joint on its upper part and attach it to the hook attachment zone, ATM2-HS from the heel-support, HEEL-SUP, on a detachable, reattachable basis. This will hold the support in place and allow further attachments.
c. The user will wrap the second band, BAND-B or BAND-A, around the lower part of the ankle joint and attach it to the hook attachment zone, ATM2-HS from the heel-support, HEEL-SUP, on a detachable, reattachable basis. This will hold the support in place with even more stability and allow the attachment of the heel strap, HEEL-STR.

d. Then the heel strap, HEEL-STR, will be wrapped around the heel and be first attached to the attachment zone, ATM2-HS from the heel-support, HEEL-SUP, due to the special property of the body of strap that functions as the stretchable, loop attachment means. Then the hook-fastener, attachment means, ATM2-H-ST, of the free end of this strap will attach to the outer surface of the heel support, HEEL-SUP on a detachable re-attachable basis.

This method makes a comfortable, sturdy unit on the heel. The elastic heel strap, HEEL-STR wraps around the heel comfortably, and allows the ankle joint to move freely.

Importantly, it is possible to use these units without the use of the bands, BAND-A or the BAND-B. Therefore, some units may not have the bands, BAND-A and BAND-B, or the unit may only have one of such bands. In models which do not have bands, Steps B and C from the method of use will be omitted.

Importantly, the use of end units shown at FIGS. 18-18A will be quite helpful with this unit, since it will allow the length of the heel strap to be chosen.

FIG. 25 schematically shows the general view of a support unit for the elbow. This unit has two pieces of a non-stretchable, support shown at ELBO-SUP1 and ELBO-SUP2 that are designed to stand on the front area of the elbow, above and under the elbow crease. These supports are made from Type II support means, which have a laminated body with a layer of loop-fastener attachment means, ATM1, on its outer surface, as mentioned earlier. The outer surface of these supports has a zone of hook-fastener attachment means shown at ATM2, on their left borders. A wide, continuous elastic strap, made from LYCRA, (™) shown at ELBO-STR, is attached to the right borders of the elbow supports, ELBO-SUP1-2. The elbow strap, ELBO-STR, has two free ends, F-END1 and F-END2. The inner/rear surface of these free ends has a zone of hook-fastener attachment means, ATM2. (this can be a double-sided, hook-fastener attachment means) This strap is designed to wrap around the elbow and have its free ends, F-END1 and F-END2, attached to the outer/front surface of the elbow supports, ELBO-SUP1 and ELBO-SUP2, on a detachable, re-attachable basis.

Importantly, a cut is shown on the right side of the strap that separates the free ends, F-END1 and F-END2.

Importantly, the body of the strap, STR, will first attach to the attachment zone, ATM2, from the outer surface of the support units, ELBO-SUP1 and ELBO-SUP2. This attachment is possible due to the special property of the elbow strap, ELBO-STR, which functions as the stretchable, loop-fastener attachment means. Then the attachment means, ATM2, of the free ends of the strap, F-END1 and F-END2 will attach to the outer surface of the supports, ELBO-SUP1 and ELBO-SUP2 on a detachable, re-attachable basis. This method makes a comfortable, sturdy unit for the elbow joint. Importantly, this leaves the front of the elbow open to bend freely.

Method of use.
1. The ELBO-SUP1 will be placed on the front of lower arm above the elbow crease.
2. The upper part and upper end of the ELBO-STR, will be wrapped around the elbow joint in the lower arm area above the elbow crease and its upper end piece, F-END1, will be attached to the outer surface of the support, ELBO-SUP1 on a detachable, re-attachable basis.
3. The lower part and lower end of the ELBO-STR, along its main body, will be wrapped around the elbow joint in the elbow joint, upper forearm area under the elbow crease and its end piece, F-END2, will be attached to the outer surface of the support, ELBO-SUP2 on a detachable, re-attachable basis.
4. At this point the user will be able to further adjust the end pieces to re-position the unit and change the tension of the strap by further adjustment of the free ends of the strap, F-END1 and F-END2 to make an effective, yet comfortable, unit.

Please note that importantly, the body of the strap, STR, will first attach to the attachment zone, ATM2, from the support units, ELBO-SUP1 and ELBO-SUP2. Such an attachment is possible due to the special property of the strap that functions as the stretchable, loop-fastener attachment means. Then the attachment means, ATM2, of the free ends, F-END1 and F-END2 will attach to the surface of the supports ELBO-SUP1 and ELBO-SUP2, on a detachable, re-attachable basis. This method makes a comfortable, sturdy unit for covering the elbow joint area. Importantly, this leaves the front of the elbow open to bend freely.

FIG. 26 schematically shows the general view of a support unit for the hip. This unit consists of one non-stretchable, support unit shown at SUP, that is placed on the hip/joint area. This support has zones of hook-fastener attachment means, ATM2, on its front/outer surface, that allow a strap with a loop-fastener attachment means, ATM1, to be attached to it on detachable, re-attachable basis. Alternatively, this support may have a series of D-Rings shown at D.RIN, on its sides in order to allow the free end of the straps to go through, make a U-turn, and attach to their own outer surface on a detachable, re-attachable basis. This method allows the length of the straps to be adjusted. In the models made, the applicant has used three straps with these units. This unit may have another, similar support unit to be placed on the other hip joint in order to hold the straps in a stable position. A pad will be placed under the support for better results.

FIG. 26B schematically shows a support unit for the hip that consists of hinging two support pieces so that it allows the person to bend the hip joint. In this view the first support, made from a non-stretchable piece, is shown at SUP1, and hinges to the second support, SUP2, at hinge HIN. The outer surfaces of the support pieces have zones of hook-fastener attachment means, ATM2. These zones are not shown for the Support 2, SUP2, to prevent a crowded figure. This allows a series of straps made from loop-fastener attachment means, ATM1, to be attached to the supports on a detachable, re-attachable basis. This support also may have a series of D-Rings on the sides. The supports shown at these two figures will hold a cushion pad made from a foam covered with fabric that will be attached to the support unit on a detachable, re-attachable basis. This allows the cushion to compress the wound area.

FIG. 26C schematically shows a protective support unit for a wound site which, in this model, is made for the chest wound. This design is to keep clothing away from the wound site of various forms. This model is for use after central chest opening, as common in open-heart surgeries. This unit prevents clothing from touching the chest wound, and has a rather rigid and clear support piece that will be held away from the chest wall by use of walls made of foam pads. The outer surface of the support, SUP, has zones of hook-fastener attachment means, ATM2, on its upper and side borders. That allows the straps made from loop-fastener attachment means, ATM1, to be attached to it on a detachable, re-attachable basis. The straps of this unit consists of following:
1. A vertical strap that hangs on each side of the neck, both end pieces attaching to the zone of the hook-fastener attachment means, ATM2, which is located on the upper border of the support.
2. One or two horizontal straps wrap around the chest. Their end pieces will attach to the zone of the hook-fastener attachment means, ATM2, which is located on the borders of the support on its sides. Commonly, one strap around the neck and two from the chest area are used with this unit. The straps can be stretchable or non-stretchable, but in this particular model straps made from LYCRA (™) will be particularly useful since they are fabric and will stretch well. It may have one body with four end pieces for easy connection.

FIG. 26D shows schematically the vertical, cross-cut view of the unit shown at FIG. 26C. In this figure the body of the support, SUP, is shown and has a curve that keeps it away from the wound site. The upper/outer surface of the support has hook-fastener attachment means, ATM2, on its right and left borders. The lower surface of the support has two foam pads, FOAM, that will keep the chest support, SUP, away from the chest wall.

FIGS. 27-28 schematically shows the front and rear view of a support unit for the ear. The front view is shown at FIG. 27 and is rotated 180 degrees to show its rear image that looks somewhat similar to its mirror image at FIG. 28. This unit has a support, SUP, made from a laminated body, with an outer surface made of a layer of loop-fastener attachment means, ATM1, and an inner, soft lining for contacting skin with a thin layer of foam in between. In the process of use this support will fold along a line, FO-LIN. The body of the support, SUP, on the right side has an oval opening, O-OP, with a cut, CUT, on its lower pole. This opening allows the support to be placed around the base of the ear and prevent it from moving. The rear/outer surface of the support, SUP, on the left side has two zones of hook-fastener attachment means, shown at ATM2. A wide, elastic strap, made from LYCRA, (™) and shown at HE-STR, is designed to wrap around the head. This strap is attached to the body of the support, SUP, along the dotted-line, D-LINE. Importantly, the attachment line, D-LINE, is intentionally away from the edge of the support. This allows the band of attachment means, B-ATM2, to attach to the rear surface of the support, SUP, near the D-LINE, so that the strap will finally wrap over this band.

At the time of use:
A. The oval opening, O-OP of the body of the support, SUP, will be placed around the base of the ear via the cut, CUT. This method will prevent the movement of the support after placement.
B. The rear half of the support, SUP, shown at the left side will fold along the folding line, FO-LIN, and cover the ear. The free borders of these two pieces will be held together by attaching the band of the attachment means, B-ATM2, to the rear surface of the support, SUP, adjacent to the D-LINE. The folded support holds the dressing of the ear on it securely.
C. Then the head strap, HE-STR, which is made from Lycra (™) will wrap around the head horizontally, on the front of the head, the temporal side and the occipital area respectively. So that ultimately, its free end will attach to the outer surface of the folded support, SUP, by use of the two zones of the attachment means, ATM2.

This method makes a secure and simple means of holding the dressing on the ear, which is commonly difficult.

The body of the support may be made to have more foam and be thicker, or also to have a more protective, non-compressible body to avoid compression of the ear. The strap may also have a piece to go vertically and use the method shown for the head support.

Importantly, a small envelope made from fabric may be used to go over the wound of the ear and be held in place by this unit.

FIG. 29 schematically shows the side view of the unit shown at the previous two figures. This figure shows the support, SUP, the zones of the hook-fastener attachment means, ATM2, on its lower surface, (only one zone is marked), the folding line, FO-LIN and the head strap, HE-STR. Note the point of the attachment of the head strap, HE-STR to the body of the support, SUP, marked at D-LINE is intentionally away from the very edge of the support, SUP. This allows the band of the attachment means, B-ATM2 to attach to the rear surface of the support, SUP, near the D-LINE. This special design allows the head strap, HE-STR, to wrap over this band.

FIG. 30 schematically shows the general view of a support unit for the Pacemaker-Defibrilator Wound. This unit consists of a non-stretchable support unit, SUP, that stands on the front of the upper chest in the subclavian area and holds a pad, PAD, on the wound site. The pad, PAD, is attached to the inner surface of the support, SUP, on the upper half of the support, by an attachment means such as a hook-fastener attachment means, ATM2. The body of this support is made from a laminated body with an outer surface made from a layer of loop-fastener attachment means, ATM1, and an inner soft lining for contact skin, with a thin layer of foam in between. The upper half of the support has a thicker body made from the folding of the support material. The body of the support in this segment makes a U-turn and attaches to its own body, shown better at U-SUP at FIG. 31. Thus, this part has a body with a surface made of a loop-fastener attachment means, ATM1, on both sides. The support and attached pad will be held in the wound site (the subclavian area) by use of two straps.

These straps are made from laminated layers of loop-fastener attachment means, ATM1, both its inner and outer surfaces with a thin layer of foam in between. The straps consist as follows:

a. A horizontal strap shown at H-STR that is designed to wrap around the chest and attach to the outer surface of the support, SUP, by use of a zone of hook-fastener attachment means, ATM2. This is located on both ends of the strap or by use of an extra piece of a double-sided ATM2.
b. A vertical shoulder strap, S-STR, that sits on the shoulder. The rear end of this strap makes a U-turn around the horizontal strap, H-STR, shown at U1, (best shown at FIG. 31A) to attach to the surface of its own body. This will in turn keep the horizontal strap H-STR and the shoulder strap, S-STR, attached to each other on an adjustable basis, and shown best at FIG. 31A.
c. The front portion of the shoulder strap, S-STR, stands in front of the support, SUP, and may attach to it through use of pieces of double-sided hook-fastener attachment means, ATM2. The strap then moves down and wraps around the patient's wrist, so as to make a U-turn and move up to attach to its own surface as shown at U2 FIG. 31A.

This unit:
1. Provides a compression to the wound site and prevents hematoma.
2. Will hold the wrist of the patient in position and prevent it from moving.
3. Will prevent other objects from reaching the wound site and causing pain.

Importantly, the size, shape and makeup of the pads may vary. Also, the nature of the straps may vary, made to be:
1. Non-stretchable
2. Of a stretchable, elastic material
3. Of a combination of non-stretchable and stretchable materials.

The elastic straps may have their own attachment property or they may have pieces of attachment means attached to their body.

Importantly, in these units the body of the support is primarily made from a material that has an outer surface made from a layer of loop-fastener attachment means, ATM1, and its inner surface is a soft lining that would stand on the skin, with a thin layer of foam in between. This allows the shoulder and horizontal straps to be attached to the surface of the support in any area by placing a piece of double-sided hook-fastener attachment means, ATM2, between them. This design and method makes these units more versatile and stable.

FIG. 31 schematically shows the side view of the support unit shown in FIG. 30. In this figure the support, SUP is shown with the upper body of the support made from a folded support material, so that the upper half has an outer surface made of a loop-fastener attachment means, ATM1, on both sides as shown at U-SUP. The pad, PAD is attached to the front surface of the U-SUP. The rear surface of the pad is specified at S-PAD and may have a layer of loop-fastener attachment means, ATM1. The pad, PAD, is attached to the inner surface of the support, U-SUP, through use of attachment means, ATM2.

FIG. 31A schematically shows the side view of the arrangement of the straps. In this view the shoulder strap, S-STR, stands on the shoulder (not shown). The rear segment of the strap makes a U-turn, U1, around the horizontal strap, H-STR, and attaches to its own body by use of ATM2, on a detachable, re-attachable basis. This keeps the horizontal strap, H-STR, and the shoulder strap, S-STR, attached to each other on an adjustable basis.

The front segment of the shoulder strap, S-STR, stands in front of the support (not shown) and may attach to it by use of pieces of double-sided, ATM2. It moves down in front of the chest, the free end of the strap making a U-turn, U2, around the wrist, WR, of the patient and attaches to the front surface of its own body by the zone of the ATM2 at its end.

FIG. 32 shows a support unit similar to the unit shown in FIG. 30, except this unit has two complementary support pieces. The first support stands on the front of the chest and is referred to as the Front Support, F-SUP, and the second support stands on the back of the chest and is referred to as the Rear Support, R-SUP. The Front Support, F-SUP, stands on the wound site and will be kept in place through use of horizontal and vertical straps: a strap in the right side, R-STR, another strap on the left side, L-STR and a vertical strap, V-STR that will come together and attach to the surface of the Rear Support, R-SUP. The free ends of these straps have pieces of hook-fastener attachment means shown at, ATM2, that attach to the surface of the R-SUP, made from the laminated body with an outer surface made of a layer of loop-fastener attachment means, ATM1, with an inner soft lining and layer of foam in between. The outer surface (the side that does not come in contact with the body site) of the support also has zones of hook-fastener attachment means, ATM2. This allows the body of the strap to attach to these attachment means on a detachable, re-attachable basis. Thus, the rear support, R-SUP, will in fact act as a catalyzer, allowing the ends of the straps to attach to each other easily. Alternatively, the free ends of the attachment means may be attached to each other through use of double-sided loop or hook fasteners, ATM1 and ATM2. The dressings or pads may be placed under the front or rear support.

Importantly, this model makes the process of the dressing easier in some cases by preventing a crowded area in front. Importantly, the front support may have a body made of stretchable or non-stretchable layers.

FIG. 33 shows the general view of a support unit similar to the unit shown at FIG. 6, except this unit is modified for use in the arm and forearms to allow the wound dressing and/or compression of limb in these areas. This unit allows a secure and easy dressing without the need for adhesive tapes. In this model the support, SUP, has a long, rather rectangular shape with cuts in its sides, CUT, for composure on the elbow crease. The support of this unit stands on the front of the arm and forearm, or on its rear. The support, SUP, has a long zone of hook-fastener attachment means, ATM2, on its left border that allows pieces made of loop-fastener attachment means, ATM1, or a strap made from lycra to be attached to it on a detachable, re-attachable basis. Importantly, the support may have two parallel zones of long zones of hook-fastener attachment means, ATM2, on its outer surface as shown in FIG. 1C.

The right border of the support unit, SUP, is attached to a series of straps: STR-A, STR-B that will wrap around the arm and STR-C, STR-D and STR-E, which are designed to wrap around the forearm. These straps are attached to the border of the support, SUP, on a permanent basis, although importantly, they may be attached to the support on a detachable, re-attachable basis as shown for the leg support. These straps are properly sized to be wrapped around the arm from the axillary area to the elbow-joint area. Importantly, this unit may have three or more straps for the arm part as well.

The straps for the forearm will be placed in the upper, mid- and lower forearm.

These straps may be attached to the support, SUP, by use of pieces of loop-fastener attachment means, ATM2, at their ends. Similar to the leg straps, this method allows the unit to be used for dressing, supporting and compressing the arm and forearms in a very practical, adjustable manner. In this model the straps are also made from one or two layers of LYCRA (™) and the support means, SUP, is made from a non-stretchable, vinyl, or may be made from a laminated body with an outer surface made from a layer of loop-fastener attachment means, ATM1, and an inner layer made from a soft lining that stands on the skin with a thin layer of foam in between. It may also be made from any other materials such as fabric or any other man-made materials. The support may have openings to allow sweat and air to move and also allows a gauze pad or long, removeable layer of lining shown at LIN, in FIG. 6A or a pad to be placed under it to prevent irritation, place pressure, and allow the application of medication, etc. This unit allows the placement of electrical leads in the area for a programmed stimulation of the arm muscles and tissues for reasons such as the prevention of muscle weakness or prevention of phlebitis. Importantly, the narrow area of the support between two cuts, CUT, on each side will function, too.

1. Keep the lower part of the support in place and prevent it from falling.
2. It will function as a hinge and allows the lower segment of the support to rotate in different directions (compared to the upper part) without being disconnected from the upper segment.
3. Importantly, the area in the cut may be made from a detachable and re-attachable means to allow these two supports to be separated from each other or the size to be adjusted.

The advantage of this unit is that:
1. It makes the placement of this unit by one hand possible.
2. It makes it possible to adjust the tension of strap individually, which allows the pressure in each segment of the arm or forearms to be modified without disturbing the whole unit. This is not possible through a commonly-used wrapping system.

3. The arm and the elbow to function easily due to presence of the cut in the support.
4. The arm and elbow to be hung from a stand in order to facilitate the drainage of the tissue. This is explained later.
5. This unit can be placed and removed rather easily. Since placement of only one strap holds the support in place and allows the other straps to be placed. Then, by adjusting each strap the whole unit can be adjusted.
6. Placement of a lining which may be attached to the support, SUP, of the unit on a detachable, attachable basis. This allows the lining to be washed or exchanged.

The lower part of this figure shows a piece that allows this unit to be extended to the hand area and be attached to an automatic height elevator shown at FIG. 34. This part shows a support for hand, SUP, that stands on the rear of the hand, and will be attached to the lower extension of the support of the arm-elbow by the hook-fastener attachment means, ATM2, in the upper end of the hand support. The straps of this support will wrap around the palm and fingers and will attach to the rear surface of the body of the hand support. The hook in its lower end allows this support to be attached to the hook, HOOK, of the remote-controlled elevator from FIG. 34.

Please note that the straps shown in the upper part of the picture are not attached to each other and are separate, so that they can be attached to the support individually.

Importantly, the straps of these units may be attached to the support unit independently by having both their ends attached to each side of the support on a detachable, re-attachable basis.

Importantly also, the straps may be made from a continuous layer of LYCRA, (™), to allow a uniform coverage of the area. Through this, one continuous layer of the strap is attached to the border of the support without having a cut or space in the body of the strap in this side, similar to the model shown at FIG. 6C for the leg. However, their very end pieces will be separate to allow easy placement. An example of this model is shown for the leg at FIG. 6C, and is not repeated here to avoid a lengthy application.

Importantly, a similar unit may be used for the hip wounds, so that the cut can stand on the hip joint and allow the joint to function. In this model the upper part will have only one strap and the lower part to have one or two straps. The model for the hip joint will use pads which will be placed under the support and may consist of three pieces as shown in FIG. 35A, so that the middle piece can be removed when the user wishes to sit.

FIG. 34 shows schematically a limb elevator which allows a limb to be lifted by being raised from below or to be pulled up by being hung to its hooks, HO. This unit consists of a remote-controlled electrical motor that rotates the wheel, RW which is secured on a pole, PO, that stands on a base, BA. The unit has a limb stand, LS, which has a flat surface that allows one or two limbs to be placed on it. The lower surface of the limb stand, LS, has hooks, HO that allows a limb support to be hooked to it and be raised when the base is moved up. The base holds a pipe which can move up and down over a central shaft, CS. The outer surface of this pipe of the limb stand, LS has an indented zone, EP which engages with the teeth of the rotating wheel, RW. By utilizing this method, the rotation of the wheel will move the pipe up and down for elevation of the limb stand, LS. The central shaft, CS and the pole, PO stand on a base, BA. A remote controller, RC, controls the movement of the electrical motor and thus controls the movement of the wheel from a distance. The elevation of the hands or feet by this unit will facilitate the movements of the fluids in the tissue toward the trunk and will reduce the swelling of the limb. This unit will be useful in cases such as breast removal or swelling of the arms or legs due to vascular problems.

Importantly, this unit may be modified for placement in the lower bed area, which will allow the user to place his/her legs on the limb stand and have them raised.

The limb stand, LS of this unit will be moved down to stand on the bed surface so that the user can place his/her feet on the top of the limb stand, LS. Then the limb stand, LS will move up by use of the remote controller, RC. Importantly, this model not only allows the limbs to be raised, but its design also allows the limbs to be hung in its hook, HO and then moved up and down as desired.

Many other methods such as Jack type machinery may be also used to elevate the limb stand, LS. An extension can be incorporated in this unit for the height control. Importantly, the base of this unit may be used:
1. By attachment to the bed structure.
2. Can be moved around and may have wheels of its own.

FIG. 34A shows schematically a unit that allows a limb to be placed on it and be lifted by the elevator shown at FIG. 34. This piece will tolerate the weight of the limb and prevent joint discomfort.

This unit consists of the following.
a. A flat base designed for placement under the bed or the trunk of the user, and is schematically shown as body rest, BR. This piece allows the body to rest on it, and is hinged/attached to a cradle, AR, designed for the placement of a limb.
b. The cradle, AR, is hinged/attached to the body rest from one end and has an extension for placement of a hand or foot, and is shown at HR.
c. The hand or foot rest, HR, has a hook, HO, that allows it to be hung on the HO, of the elevator shown at FIG. 34.
d. The unit may have a series of straps to help in keeping the limb in place.

This unit may have a rigid cradle or a cradle made from a non-stretchable fabric or combinations. In either case, it will have proper cushioning to make a comfortable bed for the limb.

FIG. 35 shows the general view of a support unit similar to the unit shown at FIGS. 6 and 33, except this unit is modified for use in the thigh. This unit has a long, rectangular support, SUP, with cuts, CUT in the sides. These cuts, CUT are designed to stand on the hip joint and functions as a hinge. The upper part of the support, SUP, above the cut, CUT, is for placement on the waist and its lower part is to be placed on the lateral side of the thigh. The area between the cuts, CUT, will allow the lower part of the support, SUP, to rotate in the different directions without being disconnected from the upper part. Therefore, it allows the lower piece of the support to move in a relatively independent fashion and allow the hip joint to function. Importantly, the area between the cut, CUT may be made from a detachable and re-attachable and adjustable piece to provide further freedom.

This model will use pads which will be placed under the support and may consist of three separate pieces, with the middle piece having a wedge shape and being removed when the user is sitting.

The support, SUP, has a series of straps attached to it. The first strap functions as the belt and is marked as BELT. This will hold the support and prevent it from falling. Other straps, STR-1, STR2, and STR-3, are attached to the body of the support on a permanent basis in one side. These straps will individually wrap around the thigh and attach to the hook-fastener, attachment means, ATM2, of the support due to their own properties which allow such an attachment. Also due to the presence of the hook fastener attachment means, ATM2, at the free ends of the strap, and on a detachable, re-attachable basis (as shown for the leg support), these straps are properly-sized to wrap around the thigh from the groin to the upper knee. Importantly, the support, SUP, may have an extension to cover the knee area with a strap going around the knee.

Importantly, the extension, shown at EXT, will allow the attachment of this unit to a leg support.

Importantly, the effective length of these straps may be modified by use of the methods and means explained in this application. Similar to the leg straps, this method allows the support and straps to be used for dressing and supporting the thigh in a very practical, adjustable manner. In this model the straps are also made from one or two layers of LYCRA (™) and the support means, SUP, is made from non-stretchable, clear vinyl or a laminated body with an outer surface made from a layer of loop attachment means, ATM1. It may also be made from any other materials such as fabrics or any other proper man-made materials, however, in such case they need to have their own attachment means to attach to the support unit.

Importantly, the thickness of the straps may vary in this unit and every other units to fulfill the need; thinner straps will hold dressing in place while the thicker straps will allow more tension build up and pressure in the tissues.

The support may have openings to allow sweat and air to pass through and also allows gauze pad or a long, removeable layer of lining shown at, LIN, in FIG. 6A or pad to be placed under it to prevent irritation, place pressure, allow application of medication, etc. This unit also allows other means such as electrical leads to be held in place to allow a programmed stimulation of the muscles and tissues in this area for various reasons, such as prevention of muscle weakness or prevention of phlebitis.

The advantage of this unit is that it allows compression of the whole thigh with the option to adjust the pressure in each segment of the thigh. Also the unit can be removed and placed with ease. When a lining is used it may be attached to the support, SUP of the unit on a detachable, re-attachable basis. This allows the lining to be washed and used or exchanged when needed.

Please note that these straps are not attached to each other and are separate.

Importantly, the straps of may be attached to the support unit independently, by having their both ends attached to each side of the support on a detachable, re-attachable basis.

Importantly, the straps may be made from a single layer of LYCRA (™) to allow a uniform cover of the area although their end pieces or the attachment means and the area adjacent to it will be separated to allow easy placement. An example of this model is shown for the leg and will not be repeated to avoid a lengthy application.

Method of use.
1. The user places the support, SUP, on the side of the hip so that the cut, CUT, will be at the hip joint.
2. The user will wrap the belt, BELT, around the waist and attach its free end to the outer surface of the support, SUP, and then attaches the free end of the belt to the outer surface of its own. This is possible due to the presence of the attachment means at the end of the belt and the fact that the belt has a body made from a layer of loop-fastener, attachment means on its own inner and outer surfaces.
3. The user will wrap the stretchable straps, STR-1, STR-2 and STR-3, around the thigh and attach their free end to the hook fastener attachment means of the support marked at H-ATM2, and will continue to attach the free ends of the straps to the outer surface of their own if the strap was longer. Other means of such an attachment may be used as explained in the text.
4. Further adjustments allows the unit to be in its proper condition.

Importantly, the straps for the thigh may be made from a continuous elastic layer such as LYCRA, (™), to allow a uniform coverage of the area. So that one continuous layer of the strap is attached to the border of the support without having a cut or space in the body of the strap in this side, similar to the model shown at FIG. 6C for the leg. However, their end pieces will be separate to allow easy placement. An example of this model is shown for the leg at FIG. 6C and is not repeated here to avoid a lengthy application.

FIG. 35A, shows schematically a pad unit which consists of three pieces: PAD-A, PAD-B and PAD-C, which are loosely attached by use of an attachment means and can be separated when desired. This method allows the middle piece to be removed when the user wishes to sit.

FIG. 36 shows the general view of a support unit that is similar to the unit shown at FIG. 35, except that it is modified for use in the groin area to hold a pad over the wound area in the inguinal region. A sample of such a pad is shown at PAD, which has a trapezoid-shape and can be used after cases such as a hernia surgery in this region. This unit has a support, SUP, that extends and moves down to cover the inguinal area. The body of this support is made from a Type II support which is a non-stretchable layer, such as a laminated body, with an outer surface made from a layer of loop fastener attachment means, ATM1, an inner soft lining for contact skin with a thin layer of foam in between. It may also be made from any other manmade material. The support, SUP, will be held in place securely by a non-stretchable strap, NS-STR, that is attached to the support, SUP, on one side in a permanent or detachable, re-attachable basis. This allows the other end of the strap to wrap around the waist and function as a belt. The belt strap will hold the support, SUP, in a stable position. Please note that due to the extra length of the strap, NS-STR it is schematically shown with a cut in its length. A second, but stretchable strap, S-STR, is attached to the body of the NS-STR, on a detachable, re-attachable basis on the posterior part of the NS-STR. This method allows the stretchable strap, S-STR, to move down the buttock area and pass the inner side of the groin, moving up and attaching to the horizontal hook-fastener, attachment means of the support marked at H-ATM2. This combination makes a secure unit for holding the support unit and compresses the pad, PAD, on the wound area in the groin.

Importantly, when the stretchable strap, S-STR, is made from LYCRA (™) it will:
1. Expand in the back to function as a comfortable layer of fabric
2. Shrink and roll in the groin area to limit its presence and the pressure to the sides of the groin.
3. Expand like a wing and cover a wider area in the inguinal area in order to hold the support means, SUP, in a stable condition.

This combination makes a fine unit for this use.

Importantly, the stretchable strap, S-STR, attaches to the body of the NS-STR on a detachable, re-attachable basis so that the position and location of such an attachment can be changed as needed.

Importantly, the straps may be attached to the support unit independently, by having both their ends attached to each side of the support on a detachable, re-attachable basis.

Method of use.
1. The user will place the combination of the pad, PAD and support, SUP on the inguinal wound site.

2. The user will wrap the non-stretchable strap, NS-STR, around the waist and attach its free end to the outer surface of the support, SUP, due to the presence of the attachment means.
3. The user will move the stretchable, strap, S-STR, down from the buttock area and pass it from the inner side of the groin, moving it up and attaching it to the horizontal hook fastener attachment means of the support marked at H-ATM2.
4. Further adjustments allow the unit to be in its proper condition.

FIG. 37 shows schematically the side view of a special foot pedal, designed for use by patients with peripheral vascular disease. This will allow them to pedal for improvement. The use of this unit will not only improve the circulation in the feet and the legs due to the exercise and exercise related vasodilation, but will also improve the movement of the extra fluid in the legs.

This unit consists of.
a. Pole, POLE which stands on a base, BASE and functions to hold the axle, AXEL of the pedals. This pole will be made from combinations of poles to allow the length of this piece to be adjusted.
b. A base, BASE that allows the pole to be placed on the bottom of a bed spring or similar area. This will be fixed on the bed by various means, such as clamps, etc. In this prototype model it is designed to sit on the top of the base board of hospital beds.
c. The unit has an axle, AXEL that connects the pedals together and allows them to rotate function like the pedals of a bicycle.
d. Specially, designed, cushioned and protected foot pedals, PED-1, PED-2 which are made to allow the foot of the user to be placed on them and prevent the compromised tissues of the feet and leg from being damaged. The heel of the foot will be placed on pedals with horizontal, lower walls and push a vertical, flat wall. The pedals also have side walls which are designed to prevent each foot from moving to the sides, thus preventing the feet from being injured.
   These pedals allow the feet to be placed inside and be kept in place by use of bands which will stand in front of the ankles, and keep the feet on the pedals. This is particularly important if the patient is too weak or has neuro-muscular problems, which do not allow them to keep their feet inside the pedals. This design is important since it will prevent further trauma to the compromised and vulnerable tissues of the feet, and will keep the feet stable to benefit from exercise.
e. The unit also has side walls which are made from a circular well-padded pieces, shown at CIR, in this picture and CIR-R AND CIR-L in FIG. 38. The circular pieces, CIR, are fixed to the free ends of the axle, AXEL, from one side and hold the poles, POL1, of the foot pedals, PED-1. This allows the foot pedals to rotate around their poles, and is shown better at FIG. 39. This design is chosen for such a use since it does not have sharp ends or points for a potential trauma to the feet.
f. An electrical motor, EM schematically shown, allows the circular pieces, CIR-R AND CIR-L and the attached pedals, PED-1 AND PED-2 to rotate automatically due to the power of the electrical motor, EM.
   The speed of the rotations will be controlled by the electrical motor, EM.
   This method allows the feet of weak patients to be moved in order to circulate the blood and help the muscles tones. The transfer of the movement from the electrical motor, EM to the axle, AXEL may be done by use of chains or wheels used in bicycles or similar means.
g. A computerized programmer (not shown since it will be part of the electrical motor, EM) will allow the timing, frequency of function, the resistance, duration of use and other important factors of such automatic unit to be controlled.
h. A remote controller allows the function of the computer to be adjusted from a distance.

FIG. 38 shows schematically the front view of a specially designed foot pedal shown in FIG. 37. In this figure the:
a. Pole, POLE is shown, which functions to hold the axle, AXEL, of the pedals on its top and stands on the base, BASE, in its lower end.
b. The base, BASE is shown and holds the pole, POLE and allows the pole to be placed on the bottom of a bed spring or similar place.
c. The Axle, AXEL, moves horizontally, from the CIR-R to CIR-L and goes through the pole, POLE, to allow the circular pieces to rotate around the axle, AXEL. p1 d. The foot pedals, PED-1 and PED-2, are schematically shown.
f. The electrical motor, EM, is shown schematically.
g. A computerized programmer is part of the electrical motor, EM.
h. A remote controller, similar to the unit shown at RC at FIG. 34, is not shown in this picture but allows the function of the electrical motor, EM, to be adjusted from a distance.

FIG. 39 shows schematically one well-padded foot pedal such as PED-1 that has side walls designed to prevent tissue damage. This unit has padded walls that allow the feet to be seated for a comfortable safe usage. The side walls prevent the feet from moving to the sides. The strap, STR, goes from one wall and attaches to the outer surface of the other wall and keeps the foot in place, in case the patient is too weak or has neuro-muscular problems that prevents them from keeping their feet on the pedals. The pole, POL1, attaches to the circular flat piece, CIR-R and allows the pedal to rotate around it. The inner surface, IS, of this pedal is cushioned and the outer surface, OS, is shown, and can be made from a rather rigid plastic or a protective fabric.

Use of tabs with these units.

These units may have optional tabs on the surfaces of the supports or the straps in order to allow them to be held or to move the support or straps. The tabs will allow the pulling of the strap so the user can adjust it or change the dressing underneath without disturbing the whole unit.

The method of making the support unit. At present the supports are made by adhering the hook-fastener attachment means to the surface of the supports made from a non-stretchable material such as vinyl/PVC which is time consuming and difficult. However, the applicant has previously disclosed to the USPTO, that these supports may be made by various means such as extrusion, etc., to make a layer of vinyl/PVC that has zones of flat surfaces in between the hook-fastener attachment means with the sizing and design for use as a support piece with these models. What this method will do is to reduce the following steps:
1. Making the hook-fastener attachment means.
2. Attaching a layer of adhesive to the rear surface of the hook-fastener attachment means.
3. Making the layer of vinyl/PVC means.
4. Attaching a the hook-fastener attachment means to the layer of vinyl/PVC.

Changing these steps to one step of making a layer of vinyl/PVC with zones of flat surfaces in between the hook-fastener attachment means with the sizing and design for use as a support piece with these models. The applicant believes this will reduce the cost and greatly benefit humans and animals. He has the intention of asking for such a patent if the rules of USPTO allow.

Please note that size, shape, thickness, color, materials and other important characteristics of these units and their components may vary.

The invention claimed is:

1. A wrap for encircling portions of a living body proximal and distal to a skeletal joint, the wrap comprising:
   A) a relatively non-stretchable support comprising a first zone for placement against the body proximal to the joint, and a second zone for placement against the body distal to the joint;
   B) a first strap that encircles a portion of the living body proximal to the joint for holding the first zone of the support against the body; and
   C) a second strap attached to the second zone and comprising relatively stretchable material that i) allows the second strap to stretch as it encircles the body distal to the joint and ii) directly attaches to attachment means on the second zone of the support to keep the encircled portion of the living body distal to the joint compressively wrapped.

2. A wrap as set forth in claim 1 wherein the first strap is attached to the first zone of the support and comprises relatively stretchable material i) that allows the first strap to stretch as it encircles the body proximal to the joint and ii) that directly attaches to an attachment means on the first zone to keep the encircled portion of the living body proximal to the joint compressively wrapped.

3. A wrap as set forth in claim 2 wherein one type of fastener material is disposed at the end of each strap beyond a zone of stretchable material that is directly attaching the respective strap to the attachment means on the support when the wrap has been applied to compressively wrap the portion of the living body, the one type of fastener material providing for detachably, re-attachably attaching the end of the respective strap to a complementary type of fastener material forming the outer surface layer of the respective zone of the support.

4. A wrap as set forth in claim 3 wherein the one type of fastener material at the ends of the straps comprises hook-type fastener material.

5. A wrap for encircling portions of a living body proximal and distal to a skeletal joint, the wrap comprising:
   A) a relatively non-stretchable support comprising a first zone for placement against the body proximal to the joint, and a second zone for placement against the body distal to the joint;
   B) a first strap that encircles a portion of the living body proximal to the joint for holding the first zone of the support against the body; and
   C) a second strap attached to the second zone and comprising relatively stretchable material that i) allows the second strap to stretch as it encircles the body distal to the joint and ii) directly attaches to attachment means on the second zone of the support to keep the encircled portion of the living body distal to the joint compressively wrapped;
   wherein the first and second zones of the support are connected together such that they can turn relative to each other as the skeletal joint articulates.

6. A wrap for encircling a portion of a living body, the wrap comprising:
   A) a relatively non-stretchable multi-laminar support that is to be disposed against the portion of the living body and comprises an outer surface layer of one type of fastener material;
   B) a strap extending from the support for encircling the portion of the living body and comprising relatively stretchable material that stretches as the strap is encircling the body and directly attaches to an attachment means on the support to keep the encircled portion of the living body compressively wrapped; and
   C) another type of fastener material disposed at an end of the strap beyond a zone of stretchable material that is directly attaching the strap to the attachment means on the support when the wrap has been applied to compressively wrap the portion of the living body, the another type of fastener material providing detachable, re-attachable attachment of the end of the strap to the one type of fastener material of the outer surface layer of the support.

7. A wrap as set forth in claim 6 wherein the end of the strap comprises discrete tongues, each having the another type of fastener material providing detachable, re-attachable attachment of the tongues to the one type of fastener material of the outer layer of the support.

8. A wrap as set forth in claim 7 wherein the support comprises support portions connected together such that the support portions can turn relative to each other, and the strap comprises separate strap portions, each extending from a respective support portion and comprising relatively stretchable material that stretches and directly attaches to a respective attachment means on a respective support portion when the wrap has been applied to compressively wrap the portion of the living body, each strap portion further comprising another type of fastener material disposed at a respective end beyond a zone of stretchable material that is directly attaching the respective strap portion to the respective attachment means providing detachable, re-attachable attachment of the end of the respective strap portion to the one type of fastener material of the outer surface layer of the respective support portion.

9. A wrap as set forth in claim 8 wherein the strap comprises at least three such strap portions, at least two of which extend from one of the support portions.

10. A wrap as set forth in claim 9 wherein one of the strap portions extends from one of the support portions and multiple strap portions extend from another of the support portions, and the one of the strap portions has a length sufficient to girdle a portion of the body that anatomically includes opposite lateral sides of the vertical medial plane through the body.

11. A wrap as set forth in claim 10 wherein the multiple strap portions have different lengths.

12. A wrap as set forth in claim 9 further including a connection piece having detachable, re-attachable attachment to the one support portion to provide for connection of a distal end of the wrap to an elevator.

13. A wrap as set forth in claim 12 wherein the connection piece also comprises at least one strap for wrapping around a further portion of the body to hold the connection piece on that further portion of the body.

14. A wrap as set forth in claim 8 wherein the support comprises one or more cut-outs separating the respective support portions to allow them to turn relative to each other.

15. A wrap as set forth in claim 7 wherein the support comprises separate support portions from which the strap extends, each support portion comprising its own attachment means to which the stretchable material directly attaches when the wrap has been applied to compressively wrap the portion of the living body.

16. A wrap as set forth in claim 6 wherein the another type of fastener material comprises hook-type fastener material.

17. A wrap as set forth in claim 6 further including a second strap extending from the support for further strapping of the support to the body and comprising relatively stretchable material that stretches as the second strap is further strapping the support to the body and that directly attaches to the attachment means on the support, an end of the second strap beyond a zone of stretchable material that is directly attaching the second strap to the attachment means on the support when the wrap has been applied to compressively wrap the portion of the living body comprising the another type of fastener material providing detachable, re-attachable attachment of the end of the second strap to the one type of fastener material of the outer surface layer of the support.

18. A wrap as set forth in claim 17 wherein the straps are generally parallel with each other.

19. A wrap as set forth in claim 18 wherein the straps are attached respectively to opposite sides of the support for wrapping in opposite circumferential senses.

20. A wrap as set forth in claim 17 wherein the second strap wraps in a transverse sense to the direction of wrapping of the other strap.

* * * * *